(12) United States Patent
Vazquez et al.

(10) Patent No.: US 12,246,004 B2
(45) Date of Patent: Mar. 11, 2025

(54) THERAPEUTIC TREATMENT OF MICROSATELLITE UNSTABLE CANCERS

(71) Applicants: THE BROAD INSTITUTE, INC., Cambridge, MA (US); DANA-FARBER CANCER INSTITUTE, INC., Boston, MA (US); INSTITUTO CARLOS SLIM DE LA SALUD, A.C., Colonia Granada Ampliacion (MX)

(72) Inventors: Francisca Vazquez, Cambridge, MA (US); Adam Bass, Boston, MA (US); Tsukasa Shibue, Cambridge, MA (US); Edmond Chan, Boston, MA (US); James McFarland, Cambridge, MA (US); Mahmoud Ghandi, Cambridge, MA (US); Aviad Tsherniak, Cambridge, MA (US)

(73) Assignees: THE BROAD INSTITUTE, INC., Cambridge, MA (US); INSTITUTO CARLOS SLIM DE LA SALUD, A.C., D.F. (MX); DANA-FARBER CANCER INSTITUTE, INC., Boston, MA (US)

( * ) Notice: Subject to any disclaimer, the term of this patent is extended or adjusted under 35 U.S.C. 154(b) by 1027 days.

(21) Appl. No.: 15/734,131

(22) PCT Filed: Jun. 3, 2019

(86) PCT No.: PCT/US2019/035130
§ 371 (c)(1),
(2) Date: Dec. 1, 2020

(87) PCT Pub. No.: WO2019/236448
PCT Pub. Date: Dec. 12, 2019

(65) Prior Publication Data
US 2022/0133693 A1 May 5, 2022

Related U.S. Application Data

(60) Provisional application No. 62/853,412, filed on May 28, 2019, provisional application No. 62/680,322, filed on Jun. 4, 2018.

(51) Int. Cl.
| | | |
|---|---|---|
| A61K 31/7105 | (2006.01) |
| A61K 31/4015 | (2006.01) |
| A61K 31/4025 | (2006.01) |
| A61K 31/473 | (2006.01) |
| A61K 31/497 | (2006.01) |
| A61K 31/519 | (2006.01) |
| A61K 31/5377 | (2006.01) |
| A61K 31/585 | (2006.01) |
| A61P 35/00 | (2006.01) |
| C12Q 1/68 | (2018.01) |
| C12Q 1/686 | (2018.01) |
| C12Q 1/6886 | (2018.01) |

(52) U.S. Cl.
CPC ...... *A61K 31/4025* (2013.01); *A61K 31/4015* (2013.01); *A61K 31/473* (2013.01); *A61K 31/497* (2013.01); *A61K 31/519* (2013.01); *A61K 31/5377* (2013.01); *A61K 31/585* (2013.01); *A61K 31/7105* (2013.01); *A61P 35/00* (2018.01); *C12Q 1/686* (2013.01); *C12Q 1/6886* (2013.01); *C12Q 2600/106* (2013.01)

(58) Field of Classification Search
None
See application file for complete search history.

(56) References Cited

U.S. PATENT DOCUMENTS

2021/0155932 A1* 5/2021 Billy .................. A61K 31/7088

FOREIGN PATENT DOCUMENTS

WO 2013153130 A1 10/2013

OTHER PUBLICATIONS

International Search Report dated Dec. 17, 2020 for related Application No. PCT/US2019/035130.
Chan, E. et al. WRN helicase is a synthetic lethal target in microsatellite unstable cancers, vol. 568, No. 7753, Apr. 10, 2019.
Behan, F. et al. Prioritization of cancer therapeutic targets using CRISPR-Cas9 screens, vol. 568, No. 7753, Apr. 10, 2019.
Lorn, K. et al. Wener Syndrome Helicase is Required for the Survival of Cancer Cells with Microsatellite Instability, Mar. 29, 2019.
Orlovetskie, N. et al. Targeted inhibition of WRN helicase, replication stress and cancer, vol. 1867, No. 1, Nov. 27, 2016.
A. Arai et al. RECQL1 and WRN Proteins are Potential Therapeutic Targets in Head and Neck Squamous Cell Carcinoma, vol. 71, No. 13, May 13, 2011.

(Continued)

*Primary Examiner* — Sean McGarry
(74) *Attorney, Agent, or Firm* — Withers Bergman LLP; Christopher R. Cowles

(57) ABSTRACT

The present disclosure relates to compositions and methods for the diagnosis and treatment or prevention of microsatellite unstable cancers. In particular, the instant disclosure provides for identification of a cancer as exhibiting microsatellite instability (MSI) and/or impaired mismatch repair (MMR), and selection and/or administration of an inhibitor of the WRN helicase as a therapeutic agent for such a cancer and/or subject having or at risk of developing such a cancer.

10 Claims, 52 Drawing Sheets
Specification includes a Sequence Listing.

(56) References Cited

OTHER PUBLICATIONS

Extended European Search Report in corresponding EP application No. 19815140.9 dated Mar. 2, 2022.
Samadder et al., Cancer TARGETases: DSB repair as a pharmacological target, Pharmacology and Therapeutics, Feb. 18, 2016, vol. 161, pp. 111-131; p. 122, col. 1, para 4; p. 122, col. 2, para 1.
International Search Report dated Aug. 16, 2019 for related Application No. PCT/US2019/035130.

* cited by examiner

SEQUENCE LISTING

```
<160> NUMBER OF SEQ ID NOS: 29

<210> SEQ ID NO 1
<211> LENGTH: 20
<212> TYPE: DNA
<213> ORGANISM: Artificial
<220> FEATURE:
<223> OTHER INFORMATION: Synthetic

<400> SEQUENCE: 1
gtaaattgga aaacccacgg                                              20

<210> SEQ ID NO 2
<211> LENGTH: 20
<212> TYPE: DNA
<213> ORGANISM: Artificial
<220> FEATURE:
<223> OTHER INFORMATION: Synthetic

<400> SEQUENCE: 2
atcctgtgga acataccatg                                              20

<210> SEQ ID NO 3
<211> LENGTH: 20
<212> TYPE: DNA
<213> ORGANISM: Artificial
<220> FEATURE:
<223> OTHER INFORMATION: Synthetic

<400> SEQUENCE: 3
gtagcagtaa gtgcaacgat                                              20

<210> SEQ ID NO 4
```

```
<211> LENGTH: 20
<212> TYPE: DNA
<213> ORGANISM: Artificial
<220> FEATURE:
<223> OTHER INFORMATION: Synthetic

<400> SEQUENCE: 4
agcacgtaca taagcatcag                                                      20

<210> SEQ ID NO 5
<211> LENGTH: 21
<212> TYPE: DNA
<213> ORGANISM: Artificial
<220> FEATURE:
<223> OTHER INFORMATION: Synthetic

<400> SEQUENCE: 5
cagcactgcc aatggttcca a                                                    21

<210> SEQ ID NO 6
<211> LENGTH: 21
<212> TYPE: DNA
<213> ORGANISM: Artificial
<220> FEATURE:
<223> OTHER INFORMATION: Synthetic

<400> SEQUENCE: 6
gccttaacag tctggttaaa c                                                    21

<210> SEQ ID NO 7
<211> LENGTH: 20
<212> TYPE: DNA
<213> ORGANISM: Artificial
<220> FEATURE:
<223> OTHER INFORMATION: Synthetic

<400> SEQUENCE: 7
tcgcctccaa gaatgtaagt                                                      20

<210> SEQ ID NO 8
<211> LENGTH: 21
<212> TYPE: DNA
<213> ORGANISM: Artificial
<220> FEATURE:
<223> OTHER INFORMATION: Synthetic

<400> SEQUENCE: 8
tctgcatttt aactatggct c                                                    21

<210> SEQ ID NO 9
<211> LENGTH: 21
<212> TYPE: DNA
<213> ORGANISM: Artificial
<220> FEATURE:
<223> OTHER INFORMATION: Synthetic

<400> SEQUENCE: 9
tgactacttt tgacttcagc c                                                    21

<210> SEQ ID NO 10
<211> LENGTH: 22
<212> TYPE: DNA
<213> ORGANISM: Artificial
<220> FEATURE:
<223> OTHER INFORMATION: Synthetic

<400> SEQUENCE: 10
```
aaccattcaa catttttaac cc                                           22

<210> SEQ ID NO 11
<211> LENGTH: 20
<212> TYPE: DNA
<213> ORGANISM: Artificial
<220> FEATURE:
<223> OTHER INFORMATION: Synthetic

<400> SEQUENCE: 11
aaacaggatg cctgccttta                                              20

<210> SEQ ID NO 12
<211> LENGTH: 20
<212> TYPE: DNA
<213> ORGANISM: Artificial
<220> FEATURE:
<223> OTHER INFORMATION: Synthetic

<400> SEQUENCE: 12
ggactttcca cctatgggac                                              20

<210> SEQ ID NO 13
<211> LENGTH: 25
<212> TYPE: DNA
<213> ORGANISM: Artificial
<220> FEATURE:
<223> OTHER INFORMATION: Synthetic

<400> SEQUENCE: 13
agcagataag acagtattac tagtt                                        25

<210> SEQ ID NO 14
<211> LENGTH: 23
<212> TYPE: DNA
<213> ORGANISM: Artificial
<220> FEATURE:
<223> OTHER INFORMATION: Synthetic

<400> SEQUENCE: 14
actcactcta gtgataaatc ggg                                          23

<210> SEQ ID NO 15
<211> LENGTH: 20
<212> TYPE: DNA
<213> ORGANISM: Artificial
<220> FEATURE:
<223> OTHER INFORMATION: Synthetic

<400> SEQUENCE: 15
ggaagaatca aatagacaat                                              20

<210> SEQ ID NO 16
<211> LENGTH: 24
<212> TYPE: DNA
<213> ORGANISM: Artificial
<220> FEATURE:
<223> OTHER INFORMATION: Synthetic

<400> SEQUENCE: 16
gctggccata tatatttta aacc                                          24

<210> SEQ ID NO 17
<211> LENGTH: 20
<212> TYPE: DNA

```
<213> ORGANISM: Artificial
<220> FEATURE:
<223> OTHER INFORMATION: Synthetic

<400> SEQUENCE: 17
ggtgtgcgta tgaagcagtg                                                  20

<210> SEQ ID NO 18
<211> LENGTH: 20
<212> TYPE: DNA
<213> ORGANISM: Artificial
<220> FEATURE:
<223> OTHER INFORMATION: Synthetic

<400> SEQUENCE: 18
gcagtgctaa ccttgcattg                                                  20

<210> SEQ ID NO 19
<211> LENGTH: 20
<212> TYPE: DNA
<213> ORGANISM: Artificial
<220> FEATURE:
<223> OTHER INFORMATION: Synthetic

<400> SEQUENCE: 19
agagactgct gaggagtcca                                                  20

<210> SEQ ID NO 20
<211> LENGTH: 20
<212> TYPE: DNA
<213> ORGANISM: Artificial
<220> FEATURE:
<223> OTHER INFORMATION: Synthetic

<400> SEQUENCE: 20
acaacgtctt ggagcgccag                                                  20

<210> SEQ ID NO 21
<211> LENGTH: 20
<212> TYPE: DNA
<213> ORGANISM: Artificial
<220> FEATURE:
<223> OTHER INFORMATION: Synthetic

<400> SEQUENCE: 21
tttggccagc ataagccatg                                                  20

<210> SEQ ID NO 22
<211> LENGTH: 20
<212> TYPE: DNA
<213> ORGANISM: Artificial
<220> FEATURE:
<223> OTHER INFORMATION: Synthetic

<400> SEQUENCE: 22
gccagcacat ggtttaggag                                                  20

<210> SEQ ID NO 23
<211> LENGTH: 21
<212> TYPE: DNA
<213> ORGANISM: Artificial
<220> FEATURE:
<223> OTHER INFORMATION: Synthetic

<400> SEQUENCE: 23
cgccagttag ctcaatatca t                                                21
```

```
<210> SEQ ID NO 24
<211> LENGTH: 21
<212> TYPE: DNA
<213> ORGANISM: Artificial
<220> FEATURE:
<223> OTHER INFORMATION: Synthetic

<400> SEQUENCE: 24
ccgccagtat gttgtaagaa a                                              21

<210> SEQ ID NO 25
<211> LENGTH: 21
<212> TYPE: DNA
<213> ORGANISM: Artificial
<220> FEATURE:
<223> OTHER INFORMATION: Synthetic

<400> SEQUENCE: 25
ctcagttcca gtacggctcc a                                              21

<210> SEQ ID NO 26
<211> LENGTH: 21
<212> TYPE: DNA
<213> ORGANISM: Artificial
<220> FEATURE:
<223> OTHER INFORMATION: Synthetic

<400> SEQUENCE: 26
cagcactggg tatggttcca a                                              21

<210> SEQ ID NO 27
<211> LENGTH: 21
<212> TYPE: DNA
<213> ORGANISM: Artificial
<220> FEATURE:
<223> OTHER INFORMATION: Synthetic

<400> SEQUENCE: 27
gccttaactc actggttaaa c                                              21

<210> SEQ ID NO 28
<211> LENGTH: 17
<212> TYPE: DNA
<213> ORGANISM: Artificial
<220> FEATURE:
<223> OTHER INFORMATION: Synthetic

<400> SEQUENCE: 28
attcgttgga aacggga                                                   17

<210> SEQ ID NO 29
<211> LENGTH: 11
<212> TYPE: DNA
<213> ORGANISM: Artificial
<220> FEATURE:
<223> OTHER INFORMATION: Synthetic

<400> SEQUENCE: 29
gttagggtta g                                                         11
```

THERAPEUTIC TREATMENT OF MICROSATELLITE UNSTABLE CANCERS

CROSS-REFERENCE TO RELATED APPLICATIONS

This application is a national stage application, filed under 35 U.S.C. § 371, of International Patent Application No. PCT/US19/35130, filed Jun. 3, 2019, entitled "Therapeutic Treatment of Microsatellite Unstable Cancers" and published Dec. 12, 2019 as WO 2019/236448, which claims the benefit of priority under 35 U.S.C. § 119 (e) to U.S. Provisional Application No. 62/680,322, filed on Jun. 4, 2018, entitled, "Therapeutic Treatment of Microsatellite Unstable Cancers" and to U.S. Provisional Application No. 62/853,412, filed on May 28, 2019, entitled, "Therapeutic Treatment of Microsatellite Unstable Cancers". The entire contents of each of these applications are hereby incorporated by reference herein.

FIELD OF THE INVENTION

The invention relates generally to methods, compositions and kits for the identification and treatment of cancers that exhibit microsatellite instability.

BACKGROUND OF THE INVENTION

Microsatellites ("MS(s)") or microsatellite DNA are genomic regions containing tandem sequence repeats. Generally, microsatellites are tracts of variable-length repeats (generally repeated 5-50 times) of short DNA motifs (ranging in length from 1-6 or more base pairs). Microsatellites may encompass a variety of low complexity sequences; however, most MSs are mono- or di-nucleotide repeats. Microsatellites occur at thousands of locations within an organism's genome, which are distributed throughout the genome.

Defects in DNA mismatch repair (MMR) can promote a hyper-mutable state in which cells develop insertion and deletion mutations (indels) at microsatellites. This hyper-mutation, termed microsatellite instability (MSI), has been identified to contribute to the development of certain cancers. Tumor MSI occurs when one or more MS regions have dramatically higher numbers of MS indels. Tumors with MS regions that do not display dramatically higher numbers of MS indels are generally referred to as microsatellite stable ("MSS"). Immunotherapy, specifically immune checkpoint blockade via administration of programmed cell death 1 (PD-1) inhibitors with or without cytotoxic T-lymphocyte-associated protein 4 (CTLA-4) inhibitors, has been identified as effective for certain cancers characterized by MSI. However, a large proportion of patients with MSI cancers do not respond to immunotherapy. A need therefore exists for improved compositions and methods for treating MSI tumors, as well as for treating other forms of cancer.

BRIEF SUMMARY OF THE INVENTION

The current disclosure relates, at least in part, to compositions and methods for the diagnosis and treatment of microsatellite unstable cancers. In particular, the instant disclosure has identified that microsatellite unstable cancers are particularly susceptible to treatment with anti-WRN helicase agents. Without wishing to be bound by theory, the WRN helicase has been newly identified herein as required for preserving DNA integrity and cellular viability of cancers that exhibit microsatellite instability (MSI) and/or impaired mismatch repair (MMR). Classification of a cancer as MSI and/or impaired for MMR therefore identifies anti-WRN helicase agents as preferred therapeutic options for such cancers, in many cases distinct from those treatments previously appreciated for MSI and/or impaired MMR cancer treatment. WRN helicase-targeting agents are additionally contemplated as components of combination therapies for MSI and/or impaired MMR cancers.

In one aspect, the instant disclosure provides a method for selecting a treatment for a subject having or at risk of developing a cancer that exhibits microsatellite instability (MSI) and/or impaired mismatch repair (MMR), the method involving: (a) obtaining a sample from a subject having or at risk of developing a cancer that exhibits MSI and/or impaired MMR; (b) identifying the presence or absence in the sample of MSI and/or impaired MMR; and (c) if the sample exhibits MSI and/or impaired MMR, selecting a WRN inhibitor as a treatment for the subject, thereby selecting a treatment for the subject having or at risk of developing a cancer that exhibits microsatellite instability (MSI) and/or impaired MMR.

In one embodiment, the cancer is an endometrial cancer, a gastric cancer, a colorectal cancer or an ovarian cancer.

In another embodiment, step (b) includes performing a single multiplex PCR reaction that is analyzed by capillary electrophoresis.

Optionally, step (b) includes classifying the sample on the basis of the density of deletions in microsatellite regions and total deletions from whole genome or whole exome data, optionally as compared to available whole genome or whole exome cancer cell line encyclopedia (CCLE) data.

In another embodiment, the WRN inhibitor is distamycin A; netropsin; 3,6,9-trisubstituted acridine; NSC 617145; and/or NSC 19630.

In certain embodiments, the WRN inhibitor is an oligonucleotide inhibitor of WRN, optionally an antisense oligonucleotide, a siRNA and/or a sgRNA. Optionally, the sgRNA is sgWRN1 (GTAAATTGGAAAACCCACGG; SEQ ID NO: 1), sgWRN2 (ATCCTGTGGAACATAC-CATG; SEQ ID NO: 2), sgWRN3 (GTAGCAGTAAGTGCAACGAT; SEQ ID NO: 3), sgWRN-EIJ (AGCACGTACATAAGCATCAG; SEQ ID NO: 4), shWRN1-1 (CAGCACTGCCAATGGTTCCAA; SEQ ID NO: 5) and/or shWRN2-1 (GCCT-TAACAGTCTGGTTAAAC; SEQ ID NO: 6).

In one embodiment, the WRN inhibitor specifically inhibits the helicase activity of WRN.

In some embodiments, the subject has been previously administered an immunotherapy, optionally an immunotherapy that is a programmed cell death 1 (PD-1) inhibitor, optionally with or without a cytotoxic T-lymphocyte-associated protein 4 (CTLA-4) inhibitor.

In one embodiment, the subject has not responded to the immunotherapy. Another embodiment of the methods includes: (d) administering the selected WRN inhibitor to the subject, optionally where a combination therapy that includes the selected WRN inhibitor and a second agent is administered, optionally wherein: the second agent is a small molecule that induces DNA damage and/or modulates a DNA repair pathway, or is a chemotherapeutic agent, and/or is a PARP inhibitor, a CHK1/2 inhibitor and/or a DNA-PKCS inhibitor. Optionally, the small molecule that induces DNA damage and/or modulates a DNA repair pathway is calactin. Optionally, the PARP inhibitor is palbociclib, the CHK1/2 inhibitor is prexasertib and/or the DNA-PKCS inhibitor is NU7441.

In an additional embodiment, identifying step (b) includes use of a kit of the instant claims.

In certain embodiments, the subject is human.

Another aspect of the instant disclosure provides a kit for identifying MSI and/or impaired MMR in a sample and selecting a subject for a WRN inhibitor therapy, with instructions for its use.

In one embodiment, the sample is a tumor sample, optionally an endometrial cancer tumor sample, a gastric cancer tumor sample, a colorectal cancer tumor sample and/or an ovarian cancer tumor sample.

In another embodiment, the kit further includes reagents for performing a single multiplex PCR reaction to detect MSI and/or impaired MMR.

An additional aspect of the instant disclosure provides a method for treating or preventing an endometrial cancer, a gastric cancer, a colorectal cancer and/or an ovarian cancer in a subject having or at risk of developing such a cancer, the method involving: (a) obtaining a sample from a subject having or at risk of developing an endometrial cancer, a gastric cancer, a colorectal cancer and/or an ovarian cancer; (b) identifying the presence or absence in the sample of MSI and/or impaired MMR; and (c) if the sample exhibits MSI and/or impaired MMR, administering a WRN inhibitor to the subject, thereby treating or preventing the endometrial cancer, gastric cancer, colorectal cancer and/or ovarian cancer in the subject having or at risk of developing such a cancer.

Definitions

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value.

In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Unless otherwise clear from context, all numerical values provided herein are modified by the term "about."

The term "administration" refers to introducing a substance into a subject. In general, any route of administration may be utilized including, for example, parenteral (e.g., intravenous), oral, topical, subcutaneous, peritoneal, intraarterial, inhalation, vaginal, rectal, nasal, introduction into the cerebrospinal fluid, or instillation into body compartments. In some embodiments, administration is oral. Additionally or alternatively, in some embodiments, administration is parenteral. In some embodiments, administration is intravenous.

By "agent" is meant any small compound (e.g., small molecule), antibody, nucleic acid molecule, or polypeptide, or fragments thereof or cellular therapeutics such as allogeneic transplantation and/or CART-cell therapy.

The term "cancer" refers to a malignant neoplasm (Stedman's Medical Dictionary, 25th ed.; Hensyl ed.; Williams & Wilkins: Philadelphia, 1990). Exemplary cancers include, but are not limited to, colorectal cancer (e.g., colon cancer, rectal cancer, colorectal adenocarcinoma), endometrial cancer (e.g., uterine cancer, uterine sarcoma), esophageal cancer (e.g., adenocarcinoma of the esophagus, Barrett's adenocarcinoma), gastric cancer (e.g., stomach adenocarcinoma (STAD)), and ovarian cancer (e.g., cystadenocarcinoma, ovarian embryonal carcinoma, ovarian adenocarcinoma), including, e.g., colon adenocarcinoma (COAD), oesophageal carcinoma (ESCA), rectal adenocarcinoma (READ) and uterine corpus endometrial carcinoma (UCEC). Other exemplary forms of cancer include, but are not limited to, diffuse large B-cell lymphoma (DLBCL), as well as the broader class of lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; hematopoietic cancers (e.g., myeloid malignancies (e.g., acute myeloid leukemia (AML) (e.g., B-cell AML, T-cell AML), myelodysplastic syndrome, myeloproliferative neoplasm, chronic myelomonocytic leukemia (CMML) and chronic myelogenous leukemia (CML) (e.g., B-cell CML, T-cell CML)) and lymphocytic leukemia such as acute lymphocytic leukemia (ALL) (e.g., B-cell ALL, T-cell ALL) and chronic lymphocytic leukemia (CLL) (e.g., B-cell CLL, T-cell CLL)); brain cancer (e.g., meningioma, glioblastomas, glioma (e.g., astrocytoma, oligodendroglioma), medulloblastoma); lung cancer (e.g., bronchogenic carcinoma, small cell lung cancer (SCLC), non-small cell lung cancer (NSCLC), adenocarcinoma of the lung); acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); bronchus cancer; carcinoid tumor; cervical cancer (e.g., cervical adenocarcinoma); choriocarcinoma; chordoma; craniopharyngioma; connective tissue cancer; epithelial carcinoma; ependymoma; endotheliosarcoma (e.g., Kaposi's sarcoma, multiple idiopathic hemorrhagic sarcoma); Ewing's sarcoma; ocular cancer (e.g., intraocular melanoma, retinoblastoma); familiar hypereosinophilia; gall bladder cancer; gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis;

kidney cancer (e.g., nephroblastoma a.k.a. Wilms' tumor, renal cell carcinoma); liver cancer (e.g., hepatocellular cancer (HCC), malignant hepatoma); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

By "control" or "reference" is meant a standard of comparison. In one aspect, as used herein, "changed as compared to a control" sample or subject is understood as having a level that is statistically different than a sample from a normal, untreated, or control sample. Control samples include, for example, cells in culture, one or more laboratory test animals, or one or more human subjects. Methods to select and test control samples are within the ability of those in the art. Determination of statistical significance is within the ability of those skilled in the art, e.g., the number of standard deviations from the mean that constitute a positive result.

By "homopolymers(s)" is meant a microsatellite (MS) that is a mononucleotide repeat of at least 6 bases (e.g., a stretch of at least 6 consecutive A, C, T or G residues in the DNA). A "homopolymer region" is a MS region in which the microsatellite is a homopolymer. A "homopolymer subregion" refers to a homopolymer microsatellite located within a larger genomic region (e.g., a homopolymer region).

As used herein, the term "indel" refers to a mutation in a nucleic acid in which one or more nucleotides are either inserted or deleted, resulting in a net gain or loss of nucleotides that can include any combination of insertions and deletions. Aberrant homopolymer lengths often result from indels.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation.

As used herein, "microsatellite (MS)" refers to a genetic locus comprising short (e.g., 1-20), tandemly repeated sequence motifs comprising a minimal total length of about 6 bases. A "mononucleotide microsatellite" or refers to a genetic locus comprising a repeated single nucleotide (e.g., poly-A) and is a specific subclass of MSs. A "dinucleotide microsatellite" refers to a genetic locus comprising a motif of two nucleotides that are tandemly repeated, a "trinucleotide microsatellite" refers to a genetic locus comprising three nucleotides that are tandemly repeated, and a "tetranucleotide microsatellite" refers to a genetic locus comprising a motif of four nucleotides that are tandemly repeated. Additional microsatellite motifs can comprise pentanucleotide and hexanucleotide repeats. A "monomorphic microsatellite" is one in which all (or substantially all) individuals, particularly all individuals of a given population, share the same number of repeat units, which is in contrast to a "polymorphic microsatellite," which is used to refer to microsatellites in which more than about 1% of individuals in a given population display a different number of repeat units in at least of their alleles. When analyzing MS, one may look at genomic DNA of a sample (e.g., genomic DNA of a tumor cell). "Microsatellite region" refers to the genomic context in which a particular microsatellite resides (i.e., the particular genomic region containing the MS).

As used herein, "microsatellite instability (MSI)" refers to a clonal or somatic change in the number of repeated DNA nucleotide units in MSs such as, for example, insertions and deletions (indels). In certain embodiments, the diagnosis of MSI in a subject or sample is based upon assessment of a set of five microsatellite markers (two mononucleotide repeats and three dinucleotide repeats) proposed by the National Cancer Institute Research Workshop in Bethesda (Boland et al. Cancer Res. 58: 5248-57). In such embodiments, if two or greater of these microsatellite regions demonstrate contractions and/or expansions, MSI status is assigned. The term "microsatellite stable (MSS)" refers to MSs that do not display a clonal or somatic change in the number of repeated DNA nucleotide units in the respective MSs. In certain embodiments, MSS status is assigned where none of the five microsatellite markers (two mononucleotide repeats and three dinucleotide repeats) proposed by the National Cancer Institute Research Workshop in Bethesda (Boland et al. Cancer Res. 58: 5248-57) show expansions or contractions. In some embodiments, detecting MSI in a subject, tumor and/or cancer cell sample may include classifying MSI or MSS status in the subject, tumor and/or cancer cell, in which case the method may include a classification step as described herein.

As used herein, the term "next-generation sequencing" or "NGS" can refer to sequencing technologies that have the capacity to sequence polynucleotides at speeds that were unprecedented using conventional sequencing methods (e.g., standard Sanger or Maxam-Gilbert sequencing methods). These unprecedented speeds are achieved by performing and reading out thousands to millions of sequencing reactions in parallel. NGS sequencing platforms include, but are not limited to, the following: Massively Parallel Signature Sequencing (Lynx Therapeutics); 454 pyro-sequencing (454 Life Sciences/Roche Diagnostics); solid-phase, reversible dye-terminator sequencing (Solexa/Illumina); SOLiD technology (Applied Biosystems); Ion semiconductor sequencing (ion Torrent); and DNA nanoball sequencing (Complete Genomics). Descriptions of certain NGS platforms can be found in the following: Shendure, et al., "Next-generation DNA sequencing," Nature, 2008, vol. 26, No. 10, 135-1 145; Mardis, "The impact of next-generation sequencing technology on genetics," Trends in Genetics, 2007, vol. 24, No. 3, pp. 133-141; Su, et al., "Next-generation sequencing and its applications in molecular diagnostics" Expert Rev Mol Diagn, 2011, 11 (3):333-43; and Zhang et al., "The impact of next-generation sequencing on genomics", J Genet Genomics, 201, 38(3): 95-109.

As used herein, the term "subject" includes humans and mammals (e.g., mice, rats, pigs, cats, dogs, and horses). In many embodiments, subjects are mammals, particularly primates, especially humans. In some embodiments, subjects are livestock such as cattle, sheep, goats, cows, swine, and the like; poultry such as chickens, ducks, geese, turkeys, and the like; and domesticated animals particularly pets such as dogs and cats. In some embodiments (e.g., particularly in research contexts) subject mammals will be, for example, rodents (e.g., mice, rats, hamsters), rabbits, primates, or swine such as inbred pigs and the like.

As used herein, the terms "treatment," "treating," "treat" and the like, refer to obtaining a desired pharmacologic and/or physiologic effect. The effect can be prophylactic in terms of completely or partially preventing a disease or symptom thereof and/or can be therapeutic in terms of a partial or complete cure for a disease and/or adverse effect attributable to the disease. "Treatment," as used herein, covers any treatment of a disease or condition in a mammal, particularly in a human, and includes: (a) preventing the disease from occurring in a subject which can be predisposed to the disease but has not yet been diagnosed as having it; (b) inhibiting the disease, i.e., arresting its development; and (c) relieving the disease, i.e., causing regression of the disease.

Unless specifically stated or obvious from context, as used herein, the term "or" is understood to be inclusive. Unless specifically stated or obvious from context, as used herein, the terms "a", "an", and "the" are understood to be singular or plural.

The phrase "pharmaceutically acceptable carrier" is art recognized and includes a pharmaceutically acceptable material, composition or vehicle, suitable for administering compounds of the present disclosure to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. It is also understood that throughout the application, data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

The term "pharmaceutically acceptable salts, esters, amides, and prodrugs" as used herein refers to those carboxylate salts, amino acid addition salts, esters, amides, and prodrugs of the compounds of the present disclosure which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the disclosure.

The term "salts" refers to the relatively non-toxic, inorganic and organic acid addition salts of compounds of the present disclosure. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium, and the like, as well as non-toxic ammonium, tetramethylammonium, tetramethylammonium, methlyamine, dimethylamine, trimethylamine, triethlyamine, ethylamine, and the like. (See, for example, S. M. Barge et al., "Pharmaceutical Salts," J. Pharm. Sci., 1977, 66:1-19 which is incorporated herein by reference).

A "therapeutically effective amount" of an agent described herein is an amount sufficient to provide a therapeutic benefit in the treatment of a condition or to delay or minimize one or more symptoms associated with the condition. A therapeutically effective amount of an agent means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the disclosure will be apparent from the following description of the preferred embodiments thereof, and from the claims. Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All published foreign patents and patent applications cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

The following detailed description, given by way of example, but not intended to limit the disclosure solely to the specific embodiments described, may best be understood in conjunction with the accompanying drawings, in which:

FIG. 1A shows a schematic of the analyses. Cell lines were grouped by feature and dependency scores were analyzed to identify feature-specific genetic dependencies. FIG. 1B shows cell lines plotted by number of deletions and fraction of deletions in MS regions. MSI classification by NGS and multiplex PCR are indicated. FIG. 1C depicts false discovery rate-adjusted Q values (Benjamini-Hochberg method) plotted against the mean difference of dependency scores between MSI and MSS cell lines from projects Achilles (n=32 MSI, 412 MSS) and DRIVE (n=34 MSI, 327 MSS).

FIG. 2A depicts the relative viability of Cas9-expressing cell lines obtained by Cell-Titer Glo, at 8 days after lentiviral transduction with the following sgRNAs: negative controls targeting chromosome 2 intergenic sites (Chr.2-2 sgRNA, Chr.2-4 sgRNA), pan-essential controls (PolR2D sgRNA, Myc sgRNA) and WRN targets (WRN sgRNA 1, WRN sgRNA 2, WRN sgRNA 3). The following cell lines were used: ES2 (ovary, MSS), SW620 (colon, MSS); SW837 (colon, MSS); GCIY (stomach, MSS); HEC50B (endometrium, MSS); OVK18 (ovary, MSI); KM12 (colon, MSI); SW48 (colon, MSI); SNU1 (stomach, MSI); SNGM (endometrium, MSI). P values compare sgRNAs against negative controls (Chr.2-2 sgRNA, Chr.2-4 sgRNA) and were analyzed using two-way analysis of variance (ANOVA) between WRN sgRNAs and negative controls. FIG. 2B shows WRN and GAPDH levels in KM12 cells expressing the indicated WRN cDNA (left immunoblot). WRN(E84A), exonuclease dead mutant; WRN(K577M), helicase-dead mutant; WRN(E84A/K577M), double mutant. The right-hand immunoblot of FIG. 2B shows WRN levels following sgRNA transduction. FIG. 2C shows relative viability 9 days after sgRNA transduction in KM12 cells expressing Cas9 and GFP or the indicated WRN cDNA. P values are from two-tailed Student's t-test for WRN EIJ sgRNA values between mock and indicated WRN cDNA. FIG. 2D shows KM12 xenograft growth with or without doxycycline induction of WRN shRNA 1 or seed control (WRN-C911 shRNA 1). P values were based on the likelihood ratio test comparing growth rates with and without doxycycline. FIG. 2E shows an immunoblot of WRN, γH2AX and GAPDH levels in KM12 xenografts. "Dox" is doxycycline. FIG. 2F shows representative images of CCLF_CORE_0001_T 9 days after shRNA induction relative to no doxycycline treatment. Scale bar is 200 μm. FIG. 2G shows viability of CCLF_CORE_0001_T 9 days after shRNA induction relative to no doxycycline treatment. P values are from two-tailed Student's t-test between WRN shRNA and its corresponding seed control. Data in FIGS. 2A, 2C, 2D and 2G are mean±s.e.m. All experiments were performed three times, except for experiments in FIGS. 2E-2G and FIG. 2D, which were performed twice and once, respectively. In FIG. 2A, n=3, and in FIG. 2C, n=6 biological replicates. In FIG. 2D, n=5 (4 from day 15-18) and 5, 4 and 4 tumors for WRN shRNA 1 without and with doxycycline, WRN-C911 shRNA 1 without and with doxycycline, respectively. In FIG. 2G, n=2 biological replicates with 3 technical replicates each.

FIG. 3A shows enrichment or depletion scores from gene set enrichment analyses in WRN-depleted OVK18 cells plotted against WRN depleted SW48 cells. Signature enrichment plots for hallmark gene sets are shown for WRN-depleted OVK18 and SW48 cells. FIG. 3B shows phosphorylated p53 (S15) immunofluorescence analysis after sgRNA transduction. Scale bar, 50 μm. FIG. 3C shows nuclear phospho-p53 (S15) staining intensity per cell. The lower and upper limits of the boxes represent the 25th and 75th percentiles, respectively; the bar in the middle of the box represents the median value and the whiskers represent the $1^{st}$ and 99th percentiles. Outliers are represented as dots. Mean log(change in intensity) following WRN knockout compared to control sgRNA in MSI versus MSS cells; $P<2\times10^{-16}$, contrast test of least-squares means. Mean fold change (calculated as log (change in intensity)): 0.21 (KM12), 0.10 (SW48), 0.034 (SW620). n indicates the number of cells (treated with Chr.2-2 sgRNA, WRN sgRNA 2, WRN sgRNA 3, respectively) for KM12 (7,080, 14,410, 15,921), SW48 (15,329, 9,491, 13,196), SW620 (27,374, 23,898, 28,808). Representative data from one experiment are shown. All experiments were performed twice, except for experiments in FIG. 3A, which were performed once.

FIG. 4A shows an immunoblot to γH2AX, phospho-CHK2 (T86) and total CHK2, WRN and GAPDH levels following WRN knockout.

Etoposide and hydroxyurea were used to generate DSBs and replication stress, respectively. FIG. 4B shows γH2AX immunofluorescence following sgRNA transduction. Scale bar, 50 μm. FIG. 4C shows nuclear γH2AX staining intensity per cell. The lower and upper limits of the boxes represent the 25th and 75th percentiles, respectively; the bar in the middle of the box represents the median value and the whiskers represent the 1st and 99th percentiles. Outliers are represented as dots. Mean log(change in intensity) following WRN knockout compared to control in MSI compared with MSS cells; $P<2\times10^{-16}$, contrast test of least-squares means. Mean fold change (calculated as log(change in intensity)): 0.39 (KM12), 0.33 (SW48), −0.10 (SW620). n indicates the number of cells (treated with Chr.2-2 sgRNA, WRN sgRNA 2, WRN sgRNA 3, respectively) for KM12 (3,029, 8,880, 6,887), SW48 (13,246, 4,553, 7,216), SW620 (9,071, 5,174, 3,853). FIG. 4D shows telomere PNA-FISH of metaphase spreads with and without doxycycline induction of WRN shRNA 1. Hollow arrowhead indicates chromosomal breaks. Filled arrowheads indicate chromosomal fragments. FIG. 4E shows metaphase spread of the pattern of DNA damage per cell. P values were analyzed by two-tailed Student's t-test for the percentage of cells with DNA damage. FIG. 4F shows the relative viability of HCT 116 with and without MMR restoration 7 days after shRNA transduction. Negative control: RFP shRNA. Pan-essential controls: PSMD2 shRNA, RPS6 shRNA. WRN shRNA: WRN shRNA 1, WRN shRNA 2. Data are mean±s.e.m. (n=6 biological replicates). P values are from two-way ANOVA between WRN shRNAs and RFP shRNA. In FIGS. 4A-4D and FIG. 4F, representative data from one experiment are shown. In FIG. 4E, data from two independent experiments are shown. All experiments were performed twice.

FIG. 5A shows screened cell lines plotted by number of deletions and fraction of deletions occurring in microsatellite (MS) regions. Genes involved in MMR that are lost are indicated by different colors. "None" indicates no predicted loss of MMR genes. "Multiple" indicates loss of more than one MMR gene. "n/a" is not available. FIG. 5B shows, using PCR-based MSI phenotyping, the false discovery rate-adjusted Q values (Benjamini-Hochberg procedure) plotted against the mean difference of dependency scores between MSI and MSS cell lines for Achilles (n=19 MSI; n=291 MSS) and DRIVE (n=23 MSI; n=252 MSS). FIG. 5C shows dependency scores for each RecQ helicase plotted for MSI and MSS cell lines from Achilles and DRIVE (n=as per FIG. 5B. Q values (Wilcoxon rank-sum test) for Achilles/DRIVE are $5.0\times10^{-8}/1.7\times10^{-8}$, 0.73/0.52, 0.73/0.85, 0.25/0.73 and 0.08/not available for WRN, RECQL, BLM, RECQL5 and RECQL4, respectively. Center lines indicate medians. Boxes indicate 25th and 75th percentiles; whiskers extend to 1.5×IQR and individual data points are represented by dots. FIG. 5D shows sensitivity and positive predictive value of indicated relationship between biomarker and genetic dependency. FIG. 5E shows dependency score distributions and associated biomarkers for example biomarker-genetic dependency relationships. Width of colored regions represent density estimates. Horizontal dashed line: threshold used to separate dependent and non-dependent cell lines. n=37, 14, 541 MSI cell lines from typical lineage, MSI cell lines from atypical lineage, MSS cell lines, respectively. n=120/546 KRAS hotspot mutants/other; 65/601 BRAF hotspot mutants/other; 86/580 PIK3CA hotspot mutants/other.

FIG. 6A shows WRN dependency scores plotted by lineage, sub-classified by MSI and MSS status. Boxes indicate 25th and 75th percentiles; whiskers extend to 1.5× IQR and individual data points are represented by dots. FIG. 6B shows microsatellite deletions in cell lines classified as MSS (n=541), MSI from an infrequent MSI lineage (n=45), or MSI from an MSI-predominant lineage (n=54), $*P=1.7\times10^{-9}$, from a Wilcoxon signed-rank test. Width of colored regions represent density estimates. FIG. 6C shows MSI cell lines plotted by their average WRN dependency and number of microsatellite deletions. Lineages are color-coded. FIG. 6D shows MSI cell lines from MSI-predominant lineages plotted by their average WRN dependency and number of microsatellite deletions. Lineages are color-coded.

FIG. 7A shows an immunoblot of WRN and GAPDH levels 4 days after sgRNA transduction. FIG. 7B shows relative viability following sgRNA transduction in a competitive growth assay. Data are mean±s.e.m. (n=6 biological replicates). Comparison between WRN sgRNAs and negative controls at day 10; two-way ANOVA; $*P=0.37$, $\dagger P=1.2\times10^{-7}$, $\ddagger P=0.23$, $\S P=2.7\times10^{-19}$. FIG. 7C shows a clonogenic assay after shRNA transduction with a non-targeting negative control (RFP shRNA (shRFP)), a pan-essential control (PSMD2 shRNA (shPSMD2)) and two shRNAs against WRN (shWRN1 and shWRN2). FIG. 7D shows relative staining intensity of the clonogenic assay. Data are mean±s.e.m. (n=3 technical replicates). Representative data from one experiment are shown. All experiments were performed three times.

FIG. 8A describes the gating strategy employed. For cell cycle analyses (top), debris and dead cells were excluded based on forward scatter-area (FSC-A) and side scatter-area (SSC-A) profiles. Subsequently, singlets were identified based on FSC-A and forward scatter-height (FSCH) profiles. These singlets were then analyzed for DAPI (DNA content) and EdU-Alexa Fluor 647 (EdU-647) staining intensities. EdU+ cells (cells exhibiting higher staining intensity than unstained cells) were classified as 'S phase'. EdU− cells were classified either as 'G1 phase' or 'G2/M phase' based on their DNA content. For apoptosis analyses (bottom), debris was excluded based on FSC-A and SSC-A profiles. The remaining samples were analyzed for annexin-V-FITC and propidium iodide (PI) staining intensities. Subsequently, annexin-V+ cells and PI+ cells (cells exhibiting higher staining intensity than unstained cells) were identified. On the basis of the positivity of these markers, cells were classified into one of the following three categories: viable (annexin-V+PI+), early apoptosis (annexin-V+PI−) and late apoptosis/nonapoptotic death (annexin-V−PI+ and annexin-V+PI+). FIG. 8B demonstrates cell cycle evaluation 4 days after sgRNA transduction. Comparison between Chr.2-2 sgRNA and WRN sgRNAs for the percentage of S-phase cells; two-way ANOVA; $*P=0.16$, $\dagger P=0.67$, $\ddagger P=6.1\times10^{-7}$, $\S P=3.5\times10^{-4}$, $\|P=0.69$, $\P P=2.6\times10^{-6}$. FIG. 8C shows annexin-V and propidium iodide staining evaluating early apoptosis and late apoptosis/non-apoptotic cell death 7 days after sgRNA transduction. Comparison between Chr.2-2 sgRNA and WRN sgRNAs for the percentage of dying/dead cells; two-way ANOVA; $*P=0.10$, $\dagger P=0.41$, $\ddagger P=3.4\times10^{-3}$, $\S P=3.6\times10^{-4}$, $\|P=0.57$, $\P P=3.6\times10^{-5}$. FIG. 8D shows annexin V and propidium iodide staining 4 and 8 days after shRNA transduction. Comparison between RFP shRNA and WRN shRNAs; two-way ANOVA; $1.3 \times 10^{-3}$ (SW837 day 4), $1.6 \times 10^{-2}$ (SW837 day 8), $1.2 \times 10^{-6}$ (KM12 day 4), $4.3 \times 10^{-9}$ (KM12 day 8). Three biological replicates are presented in tandem for FIGS. 8B-8D. Representative data from one experiment are shown. All experiments were performed twice.

FIG. 9A shows phosphorylated p53 (S15) immunofluorescence images following sgRNA transduction in ovarian cell lines (ES2 and OVK18). Scale bar, 50 µm. FIG. 9B shows nuclear phosphorylated p53 (S15) staining intensity per cell following WRN knockout compared to control sgRNA. Data were analyzed as fold change (log(WRN sgRNA/control sgRNA)); mean=0.059 (OVK18), mean=−0.037 (ES2). Difference in fold change between OVK18 and ES2; contrast test of least-squares means; $P<2\times10^{-16}$. n indicates the number of cells treated with Chr.2-2 sgRNA, WRN sgRNA 2, WRN sgRNA 3, respectively, for OVK18 (3,982, 1,143, 2,740) and ES2 (4,916, 3,072, 3,690). FIG. 9C shows p21 immunofluorescence images following sgRNA transduction in colon cell lines (SW620, KM12 and SW48). KM12 is a p53-impaired MSI cell line. Scale bar, 50 µm. FIG. 9D shows nuclear p21 staining per cell. Data were analyzed as fold change (log (WRN sgRNA/control sgRNA)); WRN knockout compared to control in SW48 cells was compared to either SW620 ($P<2\times10^{-16}$; contrast test of least-squares means) or KM12 cells ($P<2\times10^{-16}$; contrast test of least-squares means). Mean=0.13 (SW48), mean=−0.016 (SW620), mean=−0.032 (KM12). n indicates the number of cells analyzed following treatment with Chr.2-2 sgRNA, WRN sgRNA 2, WRN sgRNA 3, respectively, for SW48 (16,203, 7,617, 13,257), SW620 (7,278, 13,768, 11,576) and KM12 (16,117, 14,200, 11,301). FIG. 9E shows p21 immunofluorescence images following sgRNA transduction in ovarian cell lines. Scale bar, 50 µm. FIG. 9F shows nuclear p21 staining intensity per cell. Data were analyzed as fold change (log(WRN sgRNA/ control sgRNA)); WRN knockout compared to control in OVK18 cells was compared to ES2 cells using contrast test of least-squares means; $P<2\times10^{-16}$. Mean=0.157 (OVK18), mean=−0.010 (ES2). n indicates the number of cells analyzed following treatment with Chr.2-2 sgRNA, WRN sgRNA 2, WRN sgRNA 3, respectively, for OVK18 (3,436, 5,876, 8,275) and ES2 (9,117, 6,834, 11,576). FIG. 9G shows WRN dependency for cells lines classified as MSS (n=514), MSI from an infrequent MSI lineage (n=6 and 8 for p53-intact and -impaired), or MSI from an MSI-predominant lineage (n=23 and 13 for p53-intact and -impaired) and further subclassified by p53 status. In FIGS. 9B, 9D and 9F, the center line indicates the median, boxes indicate the 25 to 75th percentiles, whiskers indicate the 1st to 99th percentiles and dots indicate outliers. In FIG. 9G, boxes indicate 25th and 75th percentiles; whiskers extend to 1.5×IQR and individual data points are represented by dots. Representative data from one experiment are shown. For FIGS. 9A-9F, experiments were performed twice.

FIG. 10A shows nuclear γH2AX foci per cell following sgRNA transduction in colon cell lines. FIG. 10B shows γH2AX immunofluorescence images following sgRNA transduction in ovarian cell lines. Scale bar, 50 µm. FIG. 10C shows nuclear γH2AX staining intensity per cell following sgRNA transduction. Difference in fold change between OVK18 and ES2; contrast test of least squares mean; $P<2\times10^{-16}$. Mean=0.147 (OVK18) and mean=0.055 (ES2). n indicates the number of cells analyzed following treatment with Chr.2-2 sgRNA, WRN sgRNA 2, WRN sgRNA 3, respectively, for OVK18 (2,612, 4,823, 6,164) and ES2 (6,429, 6,469, 6,388). Center line indicates the median, boxes indicate the 25 to 75th percentiles, whiskers indicate the 1st to 99th percentiles and dots indicate outliers. FIG. 10D shows nuclear γH2AX foci per cell following sgRNA transduction in ovarian cell lines. FIG. 10E shows fluorescence of Apple-53BP1 foci in colon cell lines exogenously expressing Apple-53BP1(truncated). Scale bar, 50 µm. FIG. 10F shows nuclear Apple-53BP1 foci per cell following sgRNA transduction in colon cell lines. FIG. 10G shows fluorescence of Apple-53BP1 foci following sgRNA transduction in ovarian cell lines exogenously expressing Apple-53BP1(truncated). Scale bar, 50 µm. FIG. 10H shows nuclear Apple-53BP1 foci per cell in ovarian cell lines. Representative data from one experiment are shown. All experiments were performed twice.

FIG. 11A shows phospho-ATM (S1981) immunofluorescence images following sgRNA transduction in colon cell lines. Scale bar, 50 µm. FIG. 11B shows nuclear phospho-ATM (S1981) foci per cell following sgRNA transduction in colon cell lines. FIG. 11C shows phospho-ATM (S1981) immunofluorescence images following sgRNA transduction in ovarian cell lines. Scale bar, 50 µm. FIG. 11D shows nuclear phospho-ATM (S1981) foci per cell following sgRNA transduction in ovarian cell lines. FIG. 11E shows γH2AX, phospho-CHK2(T68), total CHK2, WRN and GAPDH levels following shRNA transduction. Representative data from one experiment are shown. All experiments were performed twice.

FIG. 12A shows telomere PNA-FISH of metaphase spreads with or without doxycycline induction of WRN shRNA 1. Hollow arrowhead, chromosomal breaks. Filled arrowhead, chromosomal fragments. FIG. 12B shows WRN immunofluorescence images following treatment with WRN shRNA 1 or control shRNA (WRN-C911 shRNA). FIG. 12C shows WRN immunofluorescence images. Scale bar, 20 µm. FIG. 12D shows analyses of WRN co-localization with the nucleolar marker, fibrillarin, by Pearson's co-localization coefficients. Data are mean±s.e.m. (n=5 biological replicates); two-tailed Student's t-test; *$P=1.0\times10^{-3}$, †$P=4.3\times10^{-5}$, ‡$P=0.014$. Representative data from one experiment are shown. All experiments were conducted twice.

FIG. 13A shows the estimated association between WRN dependency and MSI status after controlling for loss of indicated genes (effect size estimates for the linear model are plotted against significance). If loss of a gene can fully account for the MSI-WRN relationship, the difference in dependency and significance would be 0. Genes for which the loss are typically associated with insertion and deletion (indel) mutations (over half of loss events) are highlighted in red. n=51 MSI, n=541 MSS. FIG. 13B shows the average WRN dependency score for MSS and MSI lines stratified by POLE status (n=4, 5, 35, 497, 2, 12, 5, 10, 22 cell lines per category in order of left to right). Boxes indicate 25th and 75th percentiles; whiskers extend to 1.5×IQR and individual data points are represented by dots.

FIG. 14A shows the results of a flow-cytometric host-cell reactivation assay measuring the ability of the indicated cell lines to repair a G:G mismatch in a plasmid reporter, thus activating the fluorescence reporter and measuring MMR activity. Data are mean±s.e.m. from three independent experiments; two-tailed Student's t-test, *$P=5.5\times10^{-2}$, †$P=2.3\times10^{-3}$; two-way ANOVA, $P=3.6\times10^{-8}$. FIG. 14B shows an immunoblot of γH2AX, WRN, MLH1, MSH3 and GAPDH levels following shRNA transduction in HCT116 cells with or without MMR restoration. FIG. 14C shows the relative viability of HCT116 derivatives 7 days after sgRNA transduction. Data are mean±s.e.m. (n=6 biological replicates); two-way ANOVA; $P=5.7\times10^{-20}$ (* compared to †), $P=3.3\times10^{-12}$ († compared to ‡), $P=1.6\times10^{-16}$ († compared to §). FIG. 14D shows an immunoblot of γH2AX, WRN, MLH1, MSH3 and GAPDH levels following shRNA transduction in HCT116 derivatives.

FIG. 14E shows a clonogenic assay after shRNA transduction for 15 days. FIG. 14F shows the relative staining intensity of the clonogenic assay. Data are mean±s.e.m. (n=3 biological replicates); two-way ANOVA; $P=3.6\times10^{-6}$ (* compared to t), $P=8.5\times10^{-8}$ († compared to ‡), $P=2.8\times10^{-8}$ († compared to §). For FIGS. 14B-14F, representative data from one experiment are shown. All experiments were conducted twice except for those in FIG. 14 A, which were conducted three times.

DETAILED DESCRIPTION OF THE INVENTION

Figure 1A:
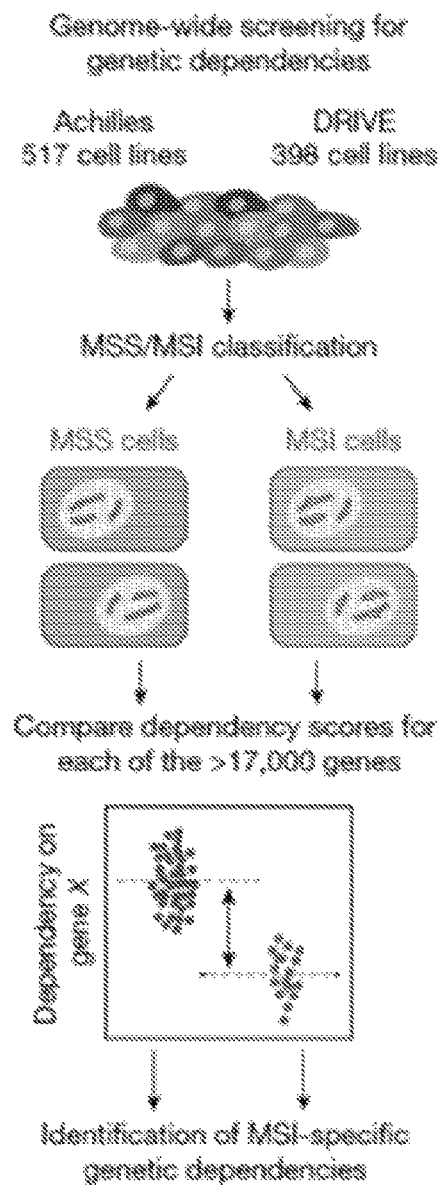
FIGS. 1A to 1C demonstrate the genome-scale functional genomic screening performed herein to identify synthetic lethal genes in MSI cells.

The present disclosure is directed, at least in part, to the discovery that cancers that exhibit microsatellite instability (MSI) require the WRN helicase to preserve DNA integrity and cellular viability. As such, the WRN helicase is herein identified as a therapeutic target for MSI and/or impaired MMR cancers, and WRN inhibitory agents are specifically discovered as an effective therapeutic selection for cancers that exhibit MSI and/or impaired MMR. Compositions and methods for identification of an MSI and/or impaired MMR cancer and selection of a therapeutic that includes a WRN inhibitory agent (either as a single therapeutic or as a component of a combination therapy) are described in additional detail below.

Defects in DNA mismatch repair (MMR) can promote a hyper-mutable state in which cells develop insertion and deletion mutations (indels) at nucleotide-repeat regions termed microsatellites (Vilar and Gruber. Nature reviews. Clinical oncology. 7: 153-162). This class of hypermutations, termed microsatellite instability (MSI), contributes to the development of several cancers, predominantly in colon (15%) (4), gastric (22%) (5), endometrial (20-30%) (6), and ovarian (12%) (7) cancers. MSI and/or impaired MMR cancers can arise due to germline defects in the MMR genes MSH2, MSH6, PMS2, or MLH1 via a condition known as Lynch Syndrome (4). More commonly, MSI and/or impaired MMR cancers arise after somatic inactivation of a MMR gene, typically MLH1 loss via promoter hypermethylation (4). In recent years, the clinical implications of MSI status has grown, owing to the success of immunotherapy, specifically immune checkpoint blockade with programmed cell death 1 (PD-1) inhibitors with or without cytotoxic T-lymphocyte-associated protein 4 (CTLA-4) inhibitors, in these cancers. Although MSI has been associated with notable responses to immune checkpoint blockade, 45-60% of patients with MSI cancers do not respond to immunotherapy, and use of these immune checkpoint blockade agents can be limited by their toxicity (8, 9).

Synthetic lethality is an interaction between two genetic events through which the co-occurrence of these two genetic events leads to cell death, but each event alone does not. In some instances, identification of a synthetic lethality can be exploited for cancer therapeutics (1). DNA repair processes have been previously described to represent attractive synthetic lethal targets, because many cancers exhibit an impairment of a DNA repair pathway, which leads to dependence on specific repair proteins (2). The success of poly(ADP-ribose) polymerase 1 (PARP-1) inhibitors in cancers that exhibit deficiencies in homologous recombination has highlighted the potential of this approach (3).

Within the instant disclosure, data from large-scale silencing screens that employ CRISPR-Cas9-mediated knockout and RNA interference have been analyzed, and it was strikingly identified that the RecQ DNA helicase WRN was selectively essential in MSI models in vitro and in vivo, yet dispensable in models of cancers that are microsatellite stable. Consistent with this observation, WRN depletion induced double-strand DNA breaks and promoted both cell cycle arrest and apoptosis selectively in MSI models. MSI cancer models specifically required the helicase activity, but not the exonuclease activity of WRN. These findings have therefore identified WRN as a synthetic lethal vulnerability and promising drug target in MSI cancers. In particular, the administration of a WRN inhibitor, either alone or in combination with another agent, is contemplated as a treatment specifically for a patient specifically identified as having or at risk of developing a MSI cancer.

Identification of MSI and/or Impaired AIR in a Tissue and/or Cancer

Identification of a tissue, tumor and/or cancer of a subject as exhibiting MSI and/or impaired MMR can be performed by any method available in the art. Certain methods and compositions described herein relate to identification of a cancer as exhibiting MSI and/or impaired MMR, the presence of which is based upon an assessment of a sample for the presence of indels at microsatellites. As noted elsewhere herein, an exemplary clinical MSI assay can be performed via a single multiplex PCR reaction that is analyzed by capillary electrophoresis (Boland et al. Cancer Research. 58: 5248). Whole genome sequencing (or sequencing of a subset of the genome, optionally with emphasis upon sequencing of microsatellites) can also be used to identify MSI and/or impaired MMR in a subject, tissue, tumor and/or cancer. As noted herein, recently published MSI annotations have been used to classify cell lines on next generation sequencing analysis of the total number of genetic deletions and fraction of deletions located within microsatellite regions as described in Phase II of the Cancer Cell Line Encyclopedia (CCLE) project, employed as a proxy for assessment of MSI vs. MSS status.

In certain aspects, the instant disclosure provides methods and kits that involve and/or allow for assessment of the presence or absence of one or more MSI indicators. In particular embodiments, a subject, tissue, cell and/or sample is assessed for one or more variants and/or sites of MSI within genomic microsatellite regions.

MSI/Impaired MMR Cancers

As noted herein, certain cancers have been identified in which MSI and/or impaired MMR is relatively more prevalent than for other cancer types. Such cancers for which MSI and/or impaired MMR is prevalent include endometrial cancers, gastric cancers, colorectal cancers and ovarian cancers. Consideration of MSI and/or impaired MMR prevalence within such cancer populations is detailed below and elsewhere herein.

Colorectal Cancer (CRC)

CRC is the third most common cancer type in which about 1.4 million new cases are diagnosed each year. Additionally, CRC results in about 700,000 deaths per year. Unfortunately, the frequency of CRC appears to be increasing throughout the developed world, presumably due to increased risk of CRC associated with alcohol consumption, smoking, obesity, diabetes, the consumption of large amounts of meat, and little physical activity.

About 15% are associated with microsatellite instability (MSI), which can be defined as somatic changes in the length of microsatellites. Based on microsatellite status (e.g., MSI versus MSS), colorectal tumors can be divided into 3 the categories: 1. tumors with high levels of microsatellite instability (MSI-H), 2. tumors with low levels of microsatellite instability (MSI-L), and tumors that are microsatellite stable (MSS).

Lynch syndrome is a hereditary form of autosomal dominant colon cancer that results from inherited mismatch repair gene defects and is characterized by high levels of microsatellite instability and constitutes about 20% of MSI-H CRCs. Lynch Syndrome patients typically display initial cancer onset in their mid-forties, which is in sharp contrast to patients with sporadic MSI-H cancers where the average age is over seventy.

Sporadic MSI-H tumors are usually caused by the epigenetic silencing of MLH1 caused by promoter methylation. Traditionally, Lynch Syndrome tumors our thought to arise from adenomas, while sporadic MSI-H CRCs are believed to arise from serrated polyps. Approximately 80% of MSI-H tumors are sporadic tumors. Sporadic MSI-H tumors are generally predisposed to present in the proximal colon and are more common in women than men.

With respect to CRC, it is therefore clear that the ability to accurately assess MSI status, and then provide a directed treatment (e.g., via selection and administration of a WRN inhibitor, either alone or in combination with an additional therapy) is important because it can define hereditary forms of CRC and inform clinical care.

Other exemplary MSI cancers include, but are not limited to, adenocarcinoma (COAD), stomach adenocarcinoma (STAD), and uterine corpus endometrial carcinoma (UCEC).

Amplification and Sequencing Oligonucleotides

In some aspects, WGS or exome sequencing may be performed upon a test sample for purpose of detecting variants and/or copy number variation as described herein and identifying MSI classification and/or impaired MMR and selecting a therapy (e.g., selecting a WRN inhibitor as a therapy). In certain embodiments, assessment of candidate and/or test MSI and/or impaired MMR neoplasia or tumor samples can be performed using one or more amplification and/or sequencing oligonucleotides flanking variant sequence and/or copy number variation regions. Design and use of such amplification and sequencing oligonucleotides, and/or copy number detection probes/oligonucleotides, can be performed by one of ordinary skill in the art.

As will be appreciated by one of ordinary skill in the art, any such amplification sequencing and/or copy number detection oligonucleotides can be modified by any of a number of art-recognized moieties and/or exogenous sequences, e.g., to enhance the processes of amplification, sequencing reactions and/or detection. Exemplary oligonucleotide modifications that are expressly contemplated for use with the oligonucleotides of the instant disclosure include, e.g., fluorescent and/or radioactive label modifications; labeling one or more oligonucleotides with a universal amplification sequence (optionally of exogenous origin) and/or labeling one or more oligonucleotides of the instant disclosure with a unique identification sequence (e.g., a "bar-code" sequence, optionally of exogenous origin), as well as other modifications known in the art and suitable for use with oligonucleotides.

In certain embodiments, five clinically relevant MSI regions (as proposed by the National Cancer Institute Research Workshop in Bethesda (Boland et al. Cancer Res. 58: 5248-57)) are queried to ascertain MSI status of a sample. These five microsatellite markers (two mononucleotide repeats and three dinucleotide repeats) are D2S123, D5S346, D17S250, BAT 25, and BAT 26. Exemplary amplification primers for assessing these microsatellite marker regions are shown in Table 1 below (reproduced from Losso et al. ABCD, arq. bras. cir. dig. vol. 25 no. 4 São Paulo October/December 2012), within which the BAT25 forward primer (5'-TCGCCTCCAAGAATGTAAGT-3') is SEQ ID NO: 7; the BAT25 reverse primer (5'-TCTGCATTTTAAC-TATGGCTC-3') is SEQ ID NO: 8; the BAT26 forward primer (5'-TGACTACTTTTGACTTCAGCC-3') is SEQ ID NO: 9; the BAT26 reverse primer (5'-AACCATTCAACAT-TTTTAACCC-3') is SEQ ID NO: 10; the D2S123 forward primer (5'-AAACAGGATGCCTGCCTTTA-3') is SEQ ID NO: 11; the D2S123 reverse primer (5'-GGACTTTCCACC-TATGGGAC-3') is SEQ ID NO: 12; the D5S346 forward primer (5'-AGCAGATAAGACAGTATTACTAGTT-3') is SEQ ID NO: 13; the D5S346 reverse primer (5'-ACT-CACTCTAGTGATAAATCGGG-3') is SEQ ID NO: 14; the D17S250 forward primer (5'-GGAAGAATCAAATA-GACAAT-3') is SEQ ID NO: 15; and the D17S250 reverse primer (5'-GCTGGCCATATATATATTTAAACC-3') is SEQ ID NO: 16.

TABLE 1

Microsatellite Markers BAT 25, BAT 26, D2S123, D5S346 and D17S250

| Microssatélite | Location | Size | Forward Primer | Reverse Primer |
|---|---|---|---|---|
| BAT25 | gene c-Kit cr. 4q12 | 110-130 pb | 5'-TCG CCT CCA AGA ATG TAA GT-3' | 5'-TCT GCA TTT TAA CTA TGG CTC-3' |
| BAT26 | gene hMSH2 cr. 2p | 100-120 pb | 5'-TGA CTA CTT TTG ACT TCA GCC-3' | 5'-AAC CAT TCA ACA TTT TTA ACC C-3' |
| D2S123 | gene hMSH2 cr. 2p | 200-230 pb | 5'-AAA CAG GAT GCC TGC CTT TA-3' | 5'-GGA CTT TCC ACC TAT GGG AC-3' |
| D5S346 | gene APC cr. 5q21q22 | 100-130 pb | 5'-AGC AGA TAA GAC AGT ATT ACT AGT T-3' | 5'-ACT CAC TCT AGT GAT AAA TCG GG-3' |

TABLE 1-continued

Microsatellite Markers BAT 25, BAT 26, D2S123, D5S346 and D17S250

| Microssatélite | Location | Size | Forward Primer | Reverse Primer |
|---|---|---|---|---|
| D17S250(Mfd15CA) | gene BRCA1 cr.17q11.2-q12 | 140-170 pb | 5'-GGA AGA ATC AAA TAGACA AT-3' | 5'-GCT GGC CAT ATA TAT ATT TAA ACC-3' |

Treatment Selection

The methods described herein can be used for selecting, and then optionally administering, an optimal treatment (e.g., a WRN inhibitor) for a subject. Thus, the methods described herein include methods for the treatment of cancer, particularly neoplasia or tumors associated with MSI and/or impaired MMR. Generally, the methods include administering a therapeutically effective amount of a treatment as described herein, to a subject who is in need of, or who has been determined to be in need of, such treatment.

As used in this context, to "treat" means to ameliorate at least one symptom of the cancer. For example, a treatment can result in a reduction in tumor size, tumor growth, cancer cell number, cancer cell growth, or metastasis or risk of metastasis.

For example, the methods can include selecting and/or administering a treatment that includes a therapeutically effective amount of a WRN inhibitor. A WRN inhibitor of the instant disclosure may be administered alone to a subject, or, optionally, a WRN inhibitor may be administered in combination with an additional therapeutic agent (e.g., an immune checkpoint blocker such as, for example, cytotoxic T-lymphocyte antigen-4 (CTLA-4) and/or programmed death-1 (PD-1), to a subject having a select MSI and/or impaired MMR tumor or cancer/tumor). In certain embodiments, a WRN inhibitor may be administered to a subject in which an immune checkpoint blocker such as CTLA-4 and/or PD-1 has failed to treat, ameliorate and/or cure a MSI- and/or impaired MMR-presenting cancer.

Exemplary WRN inhibitors include the following:

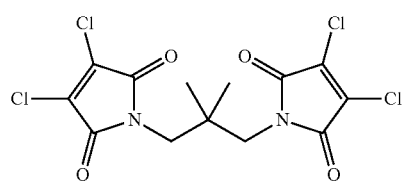

NSC 617145

(see, e.g., Aggarwal et al. Cell Cycle. 12: 3329-35)

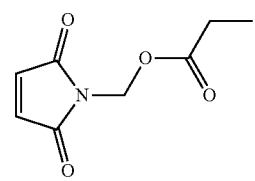

NSC 19630

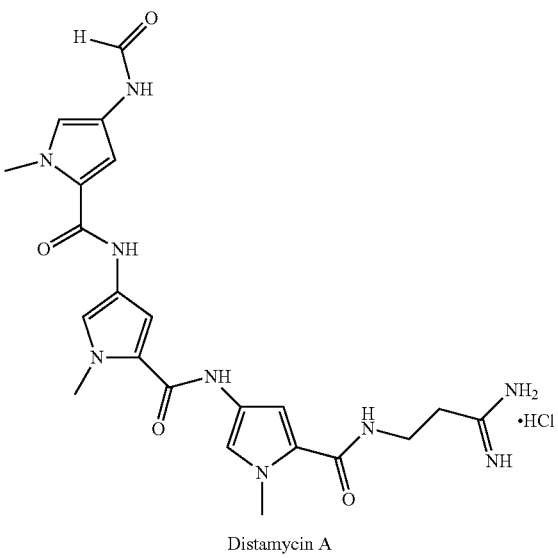

Distamycin A

Distamycin A

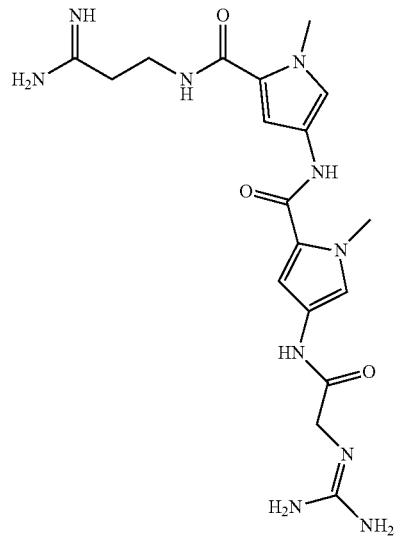

Netropsin

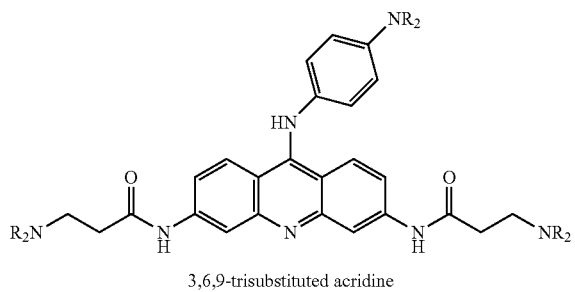

3,6,9-trisubstituted acridine

Oligonucleotide inhibitors of WRN are also explicitly contemplated for use herein, including, e.g., antisense oligonucleotides, dsNA agents (including, e.g., siRNAs, hairpin oligonucleotides, etc.), and sgRNA (e.g., implementing CRISPR/Cas9 as a delivery approach for sequence-specific inhibition of WRN). In certain embodiments, sequence-specific oligonucleotide inhibitors of WRN are delivered as naked oligonucleotides, as modified oligonucleotides (e.g., as GalNAc conjugates), within lipid nanoparticles (LNPs), or as components of other art-recognized delivery modalities for oligonucleotide therapeutics. Exemplary description of oligonucleotide inhibitors of WRN can be found, e.g., in European Patent Application No. 2434009 and/or in U.S. Pat. No. 6,448,080. In certain embodiments, exemplary WRN inhibitor compositions may be given in combination with chemotherapy or ionizing radiation, or with a small molecule that induces DNA damage and/or modulates a DNA repair pathway. An exemplary WRN inhibitor may be an oligonucleotide inhibitor of WRN, which may have at least 33% nucleotide sequence identity with (TTAGGG)n, wherein n=1 to 20. An exemplary WRN inhibitor may be an oligonucleotide inhibitor of WRN, which may have at least 50% nucleotide sequence identity with (TTAGGG)n, wherein n=1 to 20. From about zero to about ten of the first 3'-nucleotide linkages may be hydrolyzable by a 3' to 5' nuclease. An exemplary oligonucleotide WRN inhibitor may be an oligonucleotide with at least about 33% to about 100% or at least 50% to about 100% nucleotide sequence identity with (TTAGGG)n, wherein n is from about 1 to about 20. As used herein, "(TTAGGG)n", when used in the context of a comparison of nucleic sequence identity, refers to a reference nucleic acid. Sequence identity is calculated by performing an alignment of the oligonucleotide and the reference nucleic acid and dividing (a) the number of identical nucleotides in the alignment, by (b) the total number of base pairs of the oligonucleotide. For example, the oligonucleotide may be 11-bp with the sequence GTTAGGGTTAG (SEQ ID NO: 29) which has >91% sequence identity with (TTAGGG)$_2$. An exemplary oligonucleotide WRN inhibitor may be of a form including, but not limited to, single-stranded, double-stranded, or a combination thereof. The oligonucleotide optionally comprises a single-stranded 3'-end of from about 2 to about 2000 nucleotides, optionally from about 2 to about 200 nucleotides. The oligonucleotide may also be an EST. Also specifically contemplated is an analog, derivative, fragment, homolog or variant of the oligonucleotide. Compositions of the present invention may be formulated as a liposome preparation. The liposome preparation can comprise liposomes which penetrate the cells of interest or the stratum corneum, and fuse with the cell membrane, resulting in delivery of the contents of the liposome into the cell. For example, liposomes such as those described in U.S. Pat. No. 5,077,211 of Yarosh, U.S. Pat. No. 4,621,023 of Redziniak et al. or U.S. Pat. No. 4,508,703 of Redziniak et al. can be used. Other suitable formulations can employ niosomes. Niosomes are lipid vesicles similar to liposomes, with membranes consisting largely of non-ionic lipids, some forms of which are effective for transporting compounds across the stratum corneum.

Exemplary antisense or other oligonucleotide-directed inhibition of WRN expression can be assayed in a variety of ways known in the art. For example, WRN mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+mRNA. Methods of RNA isolation are taught in, for example, Ausubel, F. M. et al., Current Protocols in Molecular Biology, Volume 1, pp. 4.1.1-4.2.9 and 4.5.1-4.5.3, John Wiley & Sons, Inc., 1993. Northern blot analysis is routine in the art and is taught in, for example, Ausubel, F. M. et al., Current Protocols in Molecular Biology, Volume 1, pp. 4.2.1-4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Protein levels of WRN can be quantitated in a variety of ways well known in the art, such as immunoprecipitation, Western blot analysis (immunoblotting), ELISA or fluorescence-activated cell sorting (FACS). Antibodies directed to WRN can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., Current Protocols in Molecular Biology, Volume 2, pp. 11.12.1-11.12.9, John Wiley & Sons, Inc., 1997. Preparation of monoclonal antibodies is taught in, for example, Ausubel, F. M. et al., Current Protocols in Molecular Biology, Volume 2, pp. 11.4.1-11.11.5, John Wiley & Sons, Inc., 1997.

Immunoprecipitation methods are standard in the art and can be found at, for example, Ausubel, F. M. et al., Current Protocols in Molecular Biology, Volume 2, pp. 10.16.1-10.16.11, John Wiley & Sons, Inc., 1998. Western blot (immunoblot) analysis is standard in the art and can be found at, for example, Ausubel, F. M. et al., Current Protocols in Molecular Biology, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., Current Protocols in Molecular Biology, Volume 2, pp. 11.2.1-11.2.22, John Wiley & Sons, Inc., 1991

Monoclonal and polyclonal antibodies against RecQ helicase family members, such as WRN helicase, have also been described in the art (see, e.g., U.S. Pat. No. 8,809,296). Compounds of the present invention that suppress WRN helicase gene expression or the function (activity) of a protein encoded by that gene may be natural or synthetic compounds. Typically, the compounds can be produced, obtained or isolated using methods known to those skilled in the art. Such compounds include, for example, compounds comprising a single molecule, such as organic compounds, inorganic compounds, nucleic acids, proteins, peptides, and sugars; and libraries of compounds, expression products of gene libraries, cell extracts, cell culture supernatants, the products of fermenting microorganisms, marine organism extracts, plant extracts, and compounds purified or isolated from such extracts.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The compositions can be administered from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of a WRN inhibitor which achieves a half-maximal inhibition of symptoms) as determined in cell culture. Such information can be used to more accurately determine useful doses in humans. Levels in plasma may be measured, for example, by high performance liquid chromatography.

Combination Treatments

The compositions and methods of the present disclosure may be used in the context of a number of therapeutic or prophylactic applications. In order to increase the effectiveness of a treatment with the compositions of the present disclosure, e.g., a WRN inhibitor selected and/or administered as a single agent, or to augment the efficacy of another therapy (second therapy), it may be desirable to combine these compositions and methods with one another, or with other agents and methods effective in the treatment, amelioration, or prevention of diseases and pathologic conditions, for example, MSI- and/or impaired MMR-exhibiting cancers, e.g., an MSI- and/or impaired MMR-presenting endometrial cancer, an MSI- and/or impaired MMR-presenting gastric cancer, an MSI- and/or impaired MMR-presenting colorectal cancer and/or an MSI- and/or impaired MMR-presenting ovarian cancer.

Administration of a composition of the present disclosure to a subject will follow general protocols for the administration described herein, and the general protocols for the administration of a particular secondary therapy will also be followed, taking into account the toxicity, if any, of the treatment. It is expected that the treatment cycles would be repeated as necessary. It also is contemplated that various standard therapies may be applied in combination with the described therapies.

Pharmaceutical Compositions

Agents of the present disclosure can be incorporated into a variety of formulations for therapeutic use (e.g., by administration) or in the manufacture of a medicament (e.g., for treating or preventing an MSI- and/or impaired MMR-presenting cancer) by combining the agents with appropriate pharmaceutically acceptable carriers or diluents, and may be formulated into preparations in solid, semi-solid, liquid or gaseous forms. Examples of such formulations include, without limitation, tablets, capsules, powders, granules, ointments, solutions, suppositories, injections, inhalants, gels, microspheres, and aerosols.

Pharmaceutical compositions can include, depending on the formulation desired, pharmaceutically-acceptable, non-toxic carriers of diluents, which are vehicles commonly used to formulate pharmaceutical compositions for animal or human administration. The diluent is selected so as not to affect the biological activity of the combination. Examples of such diluents include, without limitation, distilled water, buffered water, physiological saline, PBS, Ringer's solution, dextrose solution, and Hank's solution. A pharmaceutical composition or formulation of the present disclosure can further include other carriers, adjuvants, or non-toxic, non-therapeutic, nonimmunogenic stabilizers, excipients and the like. The compositions can also include additional substances to approximate physiological conditions, such as pH adjusting and buffering agents, toxicity adjusting agents, wetting agents and detergents.

Further examples of formulations that are suitable for various types of administration can be found in Remington's Pharmaceutical Sciences, Mace Publishing Company, Philadelphia, PA, 17th ed. (1985). For a brief review of methods for drug delivery, see, Langer, Science 249: 1527-1533 (1990).

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink.

Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in J Pharmaceutical Sciences 66 (1977):1-19, incorporated herein by reference. The salts can be prepared in situ during the final isolation and purification of the compounds of the application, or separately by reacting a free base or free acid function with a suitable reagent, as described generally below. For example, a free base function can be reacted with a suitable acid. Furthermore, where the compounds to be administered of the application carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Additionally, as used herein, the term "pharmaceutically acceptable ester" refers to esters that hydrolyze in vivo and include those that break down readily in the human body to leave the parent compound (e.g., an FDA-approved compound where administered to a human subject) or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

Furthermore, the term "pharmaceutically acceptable prodrugs" as used herein refers to those prodrugs of the certain compounds of the present application which are, within the scope of sound medical judgment, suitable for use in contact with the issues of humans and lower animals with undue toxicity, irritation, allergic response, and the like, commensurate with a reasonable benefit/risk ratio, and effective for their intended use, as well as the zwitterionic forms, where possible, of the compounds of the application. The term "prodrug" refers to compounds that are rapidly transformed in vivo to yield the parent compound of an agent of the instant disclosure, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, (1987), both of which are incorporated herein by reference.

The components used to formulate the pharmaceutical compositions are preferably of high purity and are substantially free of potentially harmful contaminants (e.g., at least National Food (NF) grade, generally at least analytical grade, and more typically at least pharmaceutical grade) Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

Formulations may be optimized for retention and stabilization in a subject and/or tissue of a subject, e.g., to prevent rapid clearance of a formulation by the subject. Stabilization techniques include cross-linking, multimerizing, or linking to groups such as polyethylene glycol, polyacrylamide, neutral protein carriers, etc. in order to achieve an increase in molecular weight.

Other strategies for increasing retention include the entrapment of the agent, such as a WRN inhibitor, in a biodegradable or bioerodible implant. The rate of release of the therapeutically active agent is controlled by the rate of transport through the polymeric matrix, and the biodegradation of the implant. The transport of drug through the polymer barrier will also be affected by compound solubility, polymer hydrophilicity, extent of polymer cross-linking, expansion of the polymer upon water absorption so as to make the polymer barrier more permeable to the drug, geometry of the implant, and the like. The implants are of dimensions commensurate with the size and shape of the region selected as the site of implantation. Implants may be particles, sheets, patches, plaques, fibers, microcapsules and the like and may be of any size or shape compatible with the selected site of insertion.

The implants may be monolithic, i.e. having the active agent homogenously distributed through the polymeric matrix, or encapsulated, where a reservoir of active agent is encapsulated by the polymeric matrix. The selection of the polymeric composition to be employed will vary with the site of administration, the desired period of treatment, patient tolerance, the nature of the disease to be treated and the like. Characteristics of the polymers will include biodegradability at the site of implantation, compatibility with the agent of interest, ease of encapsulation, a half-life in the physiological environment.

Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers will be condensation polymers. The polymers may be cross-linked or non-cross-linked. Of particular interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. By employing the L-lactate or D-lactate, a slowly biodegrading polymer is achieved, while degradation is substantially enhanced with the racemate. Copolymers of glycolic and lactic acid are of particular interest, where the rate of biodegradation is controlled by the ratio of glycolic to lactic acid. The most rapidly degraded copolymer has roughly equal amounts of glycolic and lactic acid, where either homopolymer is more resistant to degradation. The ratio of glycolic acid to lactic acid will also affect the brittleness of in the implant, where a more flexible implant is desirable for larger geometries Among the polysaccharides of interest are calcium alginate, and functionalized celluloses, particularly carboxymethylcellulose esters characterized by being water insoluble, a molecular weight of about 5 kD to 500 kD, etc. Biodegradable hydrogels may also be employed in the implants of the individual instant disclosure. Hydrogels are typically a copolymer material, characterized by the ability to imbibe a liquid. Exemplary biodegradable hydrogels which may be employed are described in Heller in: Hydrogels in Medicine and Pharmacy, N. A. Peppes ed., Vol. I, CRC Press, Boca Raton, Fla., 1987, pp 137-149.

Pharmaceutical Dosages

Pharmaceutical compositions of the present disclosure containing an agent described herein may be used (e.g., administered to an individual, such as a human individual, in need of treatment with a WRN inhibitor) in accord with known methods, such as oral administration, intravenous administration as a bolus or by continuous infusion over a period of time, by intramuscular, intraperitoneal, intracerobrospinal, intracranial, intraspinal, subcutaneous, intraarticular, intrasynovial, intrathecal, topical, or inhalation routes.

Dosages and desired drug concentration of pharmaceutical compositions of the present disclosure may vary depending on the particular use envisioned. The determination of the appropriate dosage or route of administration is well within the skill of an ordinary artisan. Animal experiments provide reliable guidance for the determination of effective doses for human therapy. Interspecies scaling of effective doses can be performed following the principles described in Mordenti, J. and Chappell, W. "The Use of Interspecies Scaling in Toxicokinetics," In Toxicokinetics and New Drug Development, Yacobi et al., Eds, Pergamon Press, New York 1989, pp. 42-46.

For in vivo administration of any of the agents of the present disclosure, normal dosage amounts may vary from about 10 ng/kg up to about 100 mg/kg of an individual's and/or subject's body weight or more per day, depending upon the route of administration. In some embodiments, the dose amount is about 1 mg/kg/day to 10 mg/kg/day. For repeated administrations over several days or longer, depending on the severity of the disease, disorder, or condition to be treated, the treatment is sustained until a desired suppression of symptoms is achieved.

An effective amount of an agent of the instant disclosure may vary, e.g., from about 0.001 mg/kg to about 1000 mg/kg or more in one or more dose administrations for one or several days (depending on the mode of administration). In certain embodiments, the effective amount per dose varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg.

An exemplary dosing regimen may include administering an initial dose of an agent of the disclosure of about 200 µg/kg, followed by a weekly maintenance dose of about 100 µg/kg every other week. Other dosage regimens may be useful, depending on the pattern of pharmacokinetic decay that the physician wishes to achieve. For example, dosing an individual from one to twenty-one times a week is contemplated herein. In certain embodiments, dosing ranging from about 3 µg/kg to about 2 mg/kg (such as about 3 µg/kg, about 10 µg/kg, about 30 µg/kg, about 100 µg/kg, about 300 µg/kg, about 1 mg/kg, or about 2 mg/kg) may be used. In certain embodiments, dosing frequency is three times per day, twice per day, once per day, once every other day, once weekly, once every two weeks, once every four weeks, once every five weeks, once every six weeks, once every seven weeks, once every eight weeks, once every nine weeks, once every ten weeks, or once monthly, once every two months, once every three months, or longer. Progress of the therapy is easily monitored by conventional techniques and assays. The dosing regimen, including the agent(s) administered, can vary over time independently of the dose used.

Pharmaceutical compositions described herein can be prepared by any method known in the art of pharmacology. In general, such preparatory methods include the steps of bringing the agent or compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, Poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® IL, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, chamomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of an agent (e.g., a WRN inhibitor) described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more of the additional ingredients described herein. Other ophthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Drugs provided herein can be formulated in dosage unit form for ease of administration and uniformity of dosage. It will be understood, however, that the total daily usage of the agents described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincident with the specific active ingredient employed; and like factors well known in the medical arts.

The agents and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the agent or pharmaceutical composition described herein is suitable for topical administration to the eye of a subject.

The exact amount of an agent required to achieve an effective amount will vary from subject to subject, depending, for example, on species, age, and general condition of a subject, severity of the side effects or disorder, identity of the particular agent, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of an agent (e.g., a WRN inhibitor) described herein.

As noted elsewhere herein, a drug of the instant disclosure may be administered via a number of routes of administration, including but not limited to: subcutaneous, intravenous, intrathecal, intramuscular, intranasal, oral, transepidermal, parenteral, by inhalation, or intracerebroventricular.

The term "injection" or "injectable" as used herein refers to a bolus injection (administration of a discrete amount of an agent for raising its concentration in a bodily fluid), slow bolus injection over several minutes, or prolonged infusion, or several consecutive injections/infusions that are given at spaced apart intervals.

In some embodiments of the present disclosure, a formulation as herein defined is administered to the subject by bolus administration.

A drug or other therapy of the instant disclosure is administered to the subject in an amount sufficient to achieve a desired effect at a desired site (e.g., reduction of cancer size, cancer cell abundance, symptoms, etc.) determined by a skilled clinician to be effective. In some embodiments of the disclosure, the agent is administered at least once a year. In other embodiments of the disclosure, the agent is administered at least once a day. In other embodiments of the disclosure, the agent is administered at least once a week. In some embodiments of the disclosure, the agent is administered at least once a month.

Additional exemplary doses for administration of an agent of the disclosure to a subject include, but are not limited to, the following: 1-20 mg/kg/day, 2-15 mg/kg/day, 5-12 mg/kg/day, 10 mg/kg/day, 1-500 mg/kg/day, 2-250 mg/kg/day, 5-150 mg/kg/day, 20-125 mg/kg/day, 50-120 mg/kg/day, 100 mg/kg/day, at least 10 µg/kg/day, at least 100 µg/kg/day, at least 250 µg/kg/day, at least 500 µg/kg/day, at least 1 mg/kg/day, at least 2 mg/kg/day, at least 5 mg/kg/day, at least 10 mg/kg/day, at least 20 mg/kg/day, at least 50 mg/kg/day, at least 75 mg/kg/day, at least 100 mg/kg/day, at least 200 mg/kg/day, at least 500 mg/kg/day, at least 1 g/kg/day, and a therapeutically effective dose that is less than 500 mg/kg/day, less than 200 mg/kg/day, less than 100 mg/kg/day, less than 50 mg/kg/day, less than 20 mg/kg/day, less than 10 mg/kg/day, less than 5 mg/kg/day, less than 2 mg/kg/day, less than 1 mg/kg/day, less than 500 µg/kg/day, and less than 500 µg/kg/day.

In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of an agent (e.g., a WRN inhibitor) described herein. In certain embodiments, a dose described herein includes independently between 1 mg and 3 mg, inclusive, of an agent (e.g., a WRN inhibitor) described herein. In certain embodiments, a dose described herein includes independently between 3 mg and 10 mg, inclusive, of an agent (e.g., a WRN inhibitor) described herein. In certain embodiments, a dose described herein includes independently between 10 mg and 30 mg, inclusive, of an agent (e.g., a WRN inhibitor) described herein. In certain embodiments, a dose described herein includes independently between 30 mg and 100 mg, inclusive, of an agent (e.g., a WRN inhibitor) described herein.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult. In certain embodiments, a dose described herein is a dose to an adult human whose body weight is 70 kg.

It will be also appreciated that an agent (e.g., a WRN inhibitor) or composition, as described herein, can be administered in combination with one or more additional pharmaceutical agents (e.g., therapeutically and/or prophylactically active agents), which are different from the agent or composition and may be useful as, e.g., combination therapies.

Combination therapies explicitly contemplated for the instant disclosure include, e.g., administration of a WRN inhibitor with a small molecule that induces DNA damage and/or modulates a DNA repair pathway, and/or administration of a WRN inhibitor with an immunotherapy and/or chemotherapeutic agent. An exemplary small molecule that induces DNA damage is calactin, which has the following structure:

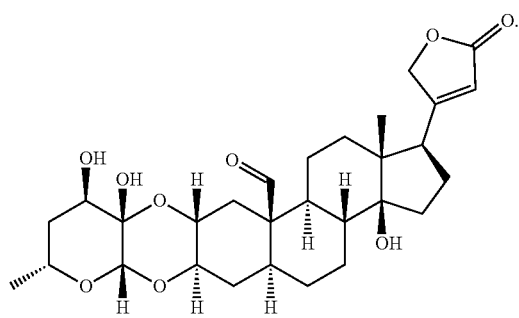

Other such agents that induce DNA damage and/or modulate a DNA repair pathway are also contemplated as combination therapies with WRN inhibitors, as are immunotherapy agents and/or chemotherapeutic agents as described elsewhere herein.

Additional combination therapies explicitly contemplated for the instant disclosure include, e.g., administration of a WRN inhibitor with one or more PARP inhibitors (such as palbociclib), CHK1/2 inhibitors (such as prexasertib), DNA-PKCS inhibitors (such as NU7441), as it is likely that additive effects can be obtained by modulating DNA repair pathways in combination with administration of one or more WRN inhibitors. The exemplary PARP inhibitor palbociclib has the following structure:

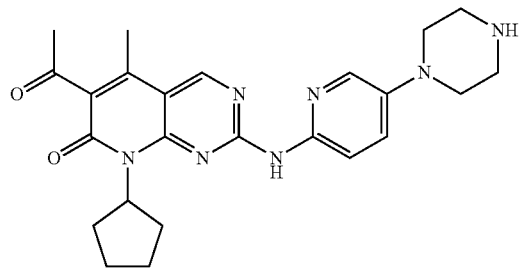 [SMILES: CC(=O)c1c(C)c2cnc(Nc3ccc(N4CCNCC4)cn3)nc2n(C2CCCC2)c1=O]

The exemplary CHK1/2 inhibitor prexasertib has the following structure:

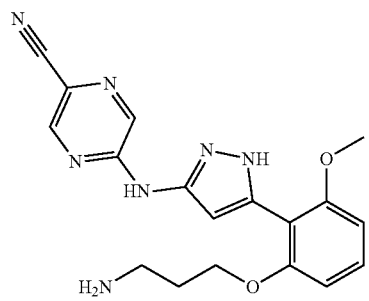 [SMILES: COc1cccc(OCCCN)c1-c1cc(Nc2cnc(C#N)cn2)n[nH]1]

The exemplary DNA-PKCS inhibitor NU7441 has the following structure:

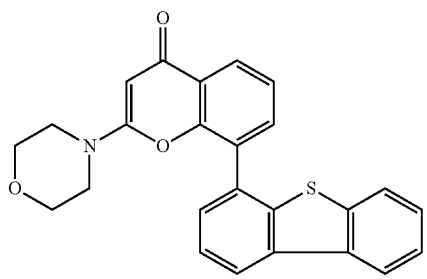 [SMILES: O=c1cc(N2CCOCC2)oc2c(-c3cccc4c3sc3ccccc34)cccc12]

The agents or compositions can be administered in combination with additional pharmaceutical agents that improve their activity (e.g., activity (e.g., potency and/or efficacy) in treating a disease (e.g., an MSI- and/or impaired MMR-exhibiting cancer) in a subject in need thereof, in preventing a disease in a subject in need thereof, in reducing the risk of developing a disease in a subject in need thereof, in inhibiting the replication of a virus, in killing a virus, etc. in a subject or cell. In certain embodiments, a pharmaceutical composition described herein including an agent (e.g., a WRN inhibitor) described herein and an additional pharmaceutical agent shows a synergistic effect that is absent in a pharmaceutical composition including one of the agent and the additional pharmaceutical agent, but not both.

In some embodiments of the disclosure, a therapeutic agent distinct from a first therapeutic agent of the disclosure is administered prior to, in combination with, at the same time, or after administration of the agent of the disclosure. In some embodiments, the second therapeutic agent is selected from the group consisting of a chemotherapeutic, an immunotherapy (e.g., an agent for immune checkpoint blockade such as a PD-1 inhibitor, optionally with or without one or more CTLA-4 inhibitors), an antioxidant, an antiinflammatory agent, an antimicrobial, a steroid, etc.

The agent or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease described herein. Each additional pharmaceutical agent may be administered at a dose and/or on a time schedule determined for that pharmaceutical agent. The additional pharmaceutical agents may also be administered together with each other and/or with the agent or composition described herein in a single dose or administered separately in different doses. The particular combination to employ in a regimen will take into account compatibility of the agent described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, additional WRN inhibitors, other anti-cancer agents, immunotherapy and/or immunomodulatory agents, anti-proliferative agents, cytotoxic agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, and pain-relieving agents. In certain embodiments, the additional pharmaceutical agent is an anti-proliferative agent. In certain embodiments, the additional pharmaceutical agent is an anti-cancer agent. In certain embodiments, the additional pharmaceutical agent is an anti-viral agent. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine kinase inhibitors), modulators of protein stability (e.g., proteasome inhibitors), Hsp90 inhibitors, glucocorticoids, all-trans retinoic acids, and other agents that promote differentiation. In certain embodiments, the agents described herein or pharmaceutical compositions can be administered in combination with an anti-cancer therapy including, but not limited to, surgery, radiation therapy, transplantation (e.g., stem cell transplantation, bone marrow transplantation), immunotherapy, and chemotherapy.

Dosages for a particular agent of the instant disclosure may be determined empirically in individuals who have been given one or more administrations of the agent.

Administration of an agent of the present disclosure can be continuous or intermittent, depending, for example, on the recipient's physiological condition, whether the purpose of the administration is therapeutic or prophylactic, and other factors known to skilled practitioners. The administration of an agent may be essentially continuous over a preselected period of time or may be in a series of spaced doses.

Guidance regarding particular dosages and methods of delivery is provided in the literature, see, for example, U.S. Pat. Nos. 4,657,760; 5,206,344: or 5,225,212. It is within the scope of the instant disclosure that different formulations will be effective for different treatments and different disorders, and that administration intended to treat a specific organ or tissue may necessitate delivery in a manner different from that to another organ or tissue. Moreover, dosages may be administered by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

Kits

The instant disclosure also provides kits containing agents of this disclosure for use in the methods of the present disclosure. Kits of the instant disclosure may include one or more containers comprising an agent (e.g., a WRN inhibitor) of this disclosure and/or may contain agents (e.g., oligonucleotide primers, probes, etc.) for identifying a cancer or subject as possessing one or more microsatellite instabilities (i.e., exhibiting MSI and/or impaired MMR). In some embodiments, the kits further include instructions for use in accordance with the methods of this disclosure. In some embodiments, these instructions comprise a description of administration of the agent to treat or diagnose, e.g., an MSI- and/or impaired MMR-exhibiting cancer, according to any of the methods of this disclosure. In some embodiments, the instructions comprise a description of how to detect an MSI- and/or impaired MMR-exhibiting class of cancer, for example in an individual, in a tissue sample, or in a cell. The kit may further comprise a description of selecting an individual suitable for treatment based on identifying whether that subject has an MSI- and/or impaired MMR-exhibiting cancer.

The instructions generally include information as to dosage, dosing schedule, and route of administration for the intended treatment. The containers may be unit doses, bulk packages (e.g., multi-dose packages) or sub-unit doses. Instructions supplied in the kits of the instant disclosure are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, e.g., a class of MSI- and/or impaired MMR-exhibiting cancer, in a subject. Instructions may be provided for practicing any of the methods described herein.

The kits of this disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump A kit may have a sterile access port (for example the container may be an intravenous solution bag or a vial having a stopper pierceable by a hypodermic injection needle). The container may also have a sterile access port (e.g., the container may be an intravenous solution bag or a vial having a stopper pierceable by a hypodermic injection needle). In certain embodiments, at least one active agent in the composition is a WRN inhibitor. The container may further comprise a second pharmaceutically active agent.

Kits may optionally provide additional components such as buffers and interpretive information. Normally, the kit comprises a container and a label or package insert(s) on or associated with the container.

The practice of the present disclosure employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, Molecular Cloning (Cold Spring Harbor Laboratory Press, Cold Spring Harbor, N.Y.); Sambrook et al., 1989, Molecular Cloning, 2nd Ed. (Cold Spring Harbor Laboratory Press, Cold Spring Harbor, N.Y.); Sambrook and Russell, 2001, Molecular Cloning, 3rd Ed. (Cold Spring Harbor Laboratory Press, Cold Spring Harbor, N.Y.); Ausubel et al., 1992), Current Protocols in Molecular Biology (John Wiley & Sons, including periodic updates); Glover, 1985, DNA Cloning (IRL Press, Oxford); Anand, 1992; Guthrie and Fink, 1991; Harlow and Lane, 1988, Antibodies, (Cold Spring Harbor Laboratory Press, Cold Spring Harbor, N.Y.); Jakoby and Pastan, 1979; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Riott, Essential Immunology, 6th Edition, Blackwell Scientific Publications, Oxford, 1988; Hogan et al., Manipulating the Mouse Embryo, (Cold Spring Harbor Laboratory Press, Cold Spring Harbor, N.Y., 1986); Westerfield, M., The zebrafish book. A guide for the laboratory use of zebrafish (*Danio rerio*), (4th Ed., Univ. of Oregon Press, Eugene, 2000).

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Reference will now be made in detail to exemplary embodiments of the disclosure. While the disclosure will be described in conjunction with the exemplary embodiments, it will be understood that it is not intended to limit the disclosure to those embodiments. To the contrary, it is intended to cover alternatives, modifications, and equivalents as may be included within the spirit and scope of the disclosure as defined by the appended claims. Standard techniques well known in the art or the techniques specifically described below were utilized.

EXAMPLES

Example 1: Materials and Methods

Genetic Dependency Data

CRISPR dependency data were taken from the 18Q4 Avana dataset (31). These data contain gene dependencies estimated for each gene and cell line using the CERES algorithm (10). RNA interference (RNAi) dependency data were derived from project DRIVE (Novartis®) (11) and were reprocessed using the DEMETER2 algorithm (32), which can be downloaded from the DEMETER2 figshare repo (33). For some analyses (for example, FIGS. 5E, 6C, 6D, 9G, 13B), aggregate WRN dependency scores were computed for each cell line by averaging together RNAi and CRISPR dependency scores (which are both normalized so that the median score of pan-essential genes is set at −1) (10, 34). For FIGS. 5C, 6A, 9G, 13B, the lower and upper parts of the boxes correspond to first and third quartiles (25th and 75th percentiles). The upper and lower whiskers extend to the largest and smallest value within 1.5× the interquartile range (IQR) from the box. Gene dependency scores are normalized such that a value of 0 represents the median dependency score of negative control genes and −1 represents the median dependency score of sgRNAs that target pan-essential genes.

Genomics Data

Cancer cell line genomic data used in the analysis, including gene level mRNA expression, gene-level relative copy number and mutation calls, were taken from the DepMap 18Q4 data release (12, 34). Protein abundance data of reverse phase protein arrays (RPPA) were taken from the Cancer Cell Line Encyclopedia (CCLE) (10, 12, 34). All cell line omics data can be downloaded at DepMap (www.depmap.org/portal/).

Cell Line Annotations

Annotations of primary disease site for each cell line can be found in the DepMap 18Q4 data release. The functional status of TP53 in 966 cell lines was annotated based on a combination of the nutlin-3 sensitivity of the cell lines (Genomics of Drug Sensitivity in Cancer; www.cancerrxgene.org) and Cancer Target Discovery and Development (CTD2—www.ocg.cancer.gov/programs/ctd2/data-portal) data sets, along with a p53 target gene expression signature computed from CCLE data (35).

Microsatellite Classification

MSI classifications were obtained from phase II of the CCLE project (12). These classifications were based on the total number of deletions detected in each cell line, and the fraction of deletions in microsatellite regions, using several different data sources (CCLE whole-exome sequencing, CCLE whole-genome sequencing, CCLE hybrid capture and Sanger whole-exome sequencing datasets). These features were then used to classify each cell line as MSI, MSS or indeterminate. Unless otherwise indicated, the instant analysis excluded cell lines classified as indeterminate. When plotting the number of microsatellite deletions and fraction of deletions in microsatellite regions (FIGS. 1B and 6A), these values were averaged across the data sources available for each cell line after normalizing for systematic differences between data sources. Specifically, linear regression models were employed to estimate and remove scale and offset differences between data sources so that the normalized number of deletions (and number of deletions in microsatellite regions) measured in each data source was equal on average. These normalized average numbers of microsatellite deletions and fraction of deletions in microsatellite regions are provided in Table 2 of priority document U.S. Ser. No. 62/853,412.

MMR Status

MMR status was determined based on omics data for the genes MSH2, MSH6, MLH1 and PMS2. For each gene, a determination of whether it was mutated (any detected mutation classified as deleterious), deleted (relative log 2(-copy number)<-1) or lowly expressed (log 2(mRNA expression in transcripts per million)<1) was performed. A gene was classified as inactivated if any of the above criteria were met, and cell lines in which any of these MMR genes were inactivated were classified as having 'MMR loss'. The MMR status for cell lines for which neither gene expression nor copy number data were available were classified as 'N/A'. In addition, MSI cell lines were annotated as having low protein expression of MSH2 and MSH6 if they had protein levels <-1 in the RPPA data (Table 2 of priority document U.S. Ser. No. 62/853,412). However, RPPA data were not used for calling MMR loss, as RPPA data were missing for many cell lines, and MMR loss was detectable from other omics data in most cases. The mutation status of POLE was also classified for all cell lines as 'damaging', 'hotspot missense' or 'other' using the 'Variant_Annotation' column of the CCLE mutation file.

Differential Dependency Analysis

Genes that were preferentially dependent in MSI compared to MSS cell lines were identified using two-group comparisons performed in parallel across genes using the R package Limma (36). The difference in mean dependency was estimated between MSS and MSI cell lines for each gene, and associated P values were derived from empirical-Bayes moderated t-statistics. Q values were computed using the Benjamini-Hochberg method (37).

Dependency and Biomarker Analysis

To compute the predictability of gene dependencies from different biomarkers, each cell line was first called as dependent or not, by thresholding the average of the CRISPR- and RNAi-based dependency scores at a value of -0.5. The positive predictive value and sensitivity were then computed for each biomarker-dependency relationship. WRN dependency was predicted using MSI status either across all cell lines or within common-MSI lineages only. For comparison analyses, equivalent analysis was performed on several canonical biomarker-dependency relationships: KRAS dependency was predicted by KRAS hotspot missense mutations, BRAF dependency was predicted by BRAF hotspot missense mutations, MDM2 dependency was predicted by TP53 wild-type versus mutant status (including damaging, hotspot missense and other non-silent mutations), PIK3CA dependency was predicted by PIK3CA hotspot missense mutations, ERBB2 dependency was predicted by ERBB2 amplification (log 2(relative copy number)>2), NRAS dependency was predicted by NRAS hotspot missense mutations and CTNNB1 dependency was predicted by APC damaging mutations.

Assessing Potential WRN Synthetic Lethality

Figure 13A:
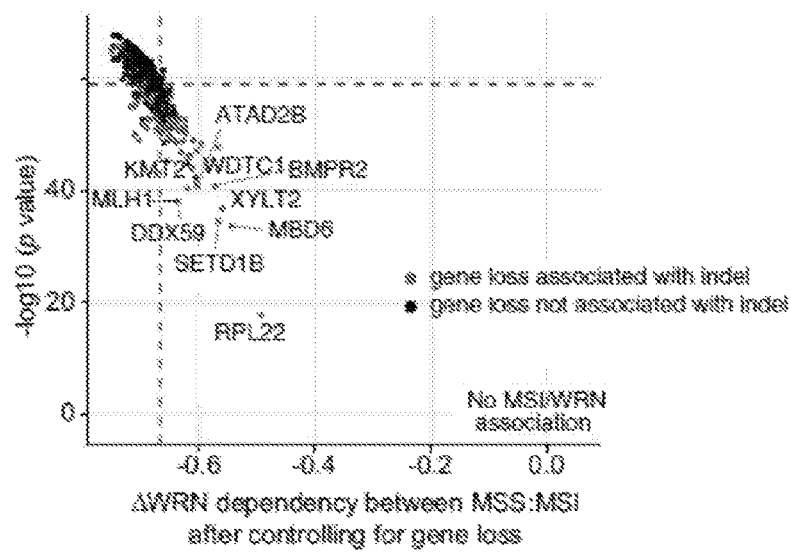
FIGS. 13A and 13B demonstrate that paralog dependencies and hypermutation alone cannot explain the WRN-MSI relationship.
Figure 13B:
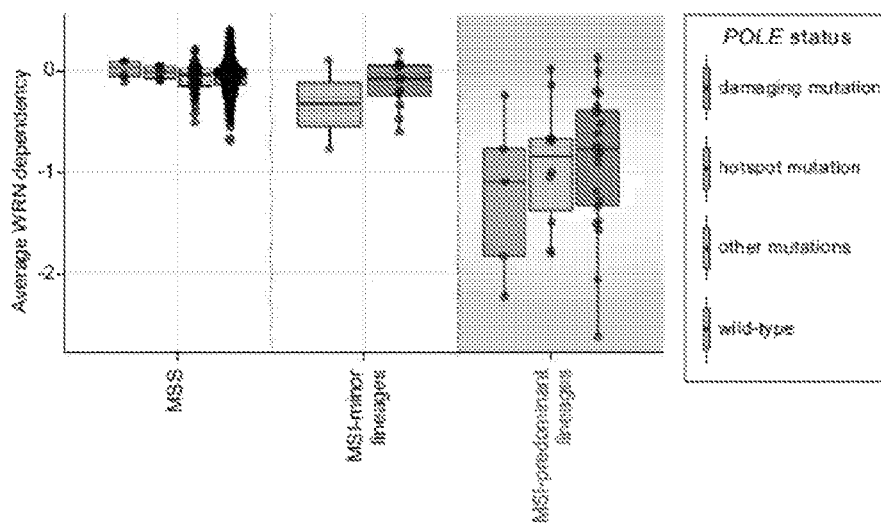

To assess whether loss of function of any particular gene could account for WRN dependency, the functional status of each gene (loss or not) was determined in the same way as described above for MMR gene loss. For each gene, a linear regression model was then used to assess the contribution of both MSI status and loss of the gene to predicting WRN dependency (average of CRISPR and RNAi dependency scores). In FIG. 13A, the linear model coefficients, and associated P values, were plotted for MSI status accounting for loss of each gene.

mRNA Sequencing

Cas-9 expressing cells (SW48 and OVK18) were lentivirally transduced with the following sgRNAs: Chr.2-2 sgRNA, WRN sgRNA 2 and WRN sgRNA 3 (sequences provided below). Cells were selected with puromycin and RNA was purified 72 h after transduction. This was performed in duplicate before cDNA library preparation and subsequent RNA sequencing using the Illumina® NextSeq 500 performed by the Molecular Biology Core Facilities at the Dana-Farber Cancer Institute (DFCI). This experiment was performed once with two biological replicates.

Differential Expression Analysis

First, genes which exhibited fewer than 1 counts per million in more than half of the samples were excluded. The weighted trimmed mean of M-values (38) method was used to normalize the library size of each sample, using the calcNormFactors function from the R package edgeR (39). To estimate the log-fold change (LFC) effect of WRN knockout on each gene in each cell line, the R package Limma (36) was used. Specifically, a linear model was fit for the expression of each gene, using cell line and sgRNA (WRN versus control) as covariates. Read count data were transformed using the Limma function 'voom' prior to model fitting, in order to model the mean-variance relationship of the log(counts) data (40). Fold change effect sizes and empirical-Bayes-moderated t-statistics were then extracted for the WRN knockout effect for each gene and cell line. Gene set enrichment analysis (GSEA) (41) was run to test for gene sets that were up- or down-regulated in each cell line after WRN knockout. In particular, the R package fgsea (42) was used to estimate normalized enrichment statistics, and associated p-values, for each gene set in the Hallmark Collection from the Molecular Signatures Database (43). The GSEA algorithm was run using t-statistics as the gene-level statistics, 1 million random permutations for each cell line tested, and a "GSEA parameter" of 1.

Cell Lines and Reagents

ES2, OVK18, SW620, SW837, KM12, SW48, GCIY, SNU1, HEC50B and SNGM cell lines were collected by the CCLE before distribution for current use. The sources of the aforementioned cell lines can be found in DepMap and are as follows. The ES2, SW620, SW837, SNU1 and SW48 cell lines were originally obtained from the American Type Culture Collection (ATCC). The KM12 cell line was originally obtained from an academic laboratory and can be obtained as part of the NCI-60 cell lines. The GCIY and OVK18 cell lines were originally obtained from the RIKEN Cell Bank. The SNGM and HEC50B cell lines were originally obtained from the Health Science Research Resources Bank. Their identities were confirmed by SNP microarray. The HCT116 cell line and its various derivatives were provided by C. R. Boland, A. Goel and M. Koi (22). The aforementioned cell lines can be obtained from their respective sources. All cell lines were grown in medium supplemented with 10% fetal bovine serum (FBS), penicillin (100 µg ml$^{-1}$)-streptomycin (100 µg ml$^{-1}$)-1-glutamine (292 µg ml$^{-1}$; Gibco) unless otherwise stated. KM12, SW48, SW837, ES2, and SNU1 cells were cultured in RPMI-1640 (Gibco); OVK18 cells were cultured in MEMα; GCIY cells were cultured in MEMα supplemented with 15% FBS; SW620 cells were cultured in Leibovitz's L-15 (Gibco); SNGM cells were cultured in Ham's F12 with 20% FBS (Gibco); HEC50B cells were cultured in EMEM (ATCC) supplemented with 15% FBS; HCT116 cells were cultured in McCoy's 5A (Gibco). Stable *Streptococcus pyogenes* Cas9-expressing cell lines generated by lentiviral transduction of the pXPR_BRD111 construct were from project Achilles (10). pXPR_BRD111 is available from Addgene (plasmid 78166).

CCLF_CORE_0001_T was obtained from a 58-year-old female patient with stage II MSI-H (determined by loss of MLH1 and PMS2 with MLH1 promoter methylation using immunohistochemistry). All samples were obtained with informed consents of the patients at the DFCI. All procedures were conducted under a protocol approved by the DFCI Institutional Review Board. Samples were collected by translational research staff and labelled with a unique identifier before samples were processed and analyzed in the laboratory. Per the protocol, the link to protected health information was maintained within a database with access limited to select research staff. Samples were handled according to the medical ethical guidelines described by the Dana-Farber/Harvard Cancer Center Office for Human Research Studies. Patient tumor resections were placed in a sterile conical tube containing DMEM medium (Thermo Fisher Scientific, 11995073) with 10% FBS (Sigma-Aldrich, F8317), 1% penicillin-streptomycin (Thermo Fisher Scientific, 15140163), 10 μg ml$^{-1}$ of gentamicin and 250 ng ml$^{-1}$ fungizone on wet ice during transport from the operating room to the research laboratory. Resections were placed in a 15-ml conical flask with 5 ml DMEM medium, 10% FBS, 1% penicillin-streptomycin and the digestion enzymes regular collagenase 1 ml (StemCell, 07912) and dispase 1 ml (StemCell Technologies, 07913). The flask was placed on a rotator and incubated at 37° C. for 1 h. The cells were then centrifuged at 1,000 r.p.m. for 5 min. Cell pellets were resuspended and later embedded into Matrigel (Corning, 356231) as per the previous published protocol (44). Colorectal carcinoma organoids were passaged using iced-cold PBS and Gibco TrypLE Express (Thermo Fisher Scientific, 12604039) when the cells reached 80-90% confluence. CCLF_CORE_0001_T will be deposited to a third-party distributor at a later date.

All cell lines tested negative for mycoplasma.

Generation of Ectopic WRN cDNA-Expressing Cell Lines

The catalytically active version, exonuclease-dead (E84A), helicase-dead (K577M) and dually exonuclease and helicase-dead (E84A/K577M) versions of WRN cDNA were a gift from R. J. Monnat (Addgene, plasmids 46038, 46036, 46035 and 46037, respectively). The missense mutant forms of WRN have been previously demonstrated to lack their indicated enzymatic activity (14). The WRN sequence was cloned into a modified lentiviral expression vector, pLX_TRC209, under an EF1A promoter and modified to contain a neomycin-selectable marker. Sanger sequencing of the vectors and genomic DNA after integration were performed to confirm sequence identity. Lentivirus was produced as described below and transduced into dually Cas9-Firefly-luciferase-expressing KM12 cells to create stable ectopic WRN cDNA-expressing cell lines.

Lentiviral Production

Lentiviral production was performed using HEK293 Ts as described on the GPP portal (portals.broadinstitute.org/gpp/public/).

sgRNAs sgRNAs used in validation studies were designed using the Broad Institute Genetic PerturbationPlatformssgR-NADesigner(portals.broadinstitute.org/gpp/public/analysis-tools/sgrna-design). sgRNAs targeting WRN include WRN sgRNA 1 (target sequence GTAAATTGGAAAACC-CACGG; SEQ ID NO: 1), WRN sgRNA 2 (ATCCTGTG-GAACATACCATG; SEQ ID NO: 2), WRN sgRNA 3 (GTAGCAGTAA GTGCAACGAT; SEQ ID NO: 3). sgRNA targeting the exon-intron junction (WRN EU sgRNA) were designed using the DESKGEN Cloud tool (www.deskgen.com/landing/cloud.html). The target sequence for WRNEU sgRNA is AGCACGTACAT-AAGCATCAG (SEQ ID NO: 4). Two negative controls targeting intergenic sites on chromosome 2 were used: Chr.2-2 sgRNA (GGTGTGCGTATGAAGCAGTG; SEQ ID NO: 17) and Chr.2-4 sgRNA (GCAGTGCTAACCTTG-CATTG; SEQ ID NO: 18). Two pan-essential controls targeting POLR2D (AGAGACTGCTGAGGAGTCCA; SEQ ID NO: 19) and MYC (ACAACGTCTTG-GAGCGCCAG; SEQ ID NO: 20) were used. sgRNAs were inserted in the pXPR_BRD003 lentiviral vector and inserts were verified by Sanger sequencing. sgRNAs targeting MLH1 include MLH1 sgRNA 1 (TTTGGCCAGCAT-AAGCCATG; SEQ ID NO: 21) and MLH1 sgRNA 2 (GCCAGCACATGGTTTAGGAG; SEQ ID NO: 22). sgRNAs targeting MLH1 were inserted in the pXPR_BRD051 lentiviral all-in-one vector, which also expresses Cas9.

shRNAs shRNAs targeting WRN were chosen from project DRIVE. shRNAs targeting WRN include WRN shRNA 1 (CAGCACTGCCAATGGTTCCAA; SEQ ID NO: 5) and WRN shRNA 2 (GCCTTAACAGTCTGGTTAAAC; SEQ ID NO: 6). Positive pan-essential controls include PSMD2 shRNA (CGCCAGTTAGCTCAATATCAT; SEQ ID NO: 23) and RPS6 shRNA (CCGCCAGTATGTTGTAAGAAA; SEQ ID NO: 24). RFP shRNA (CTCAGTTCCAGTACGGCTCCA; SEQ ID NO: 25), WRN-C911 shRNA 1 (CAGCACTGGGTATGGTTCCAA; SEQ ID NO: 26) and WRN-C911 shRNA 2 (GCCTTAACT-CACTGGTTAAAC; SEQ ID NO: 27) were used as negative controls. These shRNAs were inserted into pLKO.1 puro (Addgene, 8453) for constitutive expression and pRSITEP-U6Tet-(xx)-EF1-TetRep-2A-Puro (Cellecta, SVSHU6TEP-L) for doxycycline-inducible shRNA expression. All in vitro experiments used 0.2 μg ml$^{-1}$ of doxycycline for induction of shRNAs.

Immunoblotting

Figure 4A:
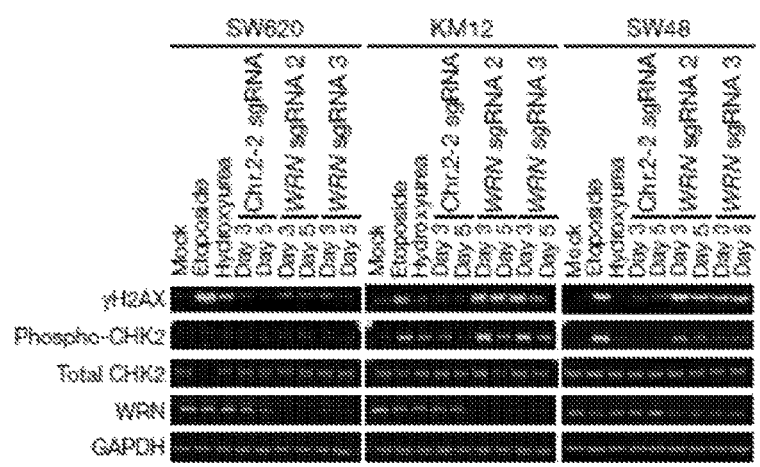
FIGS. 4A to 4F demonstrate that WRN depletion in MSI cells led to accumulation of DSBs.
Figure 4B:
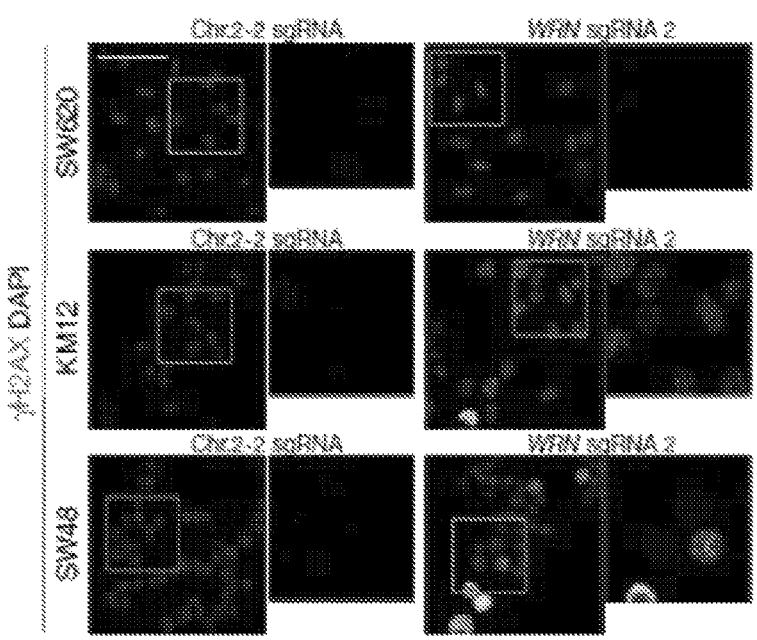
Figure 4C:
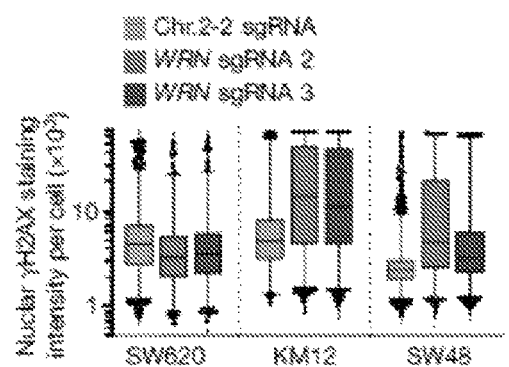

For immunoblotting, cells were lysed in RIPA buffer (Sigma-Aldrich) supplemented with complete Protease Inhibitor Cocktail (Roche, 11697498001) and a Halt Phosphatase Inhibitor Cocktail (Thermo Fischer Scientific, 78428). For etoposide and hydroxyurea treatment (FIG. 4A), cells were treated with 10 μM etoposide and 1 mM hydroxyurea, respectively, 6 h before collection. Lysates were fractionated in 4-12% Bis-Tris gels (Invitrogen), which was then transferred to PVDF membranes (Immobilon-FL PVDF Millipore, IPFL00010) and blocked for an hour with Odyssey Blocking Buffer (PBS) (LI-COR Biosciences, 927-40000). Types of primary antibodies and the dilutions used for immunoblotting were as follows: anti-phospho-CHK2 (T68) (R&D Systems, AF1626, 1:400); anti-total CHK2 (Cell Signaling Technology, 3440, 1:1,000); anti-7H2AX (Cell Signaling Technology, 9718, 1:1,000); anti-GAPDH (Cell Signaling Technology, 5174, 1:1,000); anti-MLH1 (Cell Signaling Technology, 3515, 1:1,000); anti-MSH3 (BD Biosciences, 611390, 1:400); anti-WRN (Novus Biologicals, nb100-472, 1:1,000). The following secondary antibodies were used: goat anti-rabbit IRDye 800CW (LI-COR, 926-32211, 1:5,000), goat anti-rabbit IRDye 680LT (LI-COR, 926-68021), and goat anti-mouse IRDye 800CW (LI-COR, 926-32210). Subsequent steps of immunoblotting were conducted using a near-infrared western blot detection system (LI-COR Biosciences) as per the manufacturer's recommendations. The immunoblots were performed three times except for blots shown in FIGS. 2E, 4A, 11E, 14B, and 14D, which were performed twice. Representative results from one experiment are shown.

Cell Viability Assay

Figure 2A:
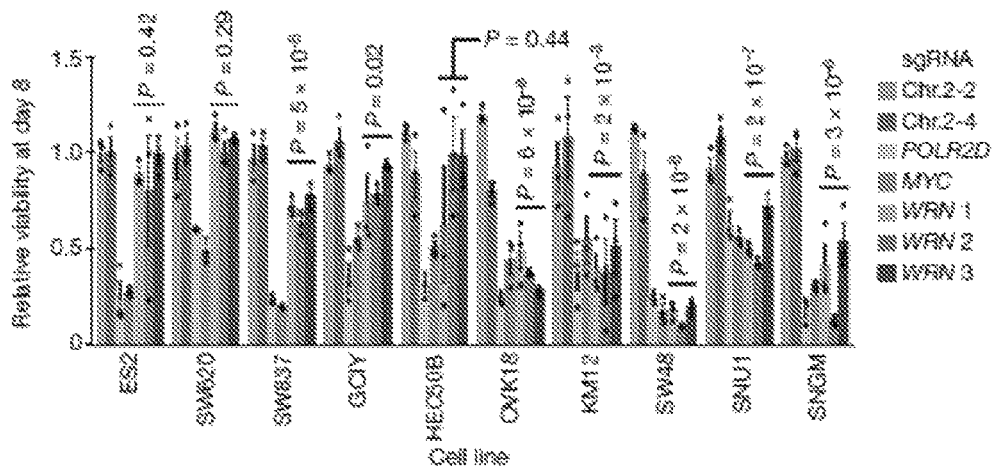
FIGS. 2A to 2G show that WRN was identified as a synthetic lethal partner with MSI.
Figure 4D:
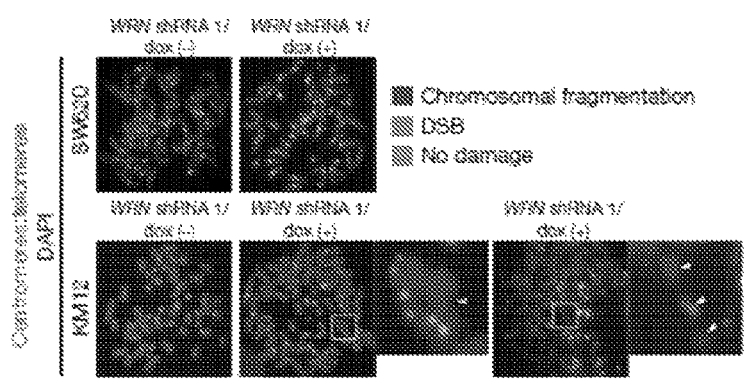
Figure 4E:
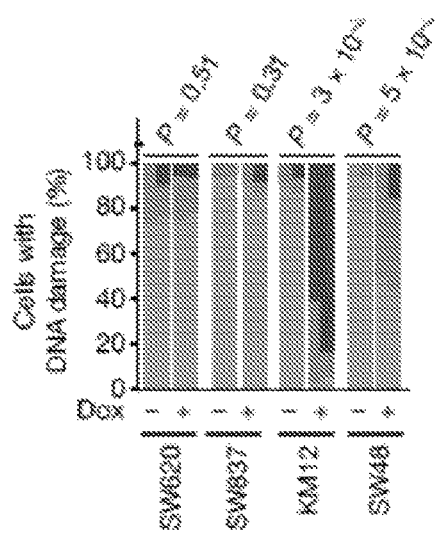
Figure 4F:
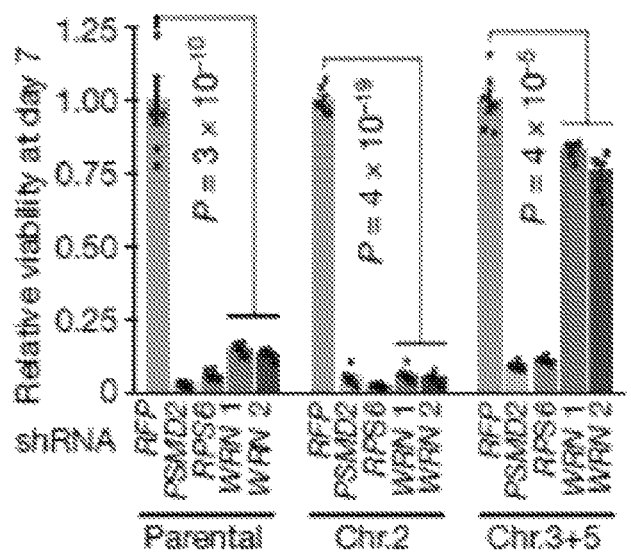
Figures 14A, 14B:
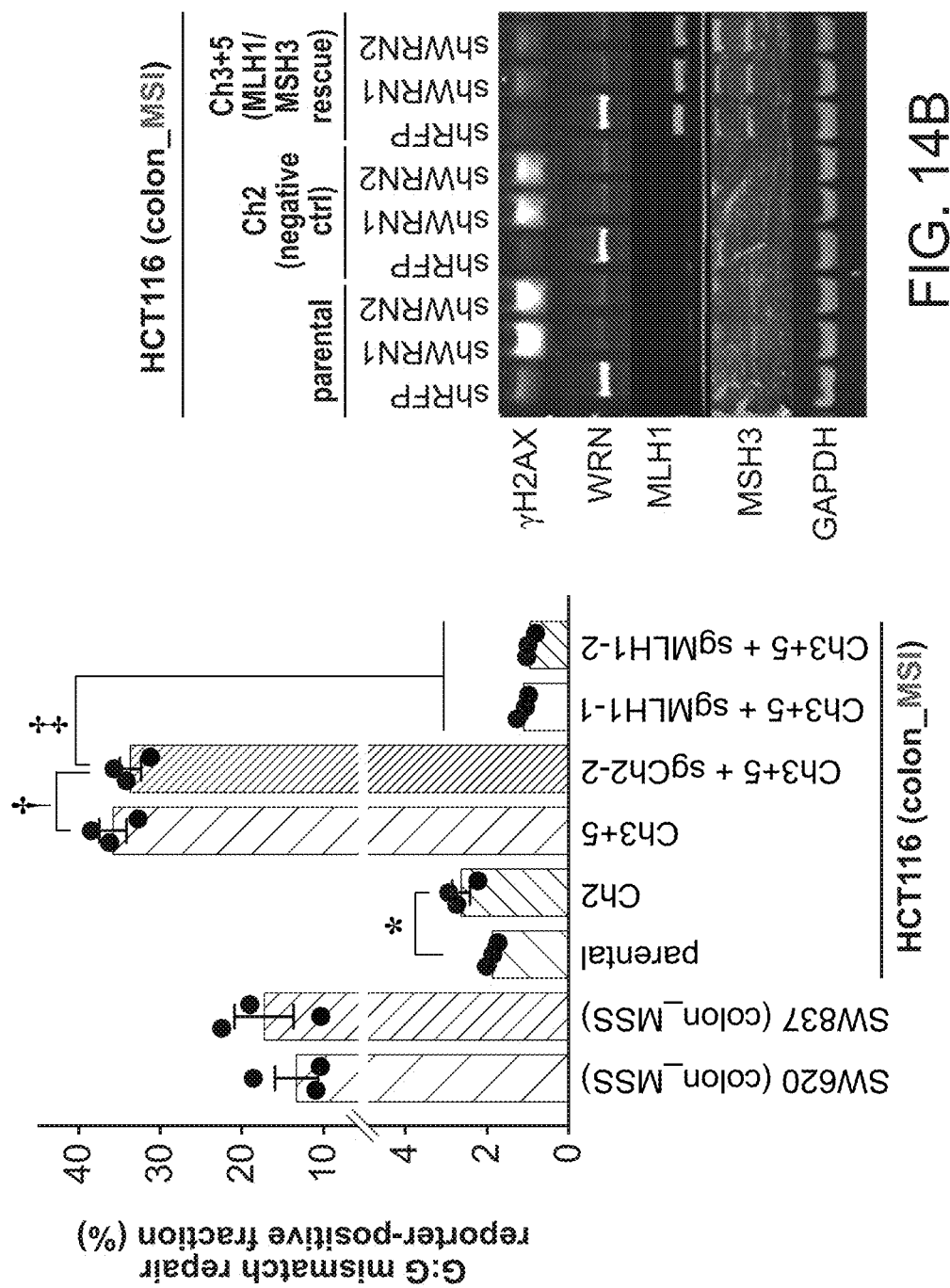
FIGS. 14A to 14F show that MMR deficiency contributes to WRN dependency.
Figure 14C:
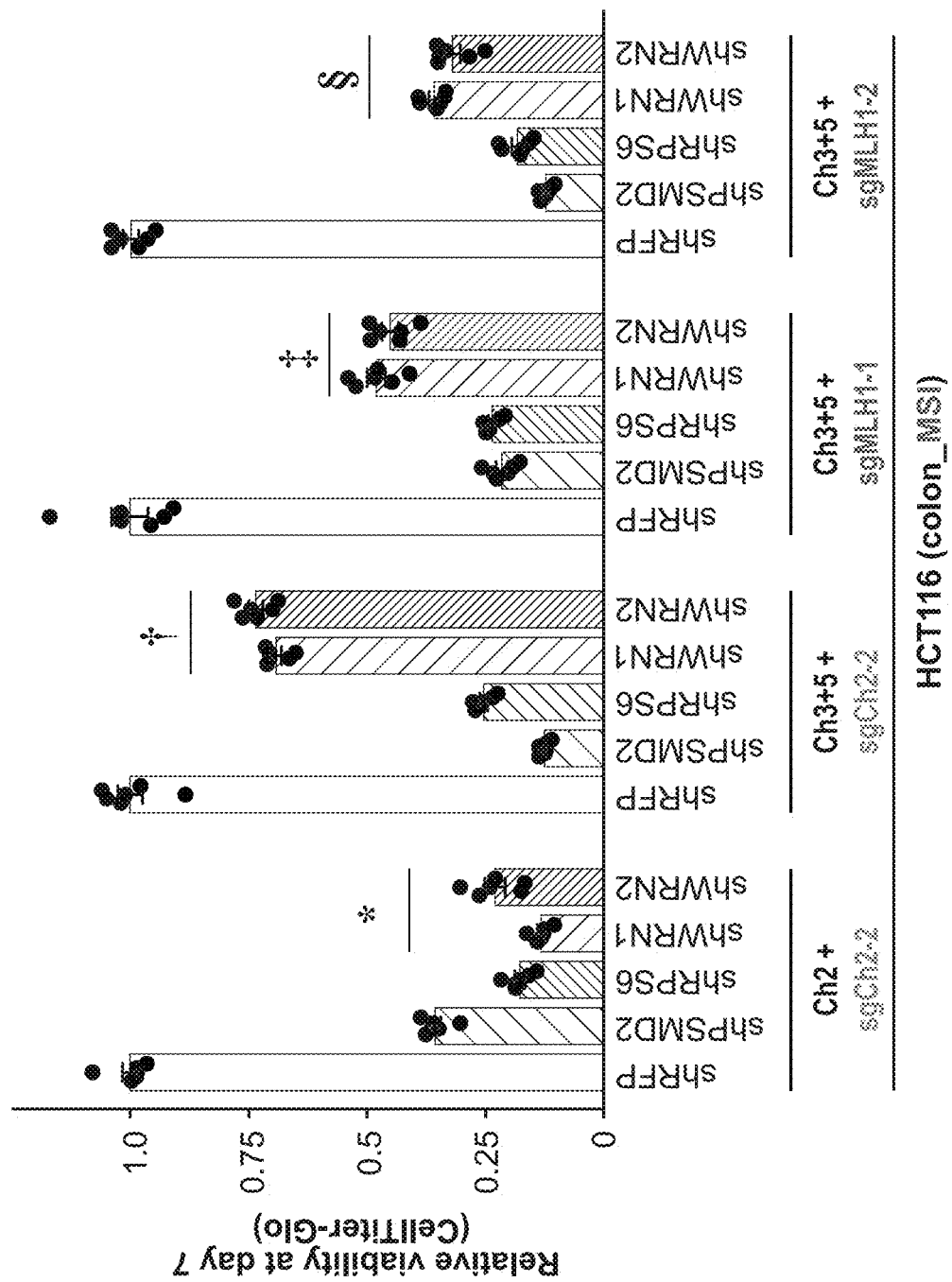

Cas9-expressing versions of the following cell lines were seeded in 100 µl of medium in 96-well plates (Corning 3904) excluding edge wells at the following densities: ES2, $10^3$ cells per well; OVK18, $1.5 \times 10^3$ cells per well; SW620, $2 \times 10^3$ cells per well; KM12, $2 \times 10^3$ cells per well; SW837, $2.5 \times 10^3$ cells per well; SW48, $2.5 \times 10^3$ cells per well; GCIY, $2 \times 10^3$ cells per well; SNU1 $1.5 \times 10^3$ cells per well; HEC50B, $1.75 \times 10^3$ cells per well; SNGM, $1.5 \times 10^3$ cells per well. All cell lines, except SNU1, were seeded the day before transduction. SNU1 cells—a line grown in suspension-were seeded on the day of transduction with 4 µg ml$^{-1}$ polybrene. For the adherent cell lines, the medium was changed to medium containing 4 µg ml$^{-1}$ polybrene. Viral concentrations were predetermined to achieve >90% infection efficiency. Experiments were performed in triplicate by adding the appropriate volume of lentivirus to integrate vectors that encoded the desired sgRNA and the plates were spun at 931 g for 2 h at 30° C. The medium was changed the next day and every 3 days thereafter. Cell viability was assayed using CellTiter-Glo (Promega G7572) at 33 µl per well. Luminescence was read using a PerkinElmer EnVision 2105. Values were normalized to the average values from the negative control sgRNAs for each cell line. Experiments were performed three times. The triplicate results of one representative experiment are shown. Two-way ANOVA was used to test differences between the set of WRN sgRNAs or WRN shRNAs and negative control(s), while modelling individual sgRNA/shRNA differences (FIG. 2A, FIG. 4F, and FIG. 14C).

Figure 2B:
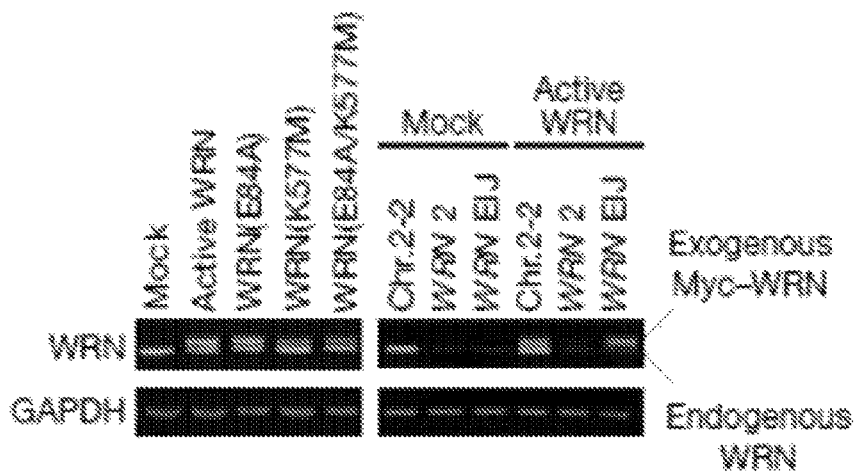
Figure 2C:
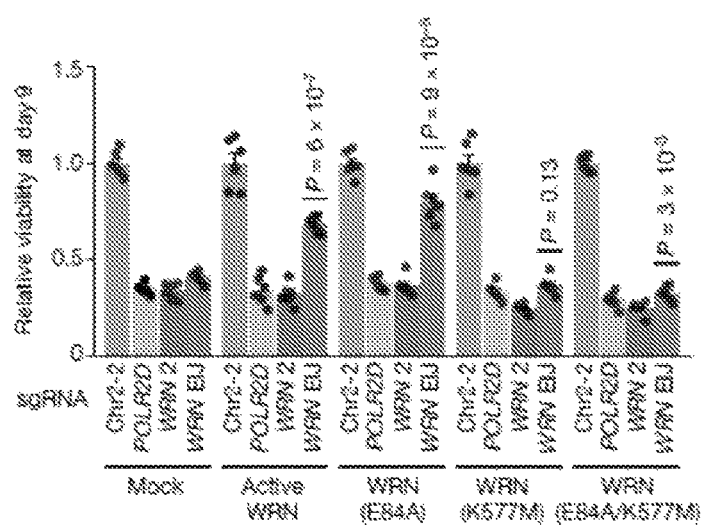
Figure 2D:
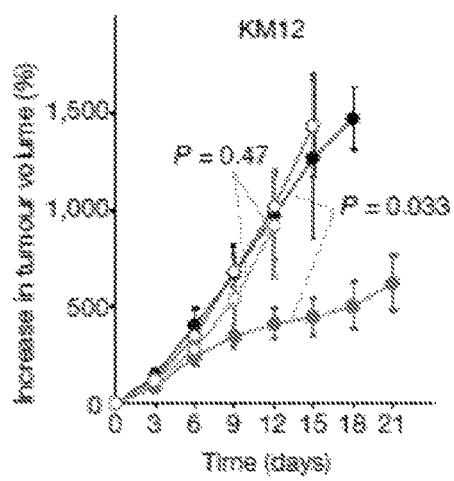
Figure 2E:
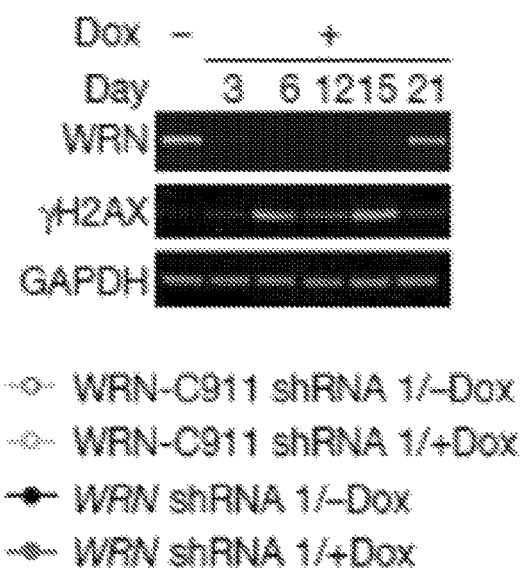
Figure 2F:
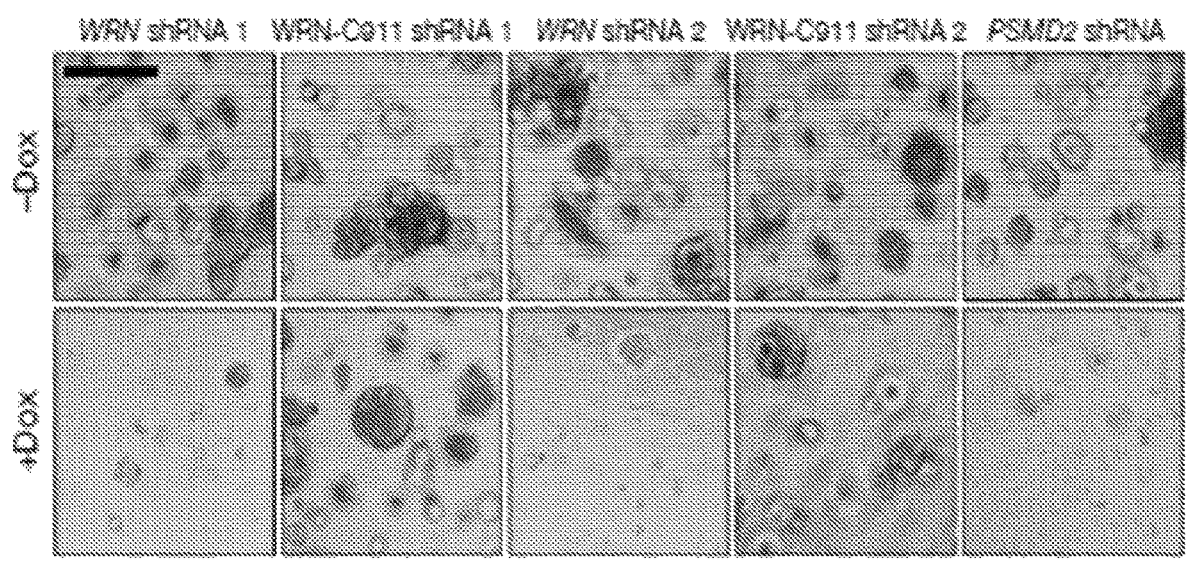
Figure 2G:
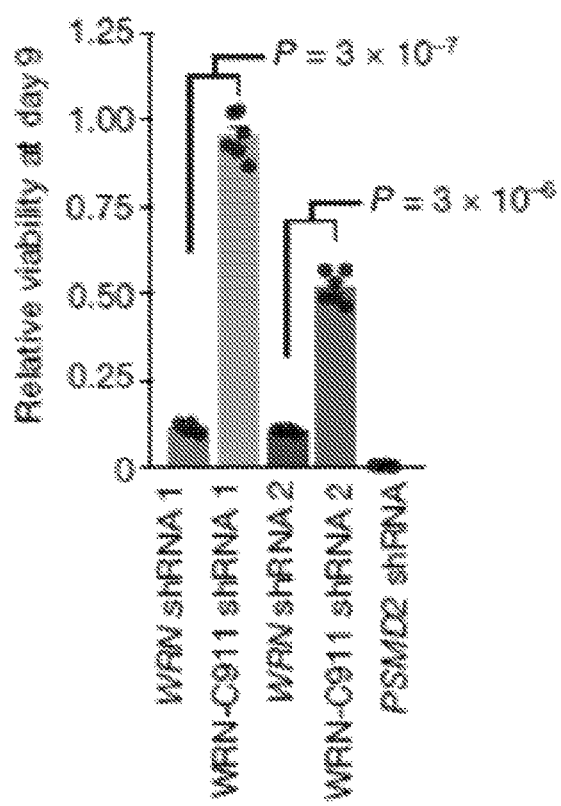

For CCLF_CORE_0001_T, $5 \times 10^4$ cells were seeded into 40 µl Matrigel domes in a 24-well plate in quadruplicate, with two wells with and two wells without 0.2 µg ml$^{-1}$ of doxycycline. Medium was refreshed every 2-3 days. Nine days after doxycycline treatment, cell viability was assayed by first aspirating the medium, adding 300 µl of CellTiter-Glo 3D (Promega G9681) and incubating at room temperature for 45 min on a shaker. Then, three aliquots of 90 µl were taken from each well and were transferred to a 96-well plate (Corning, 3904) for three technical replicates each from two biological replicates. Luminescence was read as above. Values are presented as the mean ratio of luminescence signal from the doxycycline-treated condition compared to the condition without doxycycline with error bars representing the s.e.m. unless otherwise stated. Two-tailed Student's t-tests were performed between each WRN shRNA and its corresponding seed control shRNA (FIG. 2G). This experiment was performed twice and data from one experiment is presented.

Immunofluorescence

Immunofluorescence experiments were conducted essentially as described previously (45) (except for the double staining for WRN and fibrillarin; see below). In brief, 2 days after lentiviral transduction, cells were seeded either on an 8-Well Lab-Tek Chamber Slide (Thermo Fisher Scientific, 177402) or on a 96-Well Clear Bottom Black Polystyrene Microplate (Thermo Fisher Scientific, 3904). The numbers of cells seeded per well for eight-well chambers (and 96-well plates) were as follows: $1 \times 10^6$ ($5 \times 10^5$), $1.2 \times 10^6$ ($6 \times 10^5$), $1.6 \times 10^6$ ($8 \times 10^5$), $6 \times 10^5$ ($3 \times 10^5$), and $8 \times 10^5$ ($4 \times 10^5$) cells/well for SW620, KM12, SW48, ES2, and OVK18 cells, respectively. Cells were fixed and stained 2 days later. Micrographic images were acquired using either epifluorescence microscopy (FIGS. 3B, 9A, 9C, and 9E) or confocal microscopy (FIGS. 4B, 10B, 10E, 10G, 11A and 11C), which were performed on an Axio Observer.Z1 microscope equipped with an Axiocam 506 mono camera and Apoptome.2 (Zeiss) and a Zeiss LSM 700 laser scanning confocal system equipped with Axio Observer (Zeiss), respectively. These confocal microscopy images represented maximum intensity projections of 5 consecutive planes with a step size of 0.08 µm.

Figure 10A:
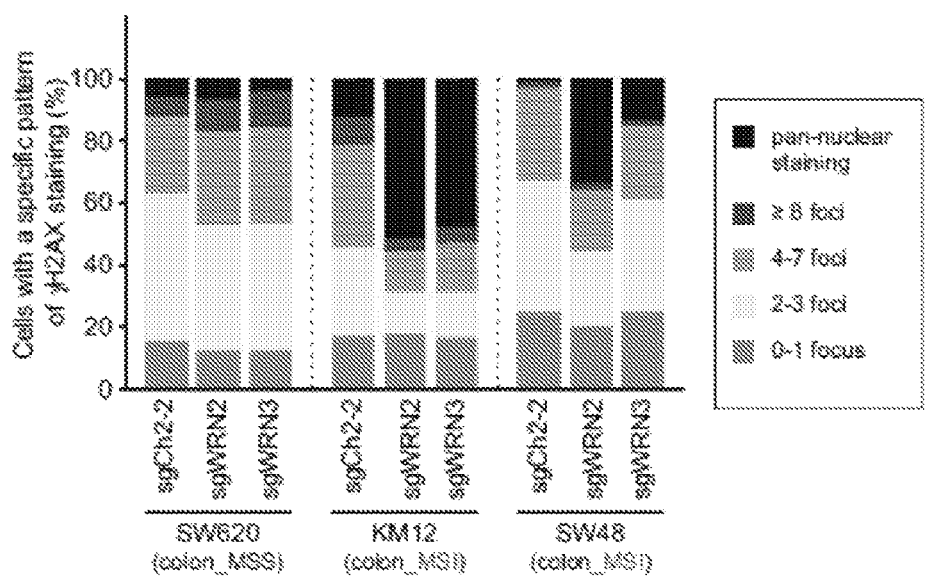
FIGS. 10A to 10H show that WRN depletion preferentially induced DSBs in MSI cells.
Figure 10B:
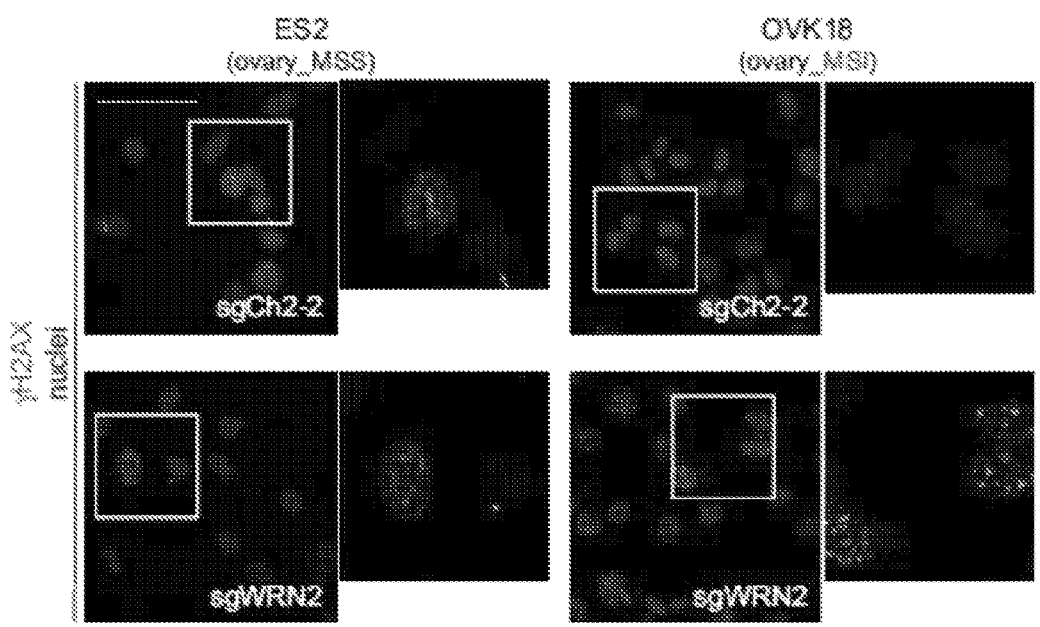
Figure 10C:
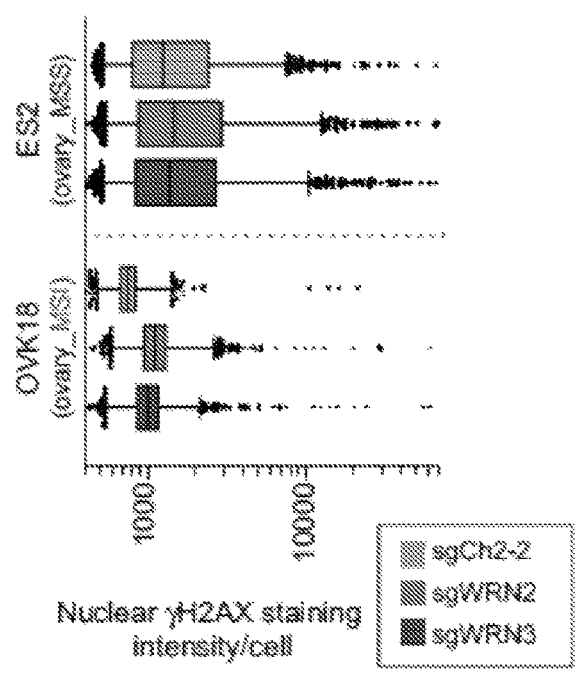
Figure 10D:
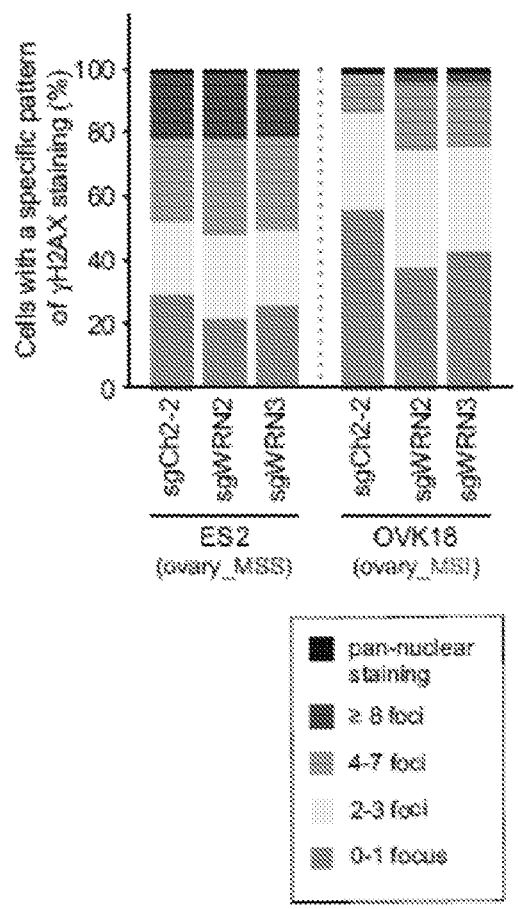
Figure 10E:
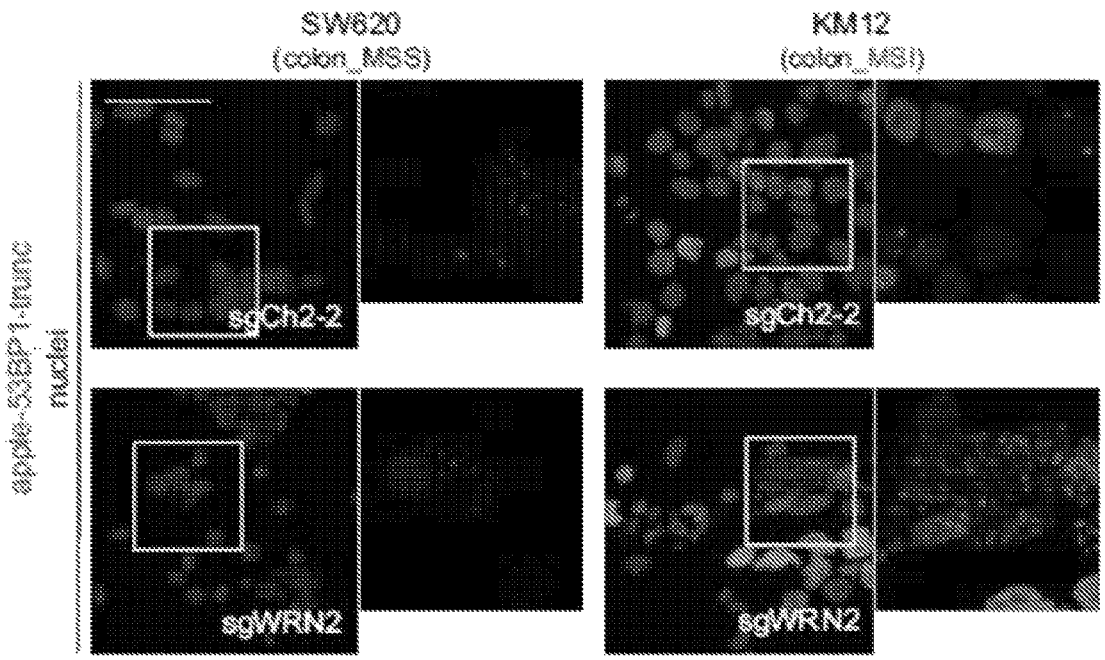
Figure 10F:
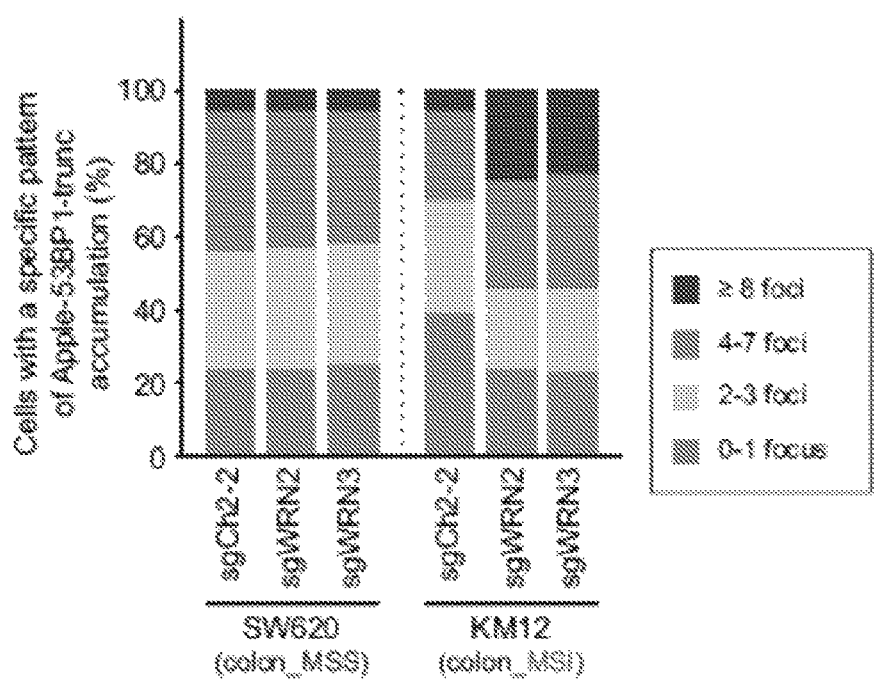
Figure 10G:
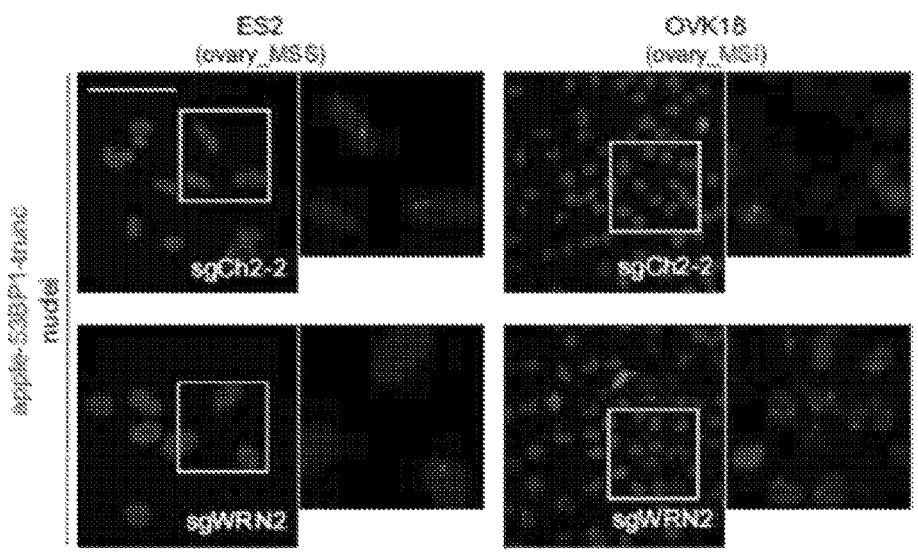
Figure 10H:
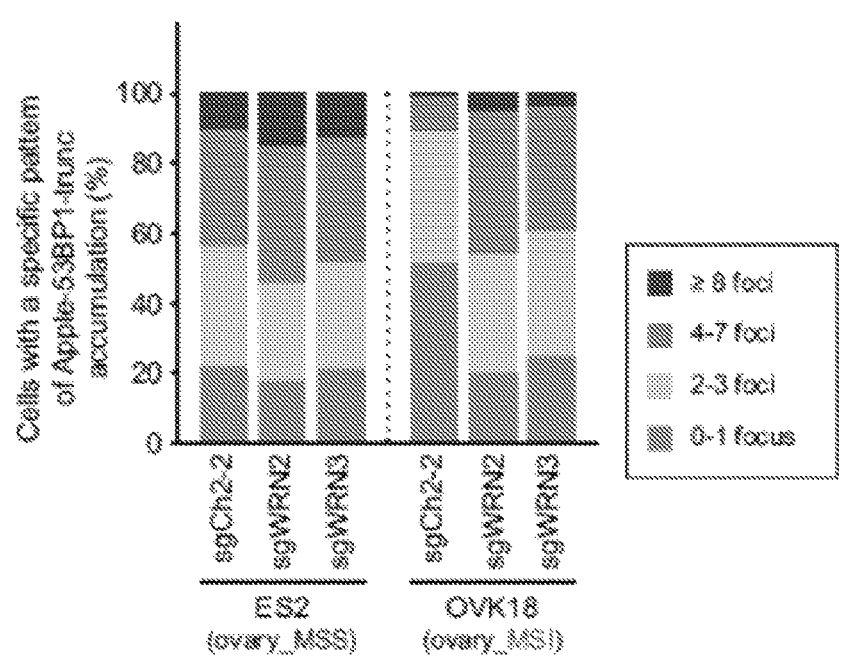

For image quantification, images were acquired using an Opera Phenix High-Content Screening System (PerkinElmer, HH14000000) and analyzed on Harmony High Content Imaging and Analysis Software (PerkinElmer, HH17000001). For phospho-p53, p21, γH2AX and phospho-ATM-staining, signal intensities in the nucleus of at least 1000 cells per sample were scored on background-subtracted images and presented as box plots. The lower and upper limits of the box plot represented 25th and 75th percentiles, respectively and the bar in the middle of the box represented the median value. The whiskers represent 1st and 99th percentiles, respectively. Outliers are represented as dots. To score the patterns of nuclear staining, cells exhibiting mean signal intensity of 12000 or higher (for γH2AX, all cell types) (20000 or higher for phospho-ATM, except for KM12 and SW48 cells, for which '40,000 or higher' and '10,000 or higher' were used to identify cells with pan-nuclear phospho-ATM staining patterns, respectively) were first separated as cells with a pan-nuclear pattern of staining. For the rest of the cells, the number of foci within the nucleus was scored using a spot-detection program in the software. The relative abundance of cells that showed pan-nuclear staining and the relative abundance of cells that contained a specific number of foci were plotted. The numbers of nuclear foci that were observed in cells expressing the Apple-53BP1-trunc fluorescent marker were scored similarly (FIGS. 10F and 10H). To assess differences between the effects of WRN knockout on immunofluorescence intensity values in MSI versus MSS cell lines, a linear model approach was used. Specifically, linear models were fit to the log(intensity) values with guide and cell line intercept terms. Comparisons of the change in log(intensity) after WRN knockout between cell lines were then obtained using the 'contrast' function of the R package lsmeans (46).

Figure 12A:
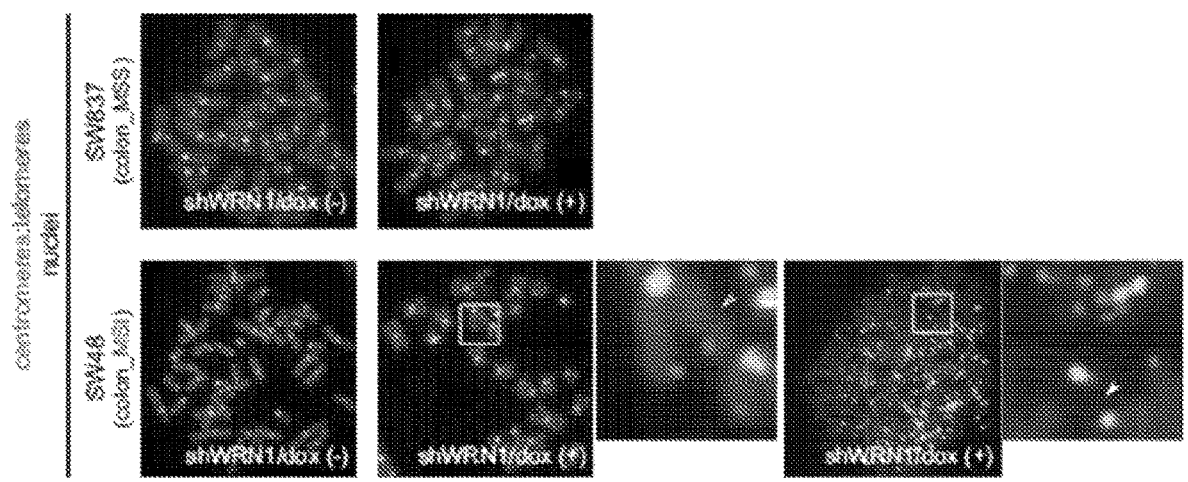
FIGS. 12A to 12D show that WRN is preferentially recruited to DNA in MSI cells.
Figure 12B:
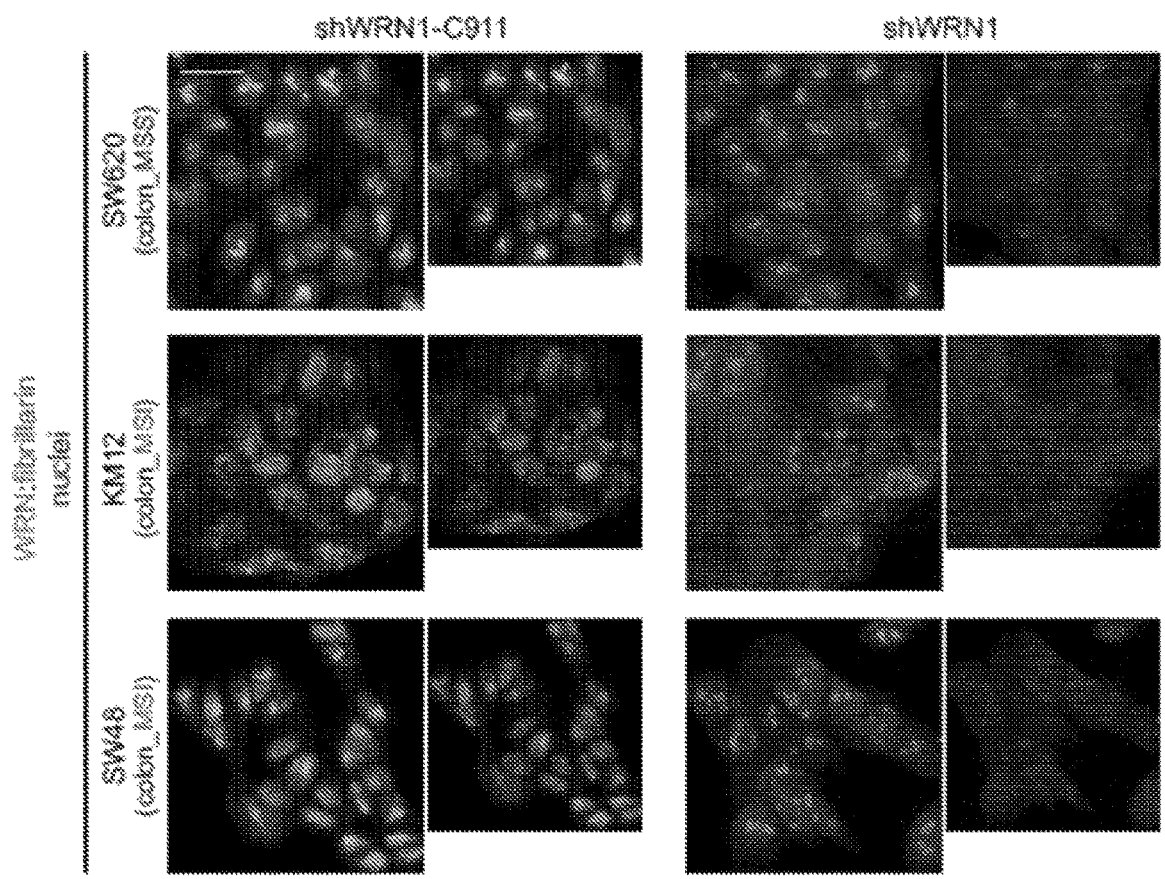
Figure 12C:
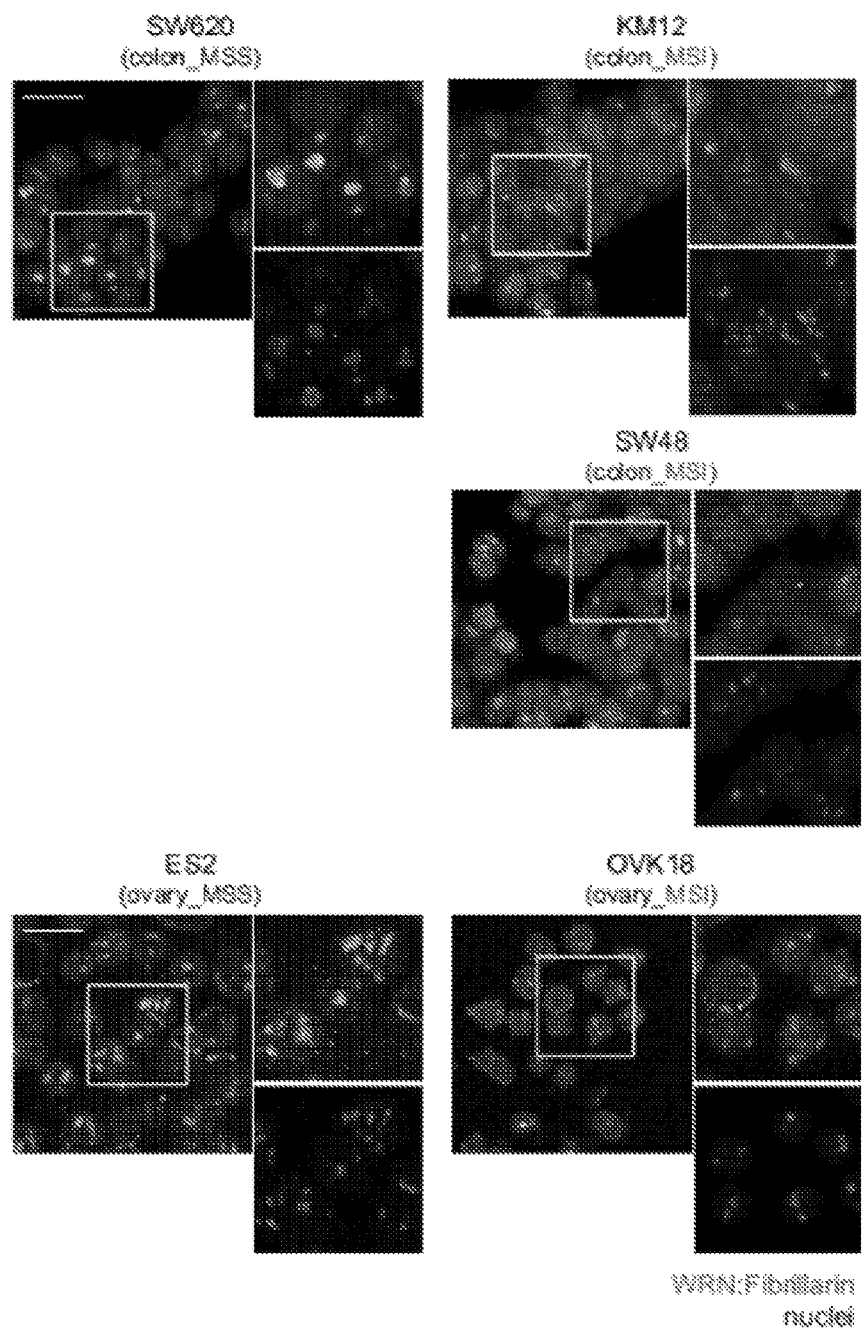
Figure 12D:
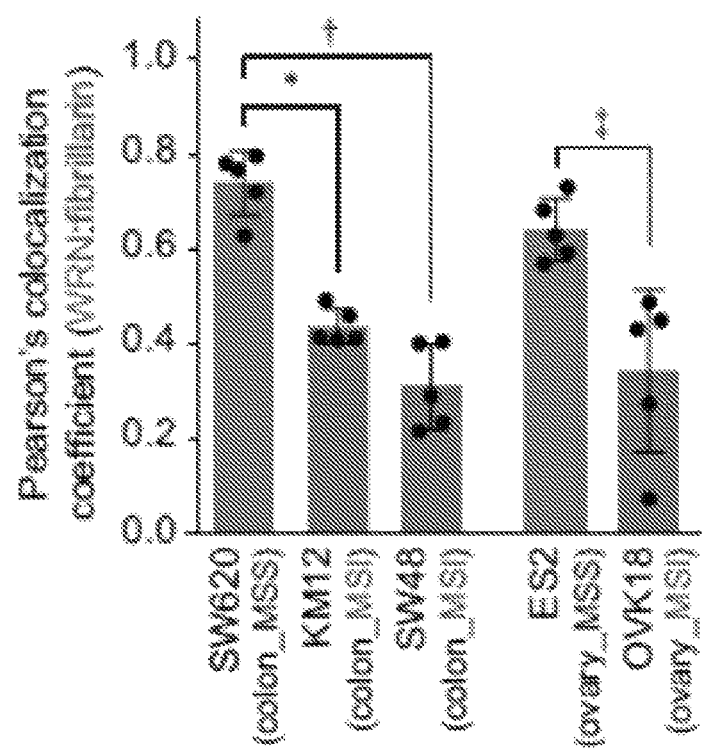

Immunofluorescence analysis of WRN and fibrillarin was performed as previously described (47). Images were obtained using the Zeiss LSM510 Upright Confocal System (FIGS. 12B and 12C). Weighted Pearson co-localization coefficients were calculated by obtaining z-stacks of five representative high-powered fields at 63× magnification and scored using the Zeiss Zen Blue software. Significance was calculated by two-tailed Student's 1-test for MSI cell lines compared to lineage-matched MSS cells (FIG. 12D).

Types of primary antibodies and the dilutions used for immunofluorescence were as follows: anti-γH2AX (Millipore Sigma, 05-636, 1:400); anti-p21 (Santa Cruz Biotechnology, sc-6246, 1:100); anti-phospho ATM [$S^{1981}$] (Millipore Sigma, 05-740, 1:200); anti-phospho CHK2 (T68) (R&D Systems, AF1626, 1:100); anti-fibrillarin (Abcam, ab5821, 1:500); anti-phosphor-p53 [S15](Cell Signaling Technology, 9284, 1:100); anti-WRN (Sigma-Aldrich W0393, 1:200).

For all immunofluorescence experiments except for the double staining for WRN and fibrillarin, the secondary antibody was goat anti-rabbit IgG, Alexa Fluor 488 (Thermo Fisher Scientific, A11008) and goat anti-mouse IgG, Alexa Fluor 488 (Thermo Fisher Scientific, A11001), which were used at a 1:200 dilution. For WRN and fibrillarin immunofluorescence experiments, goat anti-mouse IgG, Alexa Fluor 488 (Thermo Fisher Scientific, A-11001) and goat anti-rabbit IgG, Alexa Fluor 555 (Thermo Fisher Scientific, A-21428) were used at 1:1,000 dilution. Following secondary antibody treatment, the nuclei were counterstained with 4',6-diamidine-2'-phenylindole dihydrochloride (DAPI (Sigma-Aldrich, S9542); 1 µg ml$^{-1}$). All immunofluorescence experiments were performed twice. Representative results from one experiment are shown.

Luciferase Competitive Growth Assay

Dual Cas9-Firefly-luciferase- and *Renilla*-luciferase-expressing cells were generated by transduction of Firefly-luciferase cDNA and *Renilla*-luciferase cDNA, respectively, in a pLX_TRC313 lentiviral expression vector containing a hygromycin-resistance gene. After hygromycin selection, these two versions of the cell line were co-seeded in a 96 well plate at the following densities per well for each version: ES2 $2\times10^3$ cells per well, OVK18, $3\times10^3$ cells per well; SW620, $4\times10^3$ cells per well; KM12, $4\times10^3$ cells per well. The following day, cells were transduced with lentivirus expressing the indicated sgRNA and a puromycin-resistance gene in six replicates. The day following viral transduction, the medium was changed to include puromycin. Cells were split and assayed with the Dual-Glo Luciferase Assay System (Promega) per the manufacturer's recommendations every 3-4 days. Luminescence was determined using the Perkin Elmer EnVision 2105. Values were presented as the ratio of Firefly to *Renilla*-luciferase luminescence signal per condition and normalized to the mean of the corresponding negative control sgRNAs for each cell line. Experiments in FIG. 2C and FIG. 7B were performed three times. Two-tailed Student's t-tests were performed when comparing single sgRNAs (FIG. 2C). Two-way ANOVAs were performed when multiple WRN sgRNAs were compared to negative controls (FIG. 7B).

Clonogenic Assay

Figure 14D:
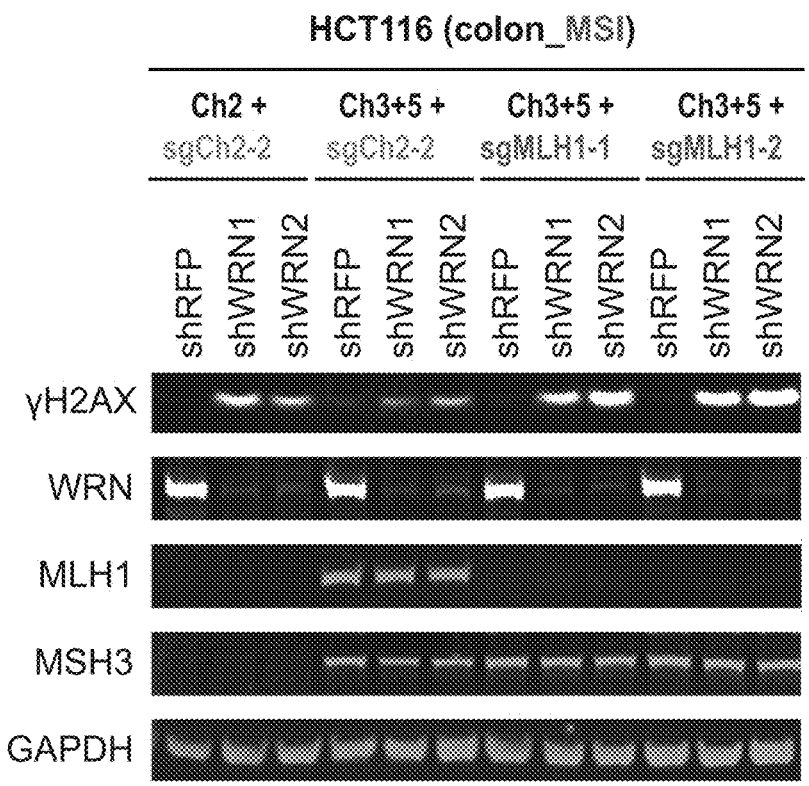
Figure 14E:
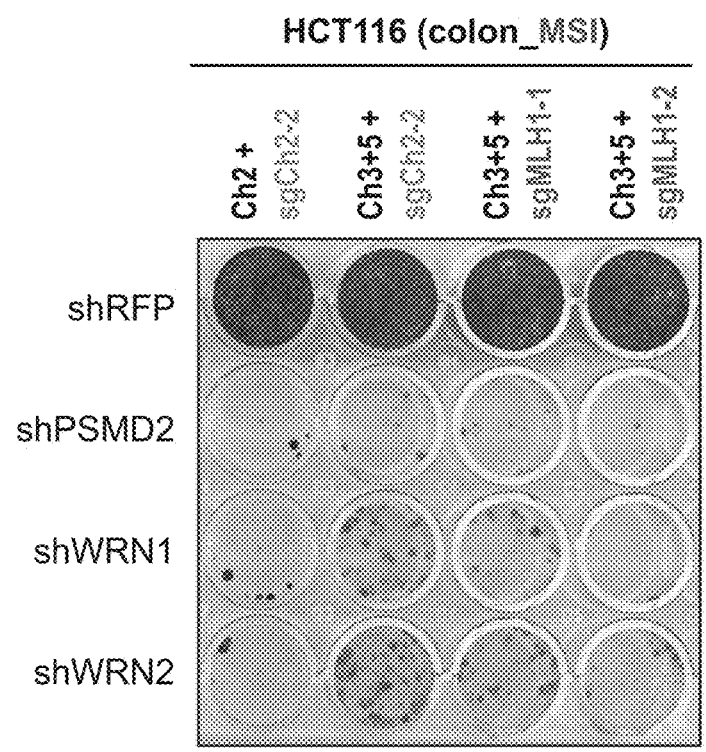
Figure 14F:
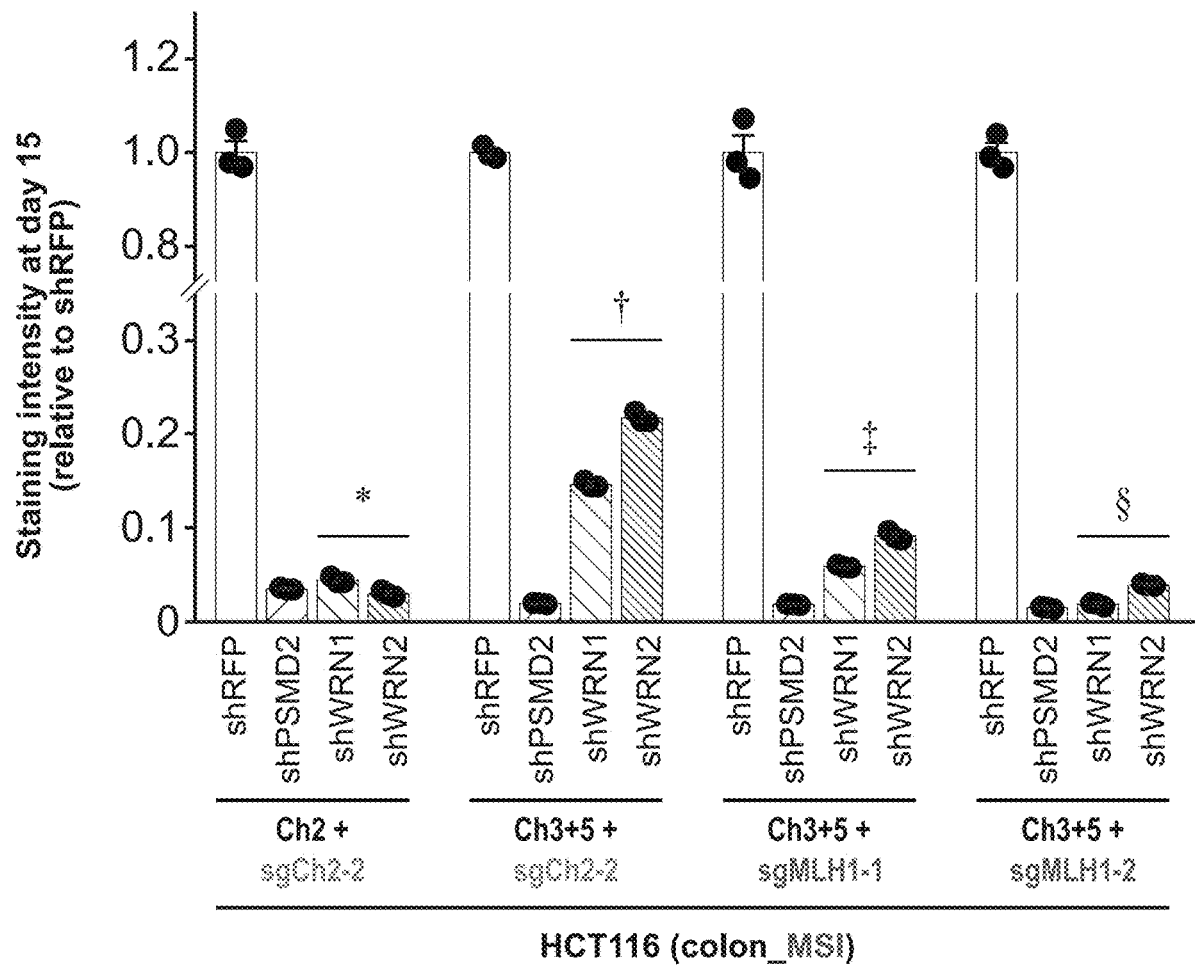

Cells were transduced with lentivirus expressing indicated shRNAs. After 24 h, the medium was replaced with medium containing 2 µg ml$^{-1}$ puromycin. After 24 h of puromycin selection, lentivirally infected cells were detached with trypsin and reseeded onto a 24-well plate. The number of cells seeded per well were as follows: $3\times10^3$, $4\times10^3$, $6\times10^3$, $1\times10^4$, $8\times10^3$, $8\times10^3$ and $1.2\times10^4$ cells for ES2, OVK18, SW620, SW837, KM12, SW48 and HCT116 cells, respectively. Cells were subsequently propagated for 2 weeks in puromycin-free medium, which was changed every 3 days. For crystal violet staining, cells were fixed with 10% formalin for 30 min at room temperature and subsequently stained with 250 µl per well of 0.1% crystal violet in 70% ethanol for 30 min at room temperature with constant shaking. To remove unbound crystal violet, cells were washed with deionized water three times for 5 min each. Quantification was performed by extracting the crystal violet dye with 250 µl of 10% acetic acid. Then, 50 µl was transferred into a 96-well format in triplicate. The experiments were performed three times (FIGS. 7C and 7D) or two times (FIGS. 14E and 14F). Crystal violet absorbance was determined using the Perkin Elmer EnVision 2105. The results of one representative experiment are shown with quantification, which shows the repeat measurements from a single experiment. Two-way ANOVA was performed for FIG. 14F, in which HCT116 cells expressing Chr.3+5 and Chr.2-2 sgRNA were compared to HCT116 cells expressing Chr.2 and Chr.2-2 sgRNA, and HCT116 cells expressing Chr.3+5 and MLH1 sgRNAs were compared to HCT116 cells expressing Chr.3+5 and Chr.2-2 sgRNA.

Cell Cycle Analysis

Figure 8A:
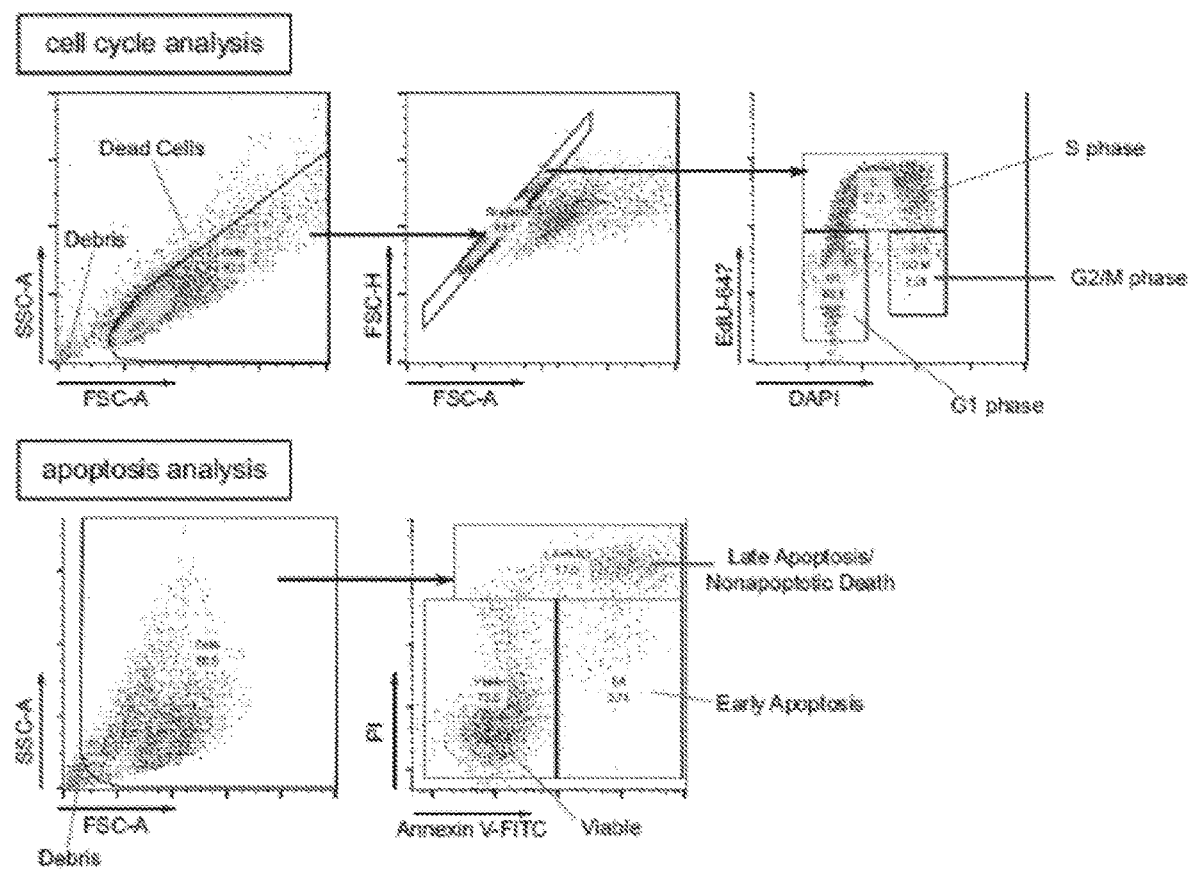
FIGS. 8A to 8D show that WRN depletion preferentially induced cell cycle arrest and apoptosis in MSI cells.
Figure 8B:
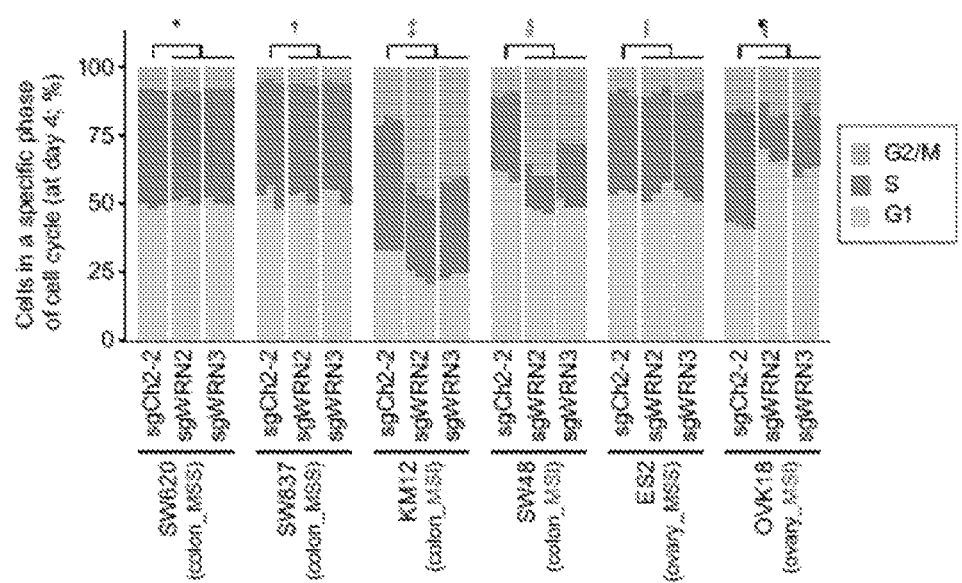

Cas9-expressing cell lines were lentivirally transduced to deliver the desired sgRNAs or shRNAs. Medium was changed the next day to allow for antibiotic selection. Subsequently, 4 days after the lentiviral transduction, cells were labelled with EdU, collected and stained as per the Click-iT Plus EdU Flow Cytometry Assay Kit recommendations. Stained cells were then examined using flow cytometry and results analyzed with FlowJo v.10. A representative result of two independent experiments is shown; each experiment was conducted in triplicate. Statistical analysis of the proportion of cells in S phase versus Chr.2-2 sgRNA was calculated by two-way ANOVA (FIG. 8B).

Apoptosis Assay

Figure 8C:
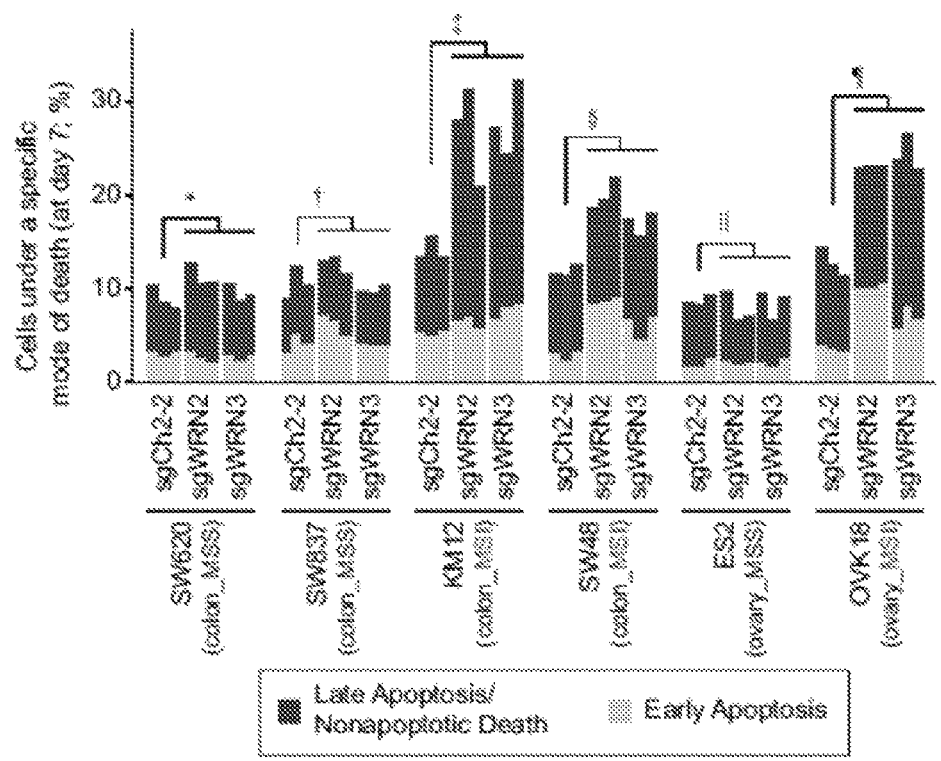
Figure 8D:
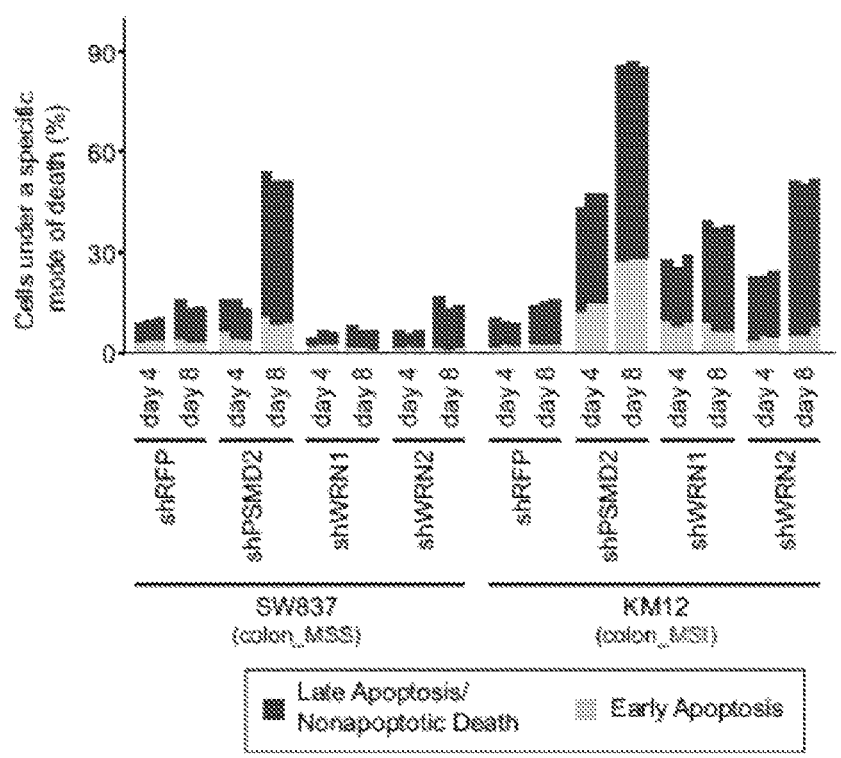

Cas9-expressing cell lines were lentivirally transduced to deliver vectors that encoded the desired sgRNAs or shRNAs. Medium was changed the next day without antibiotic selection. Cells were split 4 days after transduction. Then, 7 days after transduction, cells were collected and stained with annexin V-FITC and propidium iodide. Stained cells were then examined with flow cytometry and results analyzed with FlowJo. A representative result of two independent experiments is shown; each experiment was conducted in triplicate. Significance was calculated for the sum of the proportions of cells in early apoptosis, late apoptosis and nonapoptotic death categories; in cells expressing a WRN sgRNA compared to cells expressing Chr.2-2 sgRNA (control sgRNA) by two-way ANOVA (FIGS. 8C and 8D).

In Vivo Xenograft Studies

Studies were approved by the Institutional Animal Care and Use Committee (IACUC) of the Broad Institute under animal protocol 0194-01-18. IACUC guidelines on the ethical use and care of animals were followed. For growth curves, $10^6$ KM12 cells expressing WRN shRNA 1 or WRN-C911 shRNA 1 were inoculated subcutaneously into right hind flank of approximately 8-week-old female SCID Hairless Outbred (SHO) mice obtained from Charles River Laboratories. Tumors were measured twice weekly with calipers and the tumor volumes were calculated using the formula $\pi/6\times(\text{width}^2\times\text{length})$. When primary tumors reached around 100 mm$^3$, the mice were randomized onto Control Teklad Global 18% Protein Rodent Diet or Teklad Global 18% Protein Rodent Diet containing 625 mg kg$^{-1}$ doxycycline hyclate. Mice remained on their respective diets throughout the remainder of the study. Animal body weights were recorded twice weekly during the course of the study for body condition scoring. For the growth curves, n=5 (4 from days 15-18), 5, 4, 4 for WRN shRNA 1 without doxycycline, WRN shRNA 1 with doxycycline, WRN-C911 shRNA 1 without doxycycline, WRN-C911 shRNA 1 with doxycycline treatment, respectively. One mouse treated with KM12 cells with WRN shRNA 1 without doxycycline was euthanized before day 15 because of tumor ulceration. No experiments exceeded the maximal tumor volumes of 2,000 mm$^3$ set forth by the IACUC. This study was not blinded. Sample size calculations were not performed. For target engagement, one mouse per time point was inoculated in the right and left flanks. To compare xenograft tumor growth curves across experimental conditions, a linear mixed model was used to describe the percentage increase in tumor volume as a linear function of time, with random slope terms per mouse, and an interaction term between growth rate and experimental conditions. Maximum likelihood models were fit using the R package lme4 (48). Reported P values assessing the significance of interactions between growth rate and experimental conditions were derived using a likelihood ratio test. Tumors were collected at the indicated time points. Experiments in FIG. 2D were conducted once. The immunoblot for this experiment (FIG. 2E) was performed twice from the same protein lysates.

Telomere PNA-FISH of Metaphase Spreads

In brief, $3 \times 10^6$ cells were plated in 10-cm dishes in the absence of doxycycline. For cells treated with doxycycline, 0.2 µg ml$^{-1}$ of doxycycline was added and refreshed every 48 h. Then, 96 h after adding doxycycline, cells were treated with 10 µg ml$^{-1}$ of colcemid for 3 h and then detached with trypsin. Half of the cell pellet was saved for immunoblot analysis. The other half of the cell pellet was treated with a hypotonic solution (60 mM KCl) and fixed with a 3:1 ratio of methanol:acidic acid. Metaphases were spread onto a slide and fixed with 3% formalin. The PNA-FISH probe ((CCCTAA)$_3$ PNA probe (PNA Bio)) was applied to the slides and denatured at 85° C. for 3 min. The slides were washed with washing solution I (70% formamide, 0.1% Tween-20, 0.1% BSA in 10 mM Tris buffer, pH 7.5) twice and three times with washing solution II (150 mM NaCl, 0.1% Tween-20, 0.1% BSA in 50 mM Tris buffer, pH 7.5). Cy5-ATTCGTTGGAAACGGGA (SEQ ID NO: 28) was used to label centromeres. Images were captured with a Nikon Eclipse 80i microscope and processed with the NISElements BR software. In total, 30 to 60 metaphases were analyzed for cells of the indicated conditions. Two-tailed Student's t-tests were performed (FIG. 4E). These experiments were performed twice.

Fluorescence-Based Multiplexed Host Cell Reactivation (FM-HCR) Assays

Assays to assess MMR impairment in isogenic HCT116 cells were carried out as previously described (49). SW620, SW837, HCT116 and its derivatives were collected as a subconfluent population (<85%) and electroporated with FM-HCR reporter plasmids (50 ng pmaxOrange_GG for mismatch repair with 50 ng pmax_mPlum as transfection control or 50 ng pmax_mOrange as undamaged control and 50 ng pmax_mPlum as transfection control) and carrier DNA in a 10-µl volume using the ThermoFisher Neon transfection system (1,200 V, 20 ms, 2 pulses). Percentage reporter expression was calculated as previously reported for MMR reporters (49). Approximately $2 \times 10^5$ transfected cells were seeded into 12-well culture plates and analyzed by flow cytometry at 24 h after transfection. These experiments were performed three times. Two-tailed Student's t-tests were performed when comparing HCT116 parental to HCT116 Chr.2 cells and HCT116 parental to HCT116 Chr.3+5 cells. Two-way ANOVA was performed when comparing HCT116 cells expressing an additional Chr.3+5 and Chr.2-2 sgRNA to HCT116 cells expressing an additional Chr.3+5 and MLH1 sgRNA 1 and HCT116 cells expressing an additional Chr.3+5 and MLH1 sgRNA 2 (FIG. 14A).

Example 2: Identification of Genetic Vulnerabilities in MSI Cancers

Figure 1B:
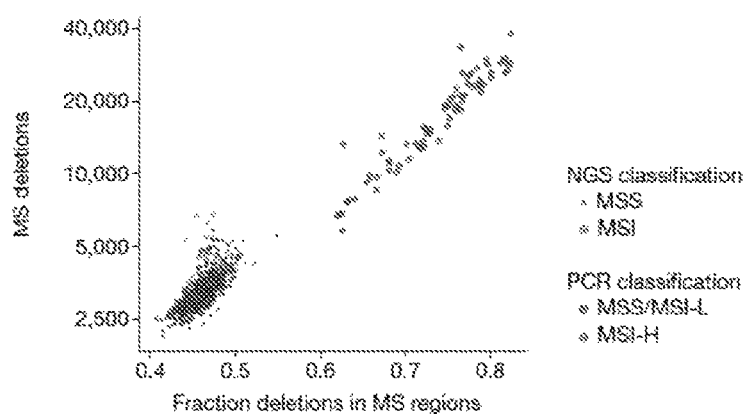
Figure 5A:
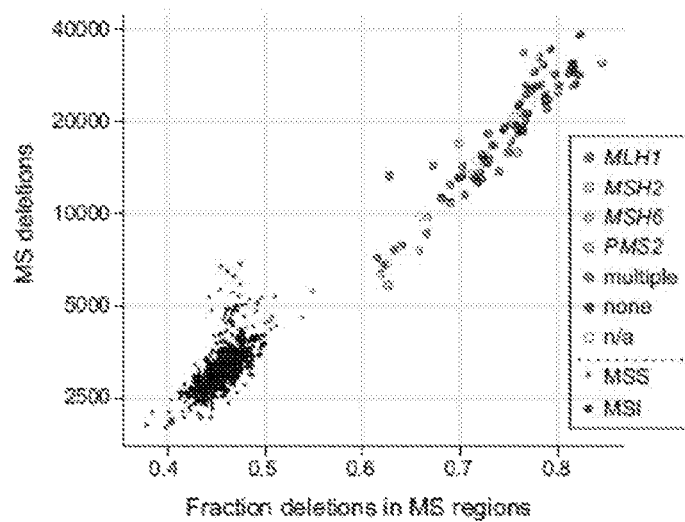
FIGS. 5A to 5E show that functional genomic screening identified MSI cancers selectively dependent on WRN.

To explore whether MSI and MMR deficiency might create vulnerabilities, and to identify candidate therapeutic targets for cancers that exhibit MSI and MMR deficiency, two independent large-scale cancer dependency datasets were leveraged for information: Project Achilles screened 517 cell lines with a genome-scale CRISPR-Cas9 library and project DRIVE analyzed 398 cell lines using an RNA interference library to define genes that were selectively essential in cancer cell lines with MSI (10, 11). By comparing essential genes in cell lines with or without specific features such as MSI, these cancer dependency datasets provided an opportunity to identify synthetic lethal interactions (FIG. 1A). MSI status was then determined using next-generation sequencing (12), and the number and fraction of deletions that were located within microsatellite regions were quantified, which thereby identified three groups: MSI, microsatellite stable (MSS) and indeterminate lines (FIG. 1B and Table 2 of priority document U.S. Ser. No. 62/853,412). These classifications were highly concordant with PCR-based MSI phenotyping (13) and with predicted MMR deficiency (FIG. 5A). In total, 51 unique MSI and 541 unique MSS cell lines (excluding those lines marked as indeterminate) were represented by one or both screening datasets.

Figure 1C:
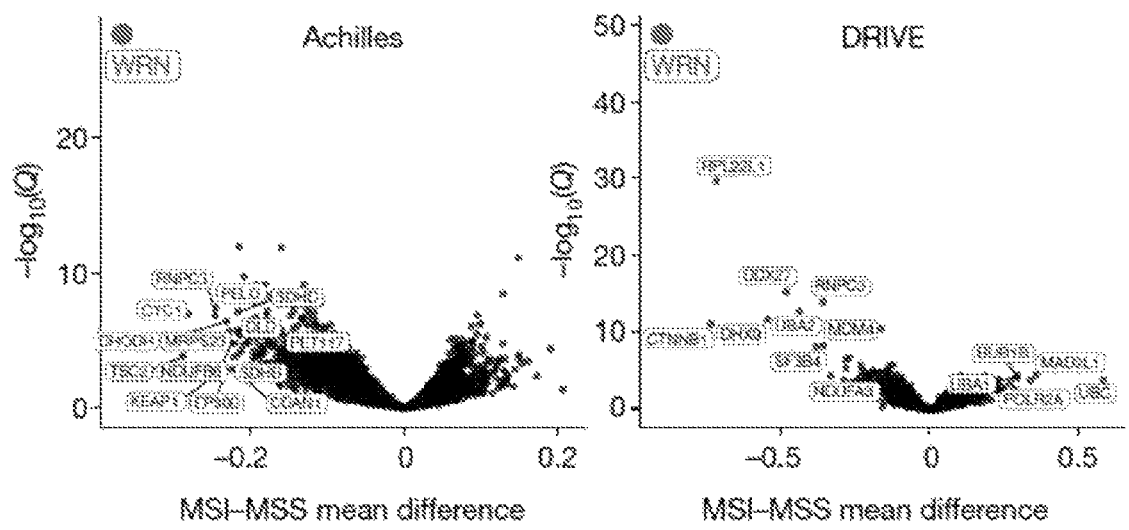
Figure 5B:
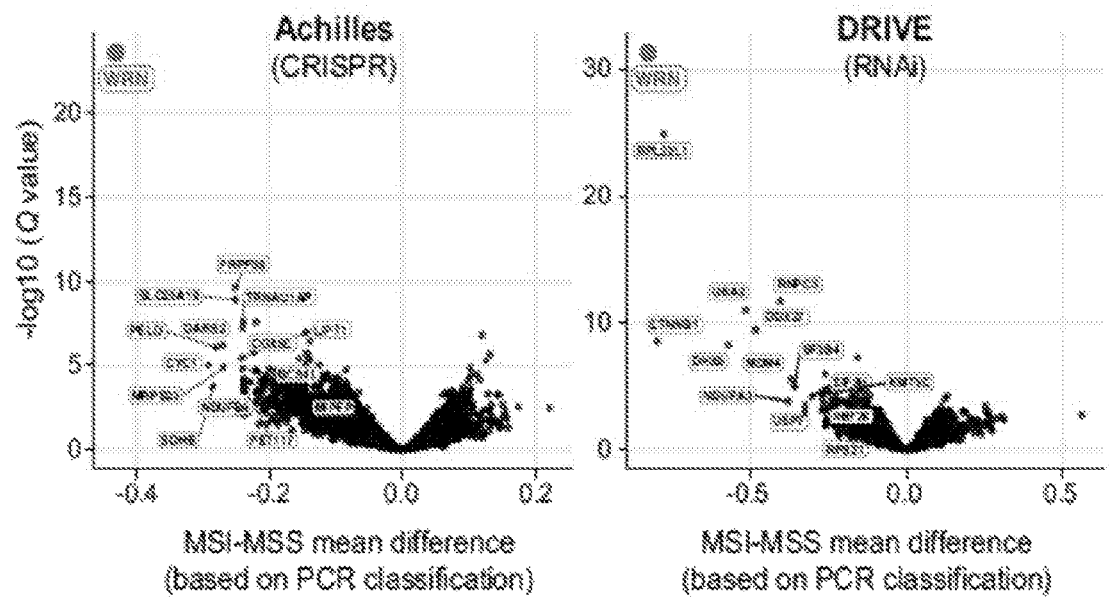
Figure 5C:
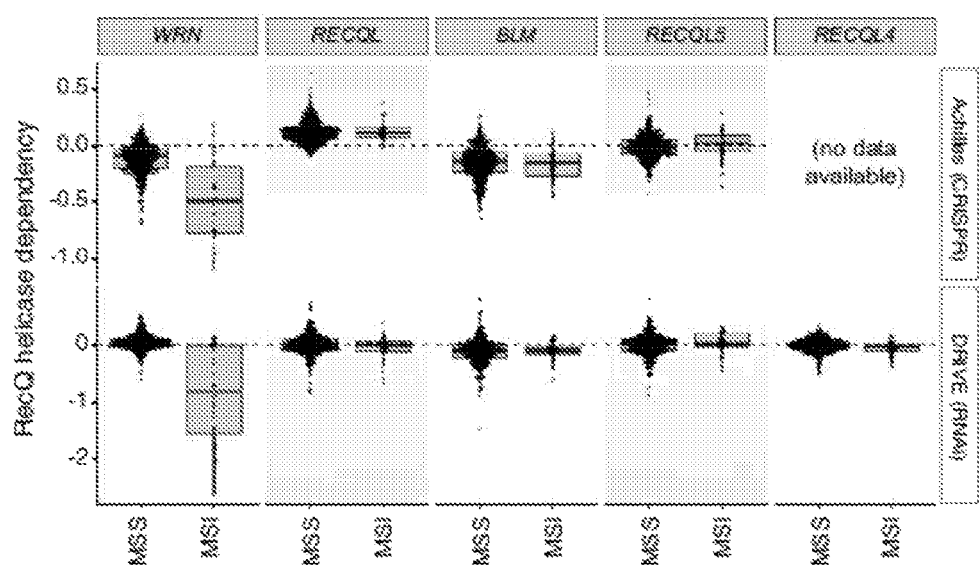
Figure 5D:
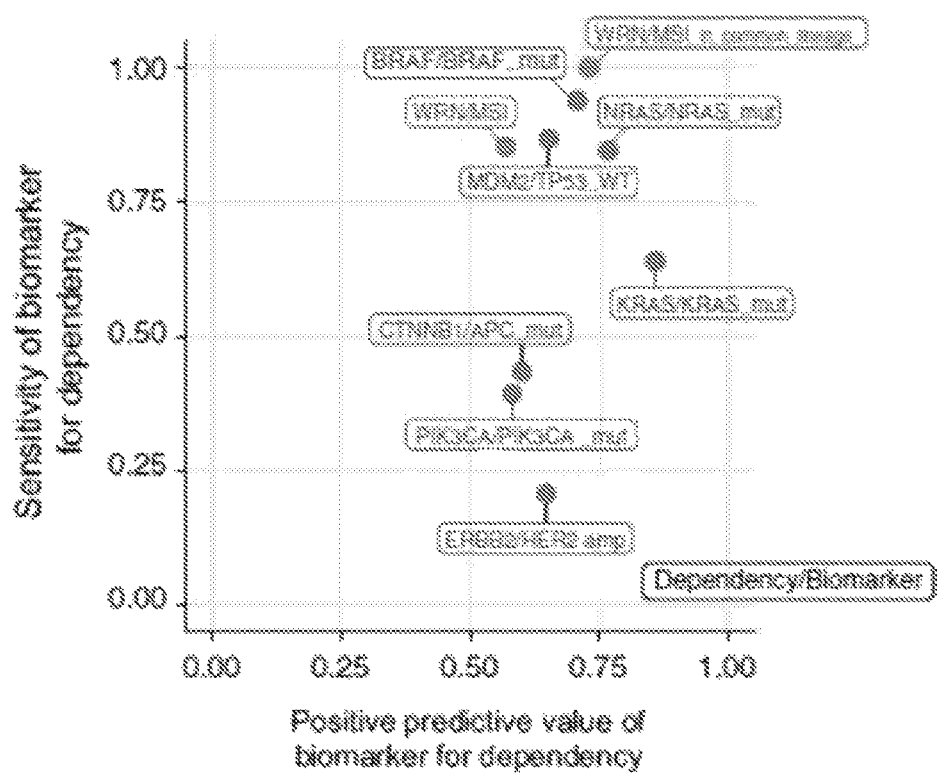
Figure 5E:
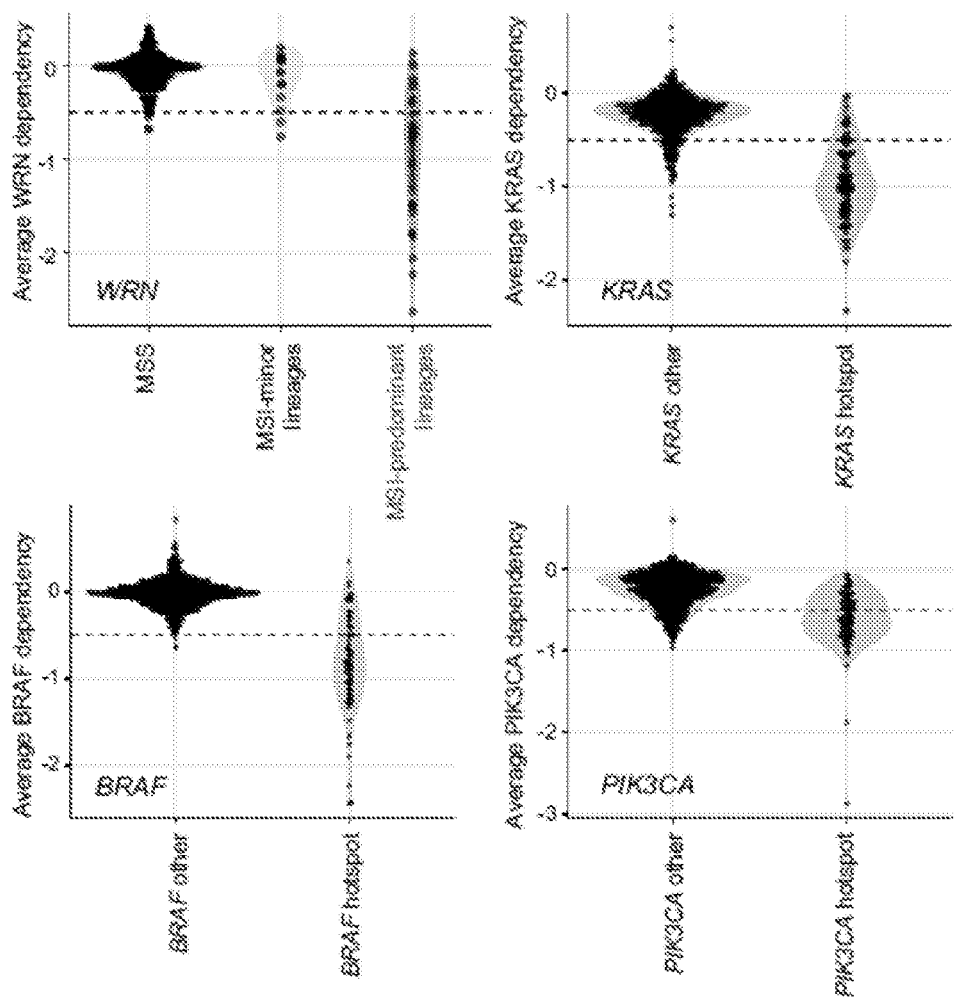

Projects Achilles (using CRISPR-Cas9) and DRIVE each independently identified WRN, which encodes a RecQ DNA helicase, as the top preferential dependency in MSI compared to MSS cell lines ($Q=4.8 \times 10^{-24}$ and $1.5 \times 10^{-45}$, respectively; FIG. 1C. These findings remained true with PCR-based MSI classifications (FIG. 5B). By contrast, none of the four other RecQ DNA helicases were preferentially essential in MSI cell lines (FIG. 5C). MSI was then evaluated as a biomarker for WRN dependency, and it was identified that the MSI-WRN relationship compared favorably to other strong biomarkers for vulnerabilities such as the relationships between activating KRAS and BRAF mutations and KRAS and BRAF dependencies, respectively (FIGS. 1D and 1E).

Figure 6A:
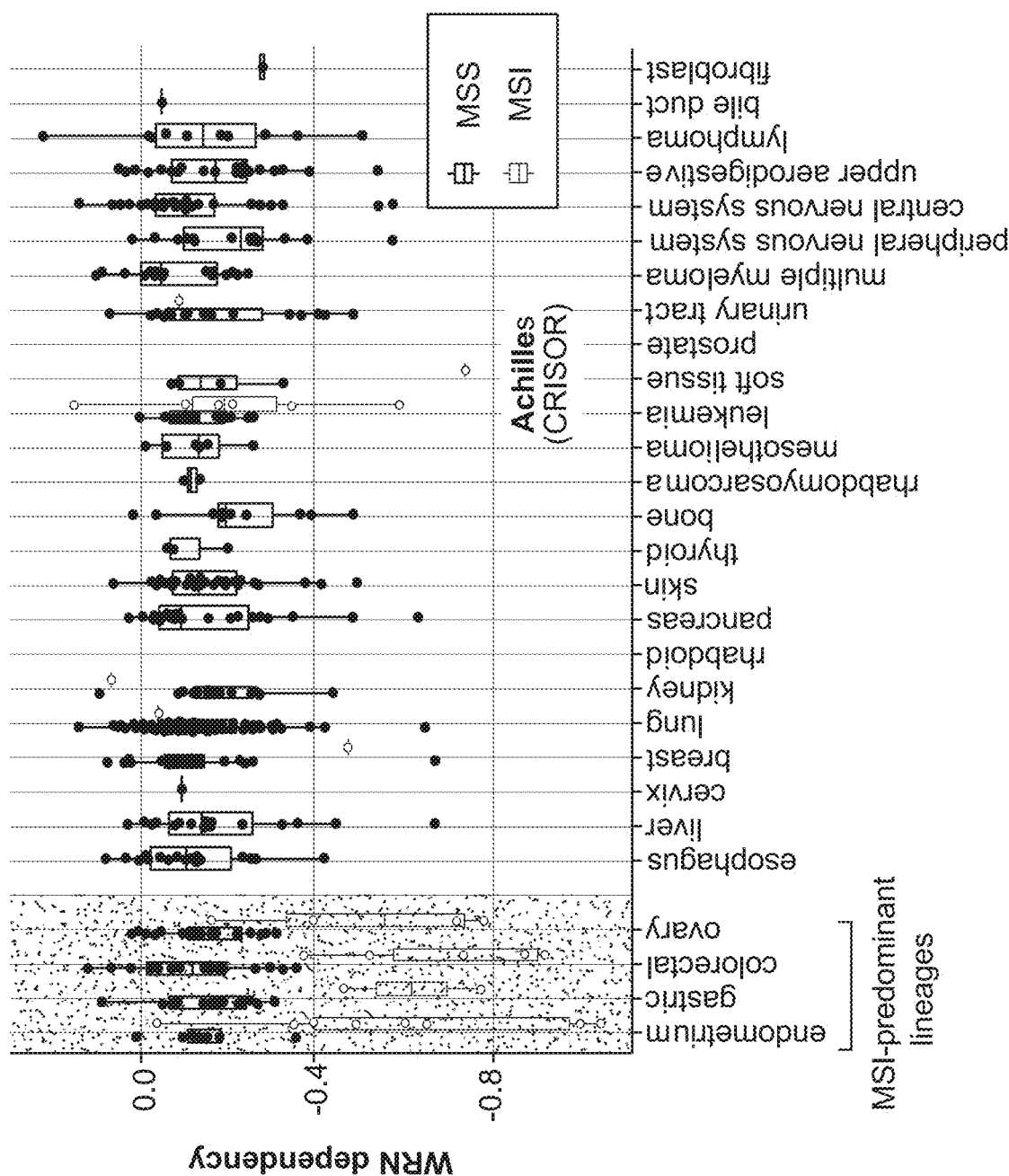
FIGS. 6A to 6D show that MSI cells from MSI-predominant lineages have a greater mutational burden and WRN dependency.
Figure 6A:
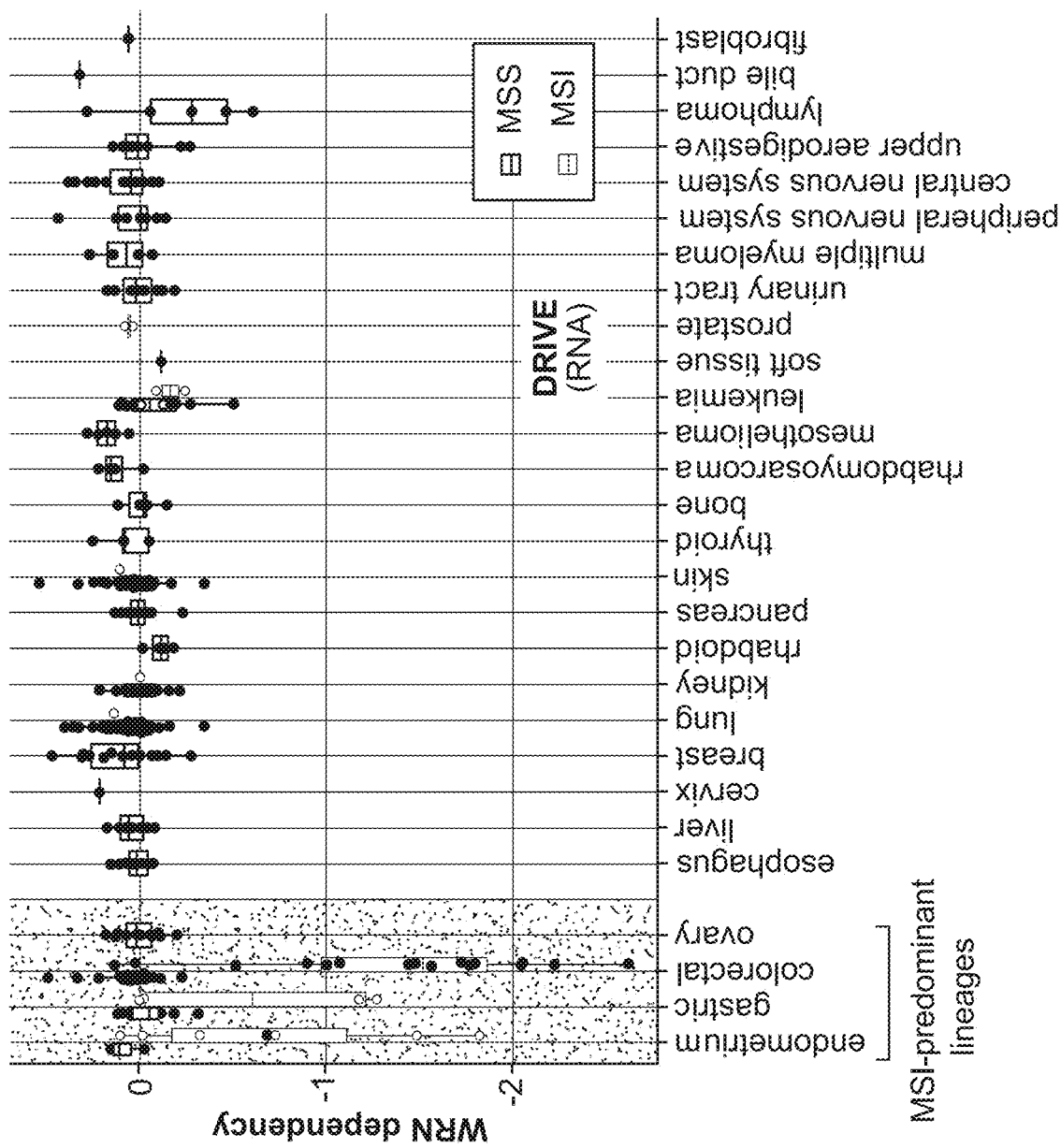
Figure 6B:
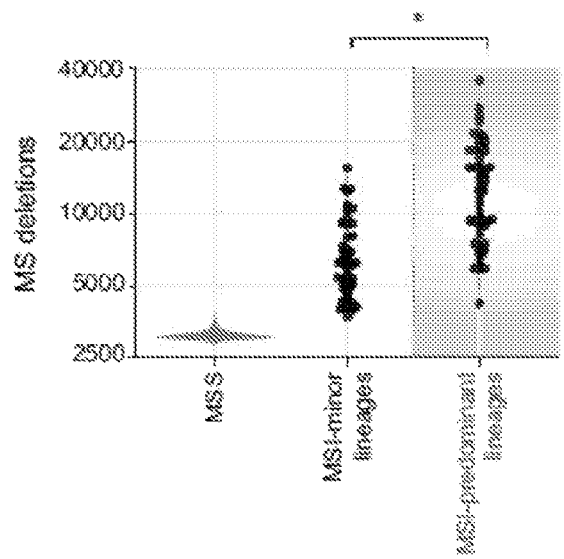
Figure 6C:
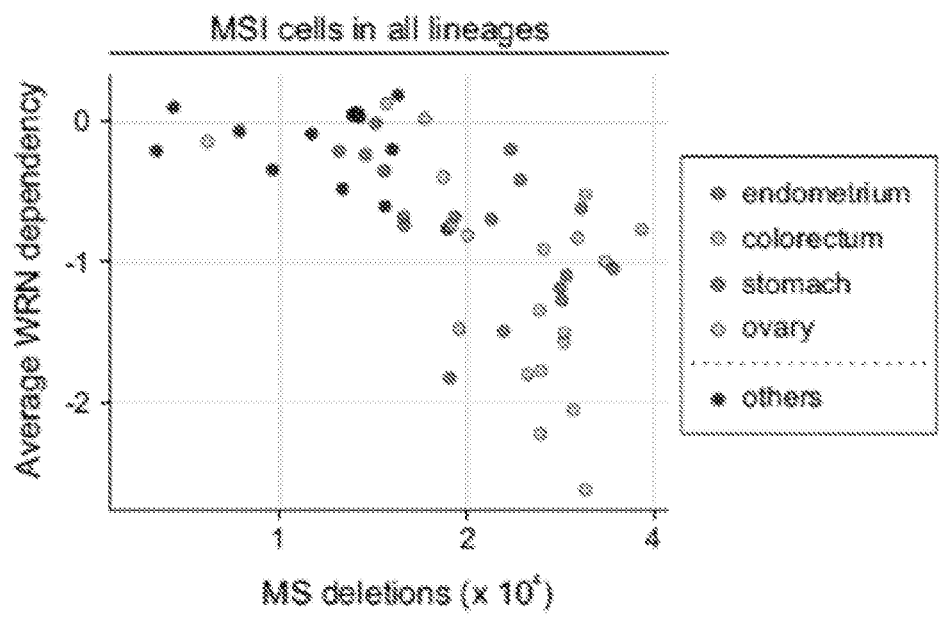
Figure 6D:
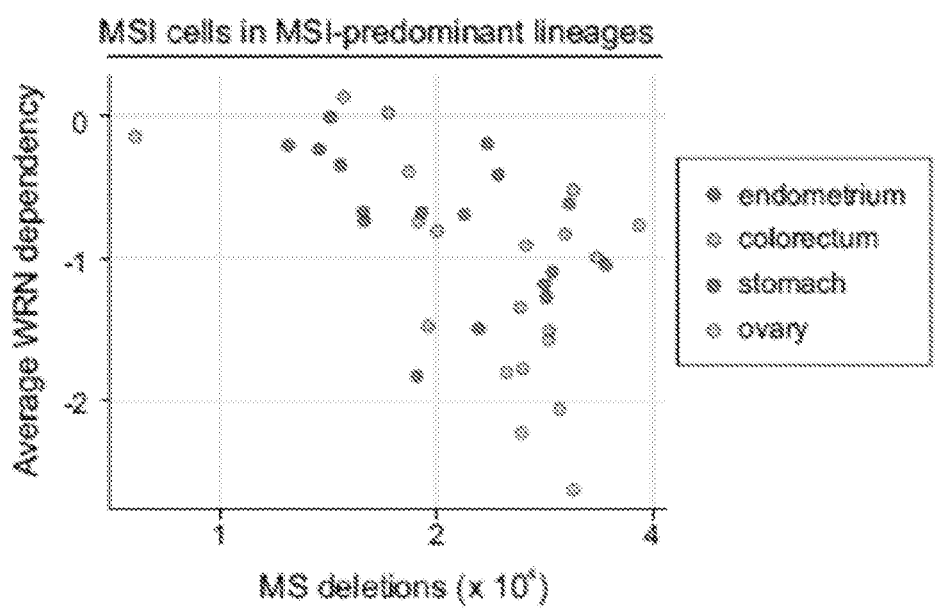

MSI is most commonly observed in colorectal, endometrial, gastric and ovarian cancers. MSI cell lines from these four lineages (n=37) showed greater dependence on WRN than their MSS counterparts (n=91; $P=4.2 \times 10^{-13}$, Wilcoxon rank-sum test; FIG. 6A). 14 MSI cell lines were identified from lineages in which MSI was less common (six leukemia lines, two prostate cancer lines and single models of other lineages). However, these MSI cell lines were distinct and contained a median 0.56-fold fewer deletion mutations in microsatellite regions compared to typical lineages ($P=1.7 \times 10^{-9}$; FIG. 6B). The lines from lineages in which MSI was less common were also less dependent on WRN ($P=1.1 \times 10^{-5}$; FIG. 6C), despite possessing events that are predictive of MMR deficiency (Table 2 of priority document U.S. Ser. No. 62/853,412). Correspondingly, the specificity of MSI as a biomarker for WRN dependency was improved by delineating MSI within MSI-predominant lineages (FIGS. 6D and 6E). These observations indicated that WRN dependency is not simply a result of MMR deficiency, but required specific lineages and/or a stronger mutation phenotype. Indeed, WRN dependency correlated with the number of microsatellite deletions within all MSI cell lines and in MSI predominant lineages (Spearman's $\rho=-0.74$, n=54, $P<2.2 \times 10^{-16}$; Spearman's $\rho=-0.57$, n=37, $P=3.3 \times 10^{-4}$, respectively; FIGS. 6C and 6D).

Figure 7A:
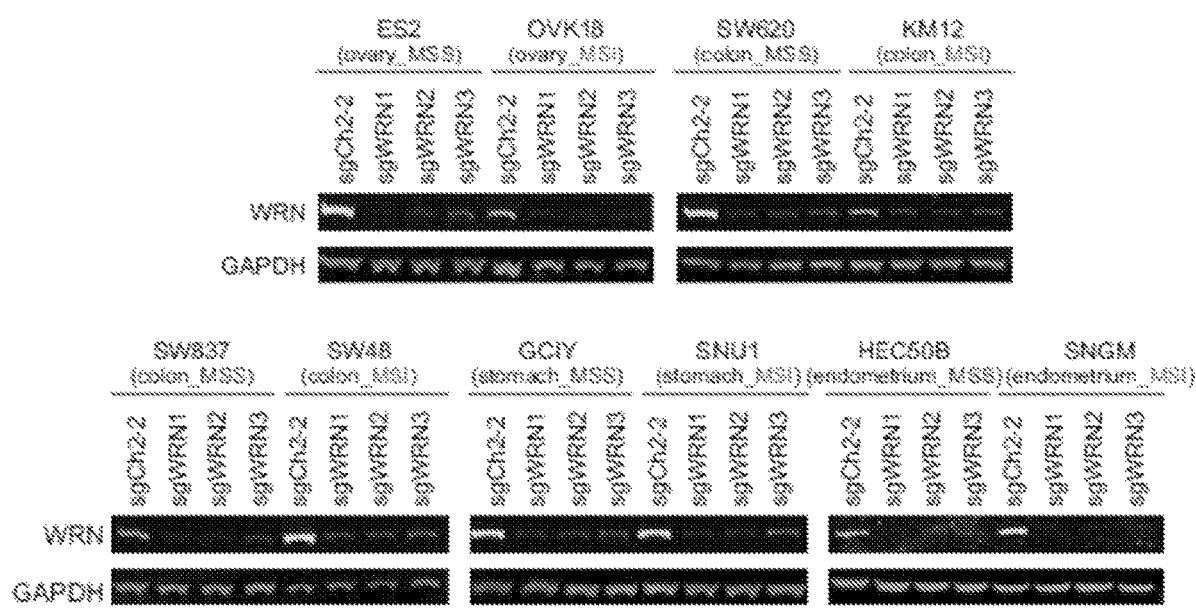
FIG. 7A to 7D show that WRN depletion preferentially impaired MSI cell viability.
Figure 7B:
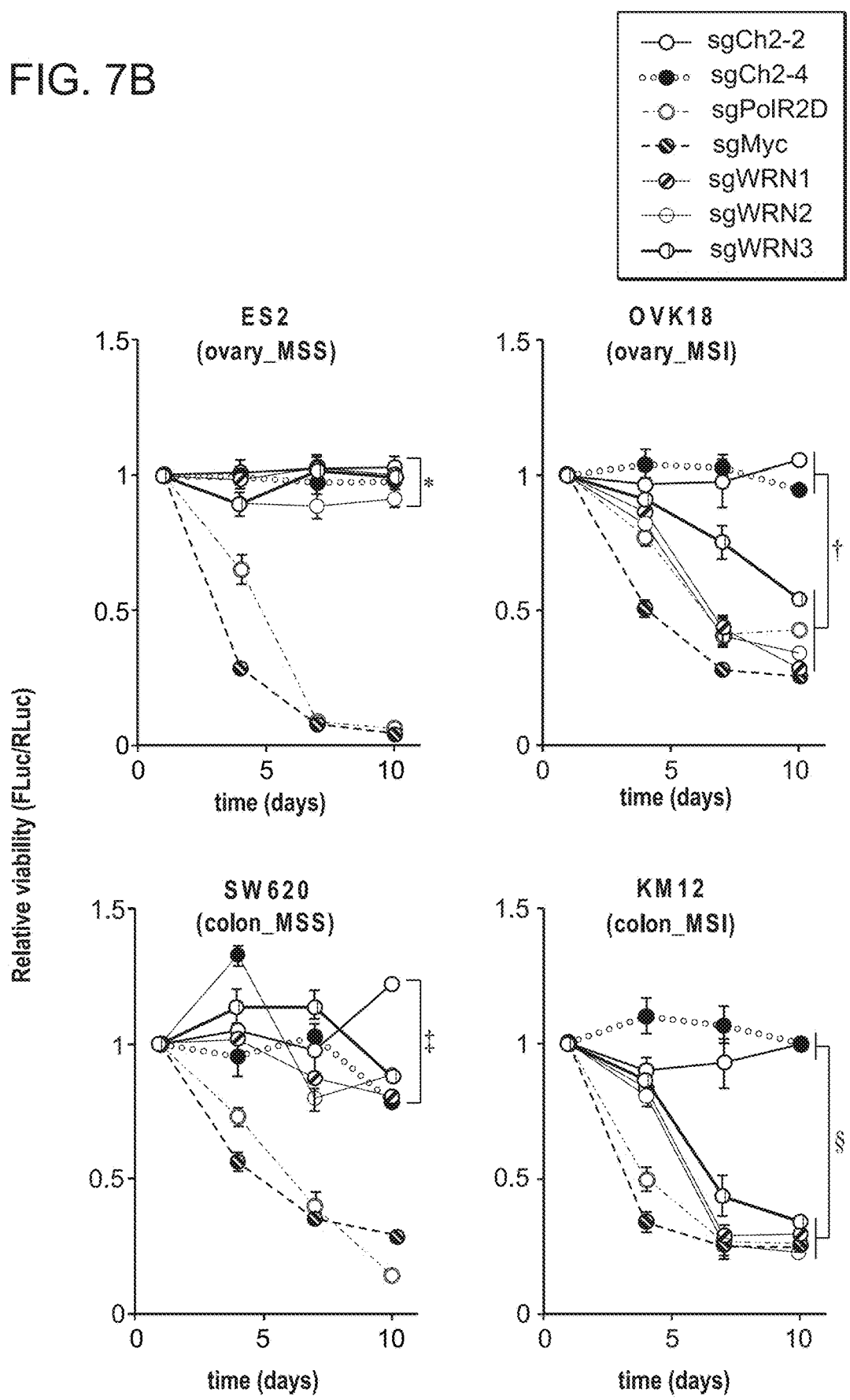
Figure 7C:
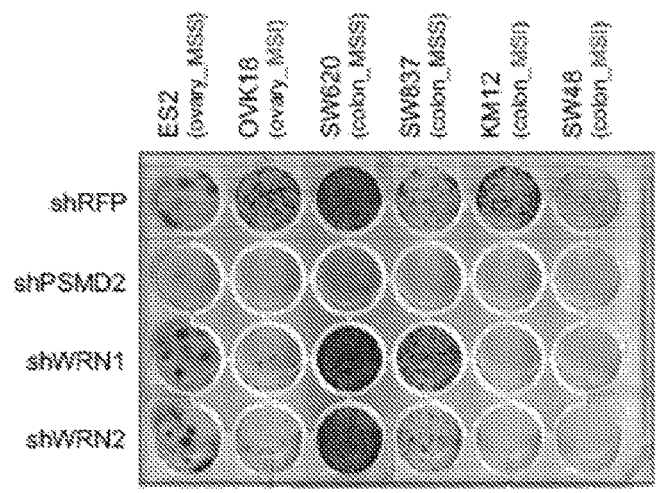
Figure 7D:
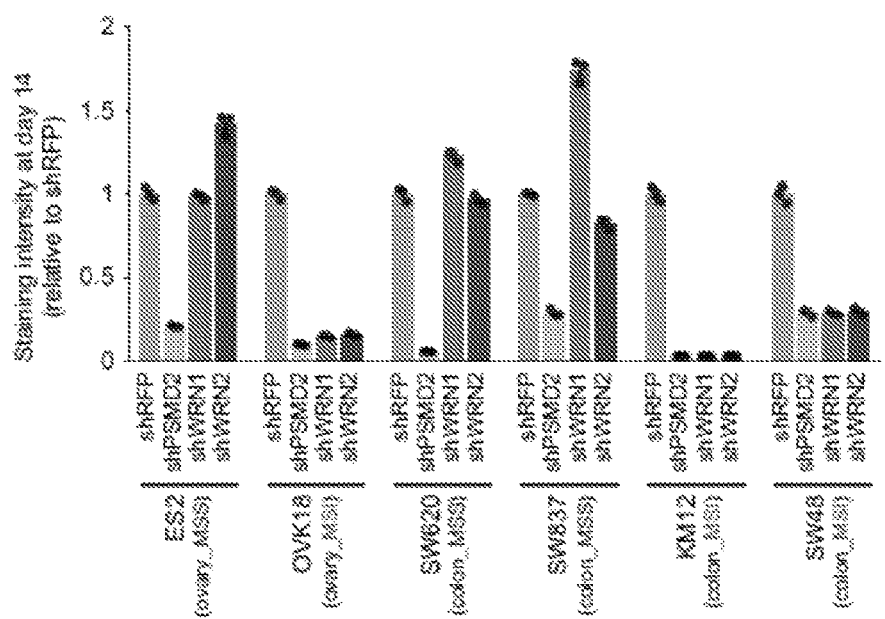

To further assess WRN dependency, three single-guide RNAs (sgRNAs) that targeted WRN were validated using immunoblots (FIG. 7A). WRN knockouts were evaluated in five MSS and five MSI cell lines, all of which were from MSI-predominant lineages, using an eight-day viability assay. Effects of WRN knockout were comparable to 'pan-essential' controls in MSI cell lines. WRN silencing in MSS models instead approximated negative controls, in which intergenic regions were targeted (FIG. 2A). Similarly, WRN depletion impaired the viability of MSI cells despite negligible effects in MSS cells in a 10-day competitive growth assay (FIG. 7B). Complementing these CRISPR-Cas9 data, WRN silencing with short hairpin RNA (shRNA) impaired cell viability in MSI, but not MSS, cells (FIGS. 7C and 7D). To validate that these phenotypes were attributable to WRN inactivation, a sgRNA was developed that targeted a WRN exon-intron junction (WRNEU sgRNA), silencing endogenous WRN, but not exogenous WRN cDNA (FIG. 2B). Correspondingly, WRN cDNA rescued Cas9-expressing KM12 cells from WRNEU sgRNA, but not WRN sgRNA 2, which targets endogenous and exogenous WRN (FIG. 2C). These data demonstrated that the viability loss observed in MSI cells was attributable to WRN inactivation.

The above findings indicated that WRN dependence with MSI could be exploited by WRN inhibition. WRN functions as both a 3'-5' exonuclease and 3'-5' helicase in processes such as DNA repair, DNA replication and telomere maintenance (14, 15). To determine which WRN enzymatic function was essential, rescues were attempted of WRN EIJ sgRNA using exonuclease-dead (E84A), helicase-dead (K577M) or dually exonuclease- and helicase-dead (E84A/K577M) versions of WRN cDNA14 in KM12 cells. Exonuclease inactivation did not attenuate rescue, which indicated that this function is dispensable. By contrast, helicase inactivation prevented rescue (FIGS. 2B and 2C), which indicated that the helicase domain is a candidate therapeutic target.

WRN dependency was then validated in vivo using xenografts of KM12 cells transduced with doxycycline-inducible shRNAs that targeted WRN (WRN shRNA 1) or control (WRN-C911 shRNA 1) in which nucleotides 9-11 of WRN shRNA 1 were mutated to the complementary nucleotides, thus maintaining the 'seed' sequence associated with shRNA off-target effects (16). Induction of WRN shRNA 1 but not WRNC911 shRNA 1 significantly impaired tumor growth (FIG. 2D). Substantial depletion of WRN was observed after induction of WRN shRNA 1 in vivo. However, WRN levels recovered by three weeks (FIG. 2E), mirroring tumor growth recovery, which indicated that WRN re-expression was required to overcome induction of WRN shRNA 1. Further, a shRNA targeting WRN impaired the viability of a newly generated patient-derived organoid obtained from a colon cancer with MSI (FIGS. 2F and 2G). By demonstrating the synthetic lethal relationship in vivo and in a patient-derived model, these data support WRN as a therapeutic target for cancers with MSI.

To determine the basis of WRN dependency, cell cycle analyses were performed. WRN silencing reduced the proportion of MSI cells in S phase and increased the number of cells in G1 or G2/M phases, which indicated cell cycle arrest at either G1 or G2/M phases (FIGS. 8A and 8B). Furthermore, analyses of annexin V and propidium iodide staining demonstrated the induction of apoptosis and cell death in MSI cells after WRN silencing (FIGS. 8A, 8C, and 8D). By contrast, MSS cell lines showed no significant evidence of increased cell cycle arrest nor cell death after WRN silencing.

Figure 3A:
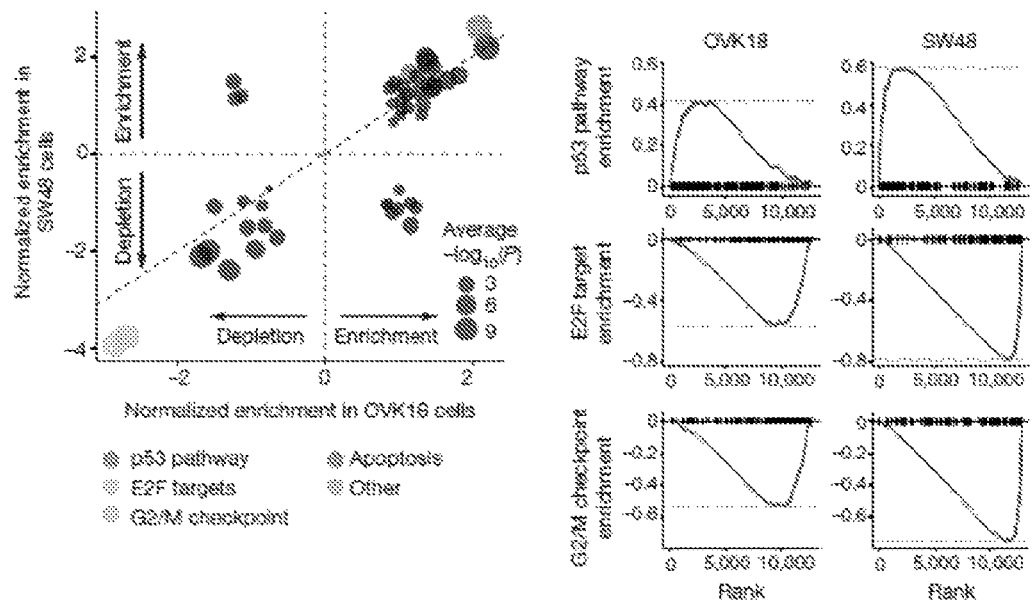
FIGS. 3A to 3C show that WRN depletion in MSI cells induced cell cycle arrest, apoptosis, and a p53 response.
Figure 3B:
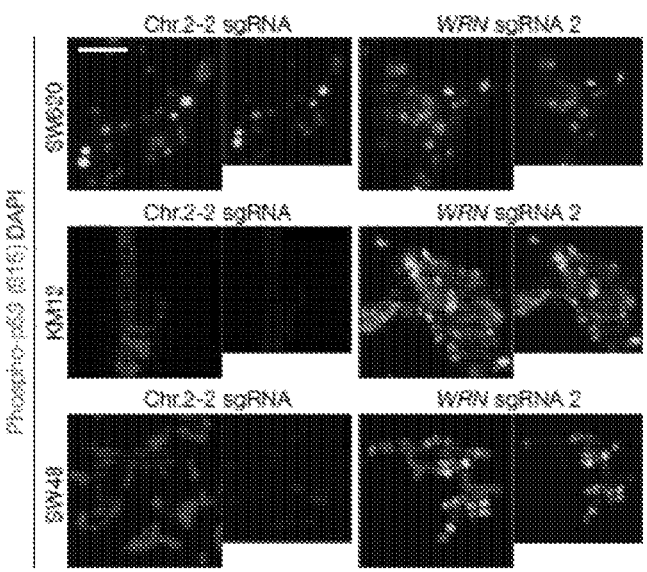
Figure 3C:
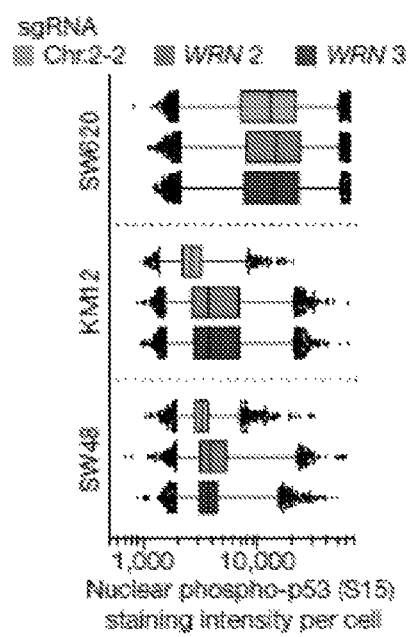
Figure 9A:
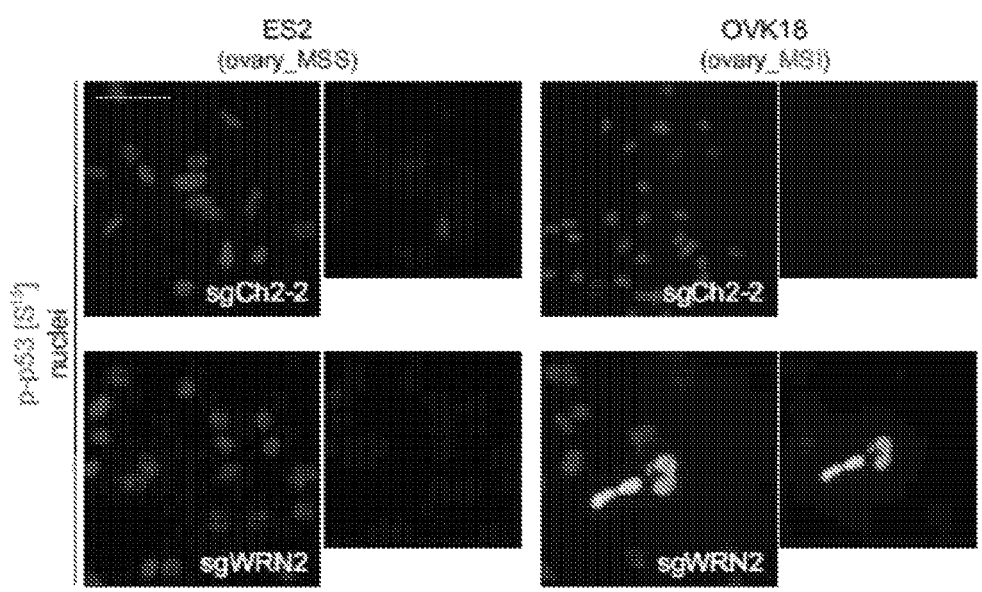
FIGS. 9A to 9G show that WRN depletion activated a p53 response in MSI cells.
Figure 9B:
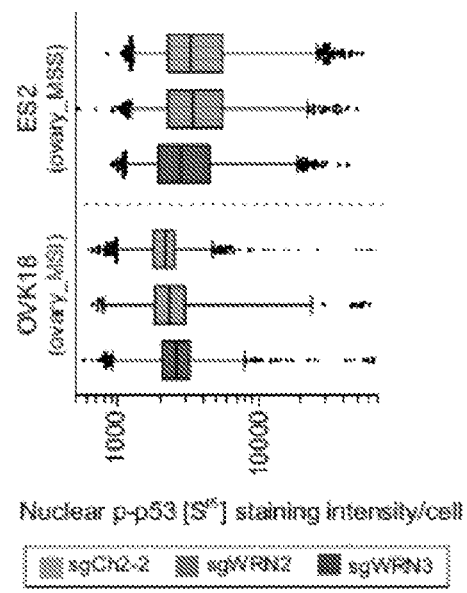
Figure 9C:
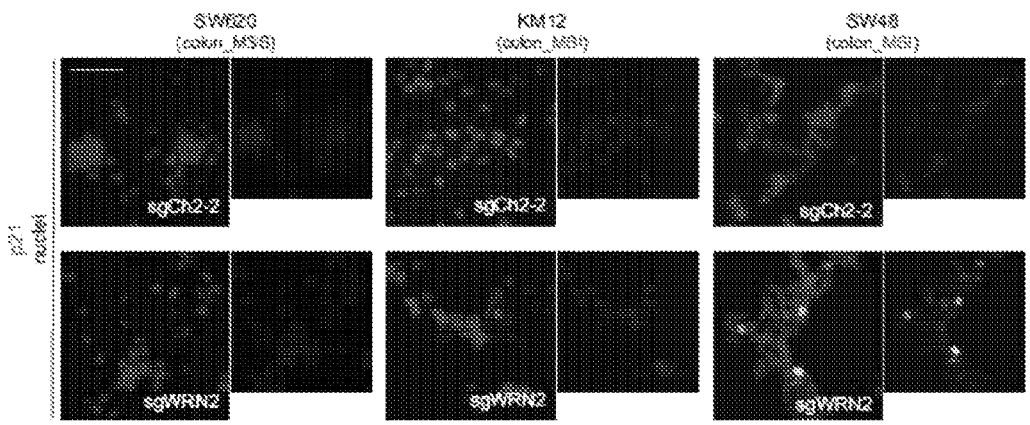
Figure 9D:
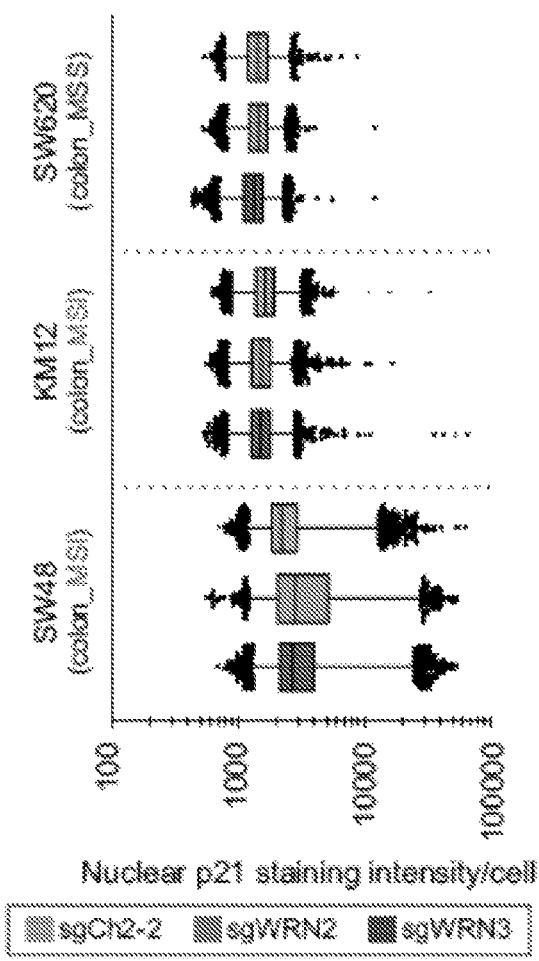
Figure 9E:
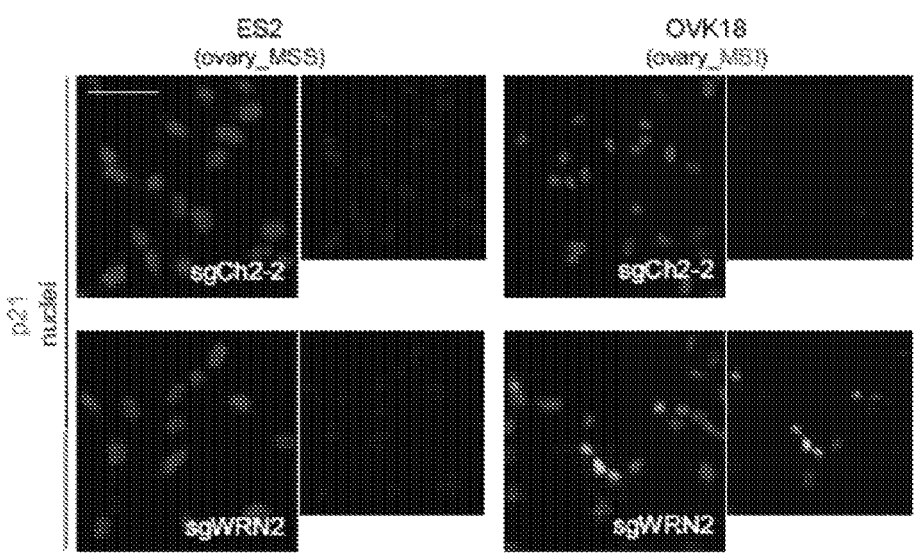
Figure 9F:
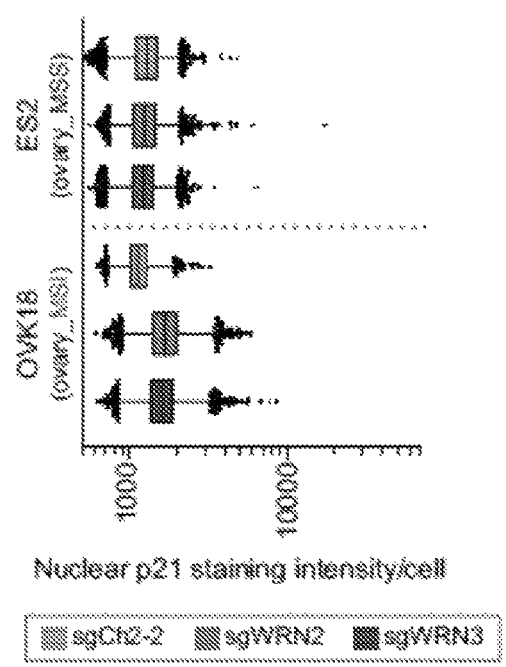
Figure 9G:
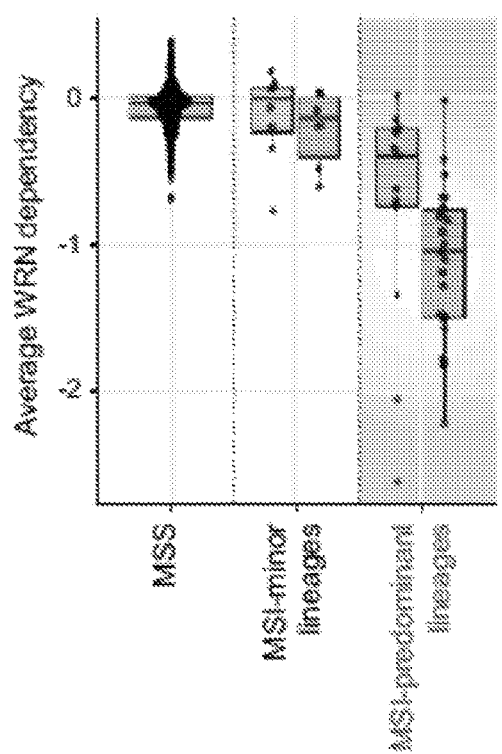

Consistent with the above-described cell cycle and apoptosis assay results, mRNA-sequencing analysis of WRN silencing in MSI cells revealed downregulation of genes associated with G2/M checkpoint progression and E2F target signatures, and upregulated signatures of apoptosis. This analysis additionally revealed p53 activation in MSI-depleted MSI cells (FIG. 3A). Immunofluorescence imaging of proteins in MSI models after WRN silencing showed an increase in phosphorylated (phospho-) p53 (S15), which indicated activation of p53 (17). By contrast, WRN depleted MSS models exhibited substantially weaker changes in phosphor-p53 intensity ($P<2\times10^{-16}$, contrast test of mean fold change in MSS versus MSI lines; FIGS. 3B and C, and FIGS. 9A and 9B). WRN depletion in TP53 wild-type MSI cells increased protein levels of the cyclin-dependent kinase inhibitor p21, another indication of p53 activation. By contrast, there were significantly weaker changes in p21 expression after WRN silencing in MSS and TP53-mutant MSI cells ($P<2\times10^{-16}$, fold change in MSI TP53 wild-type versus MSS or TP53-null cells; FIGS. 9C-9F). Based on this result, cell lines were subsequently stratified by both MSI and p53 status. Whereas p53-intact MSI cell lines (n=23) were more sensitive to WRN loss than their p53-impaired (n=13) counterparts (P=0.02, Wilcoxon rank-sum test; MSI cell lines from lineages in which MSI were common only), both wild-type and mutant TP53 MSI cell lines were dependent on WRN (FIG. 9G). These data indicated that although WRN loss led to p53 induction, p53 activity contributed to, but was not solely responsible for, WRN dependence.

Figure 11A:
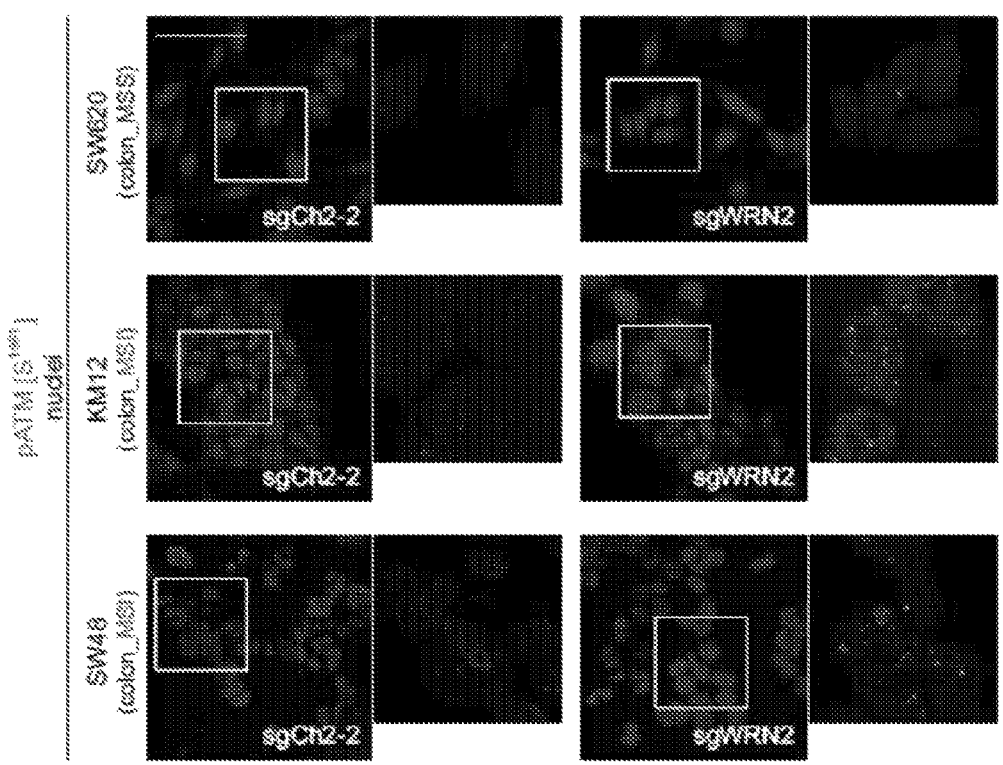
FIGS. 11A to 11E show that WRN depletion preferentially induced DSB responses in MSI cells.
Figure 11B:
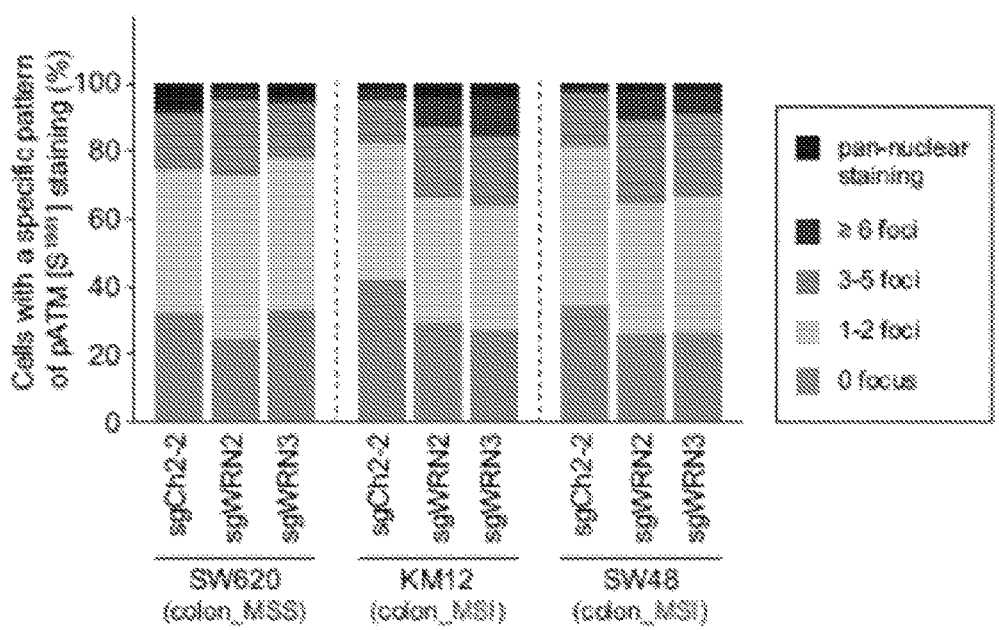
Figure 11C:
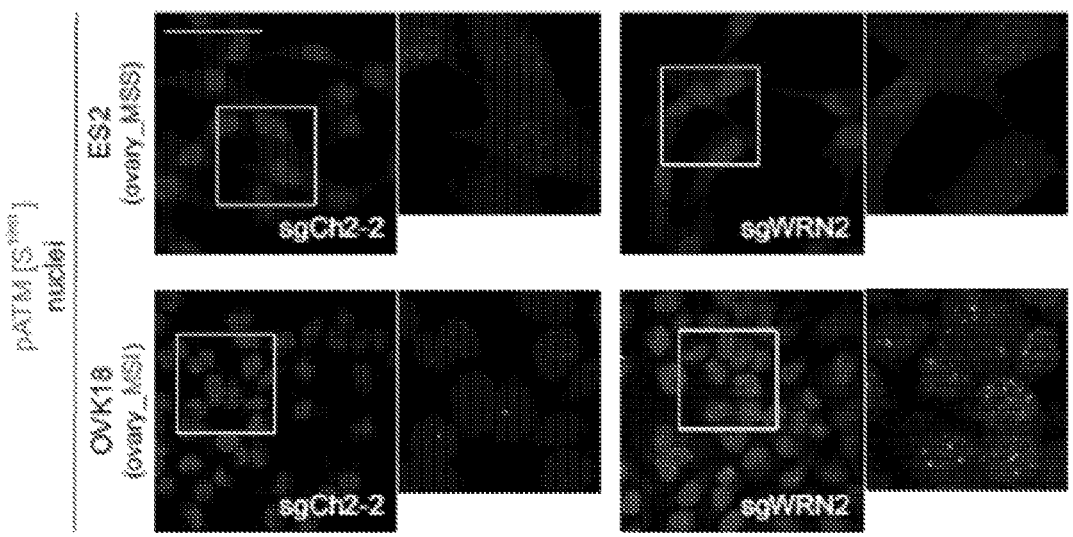
Figure 11D:
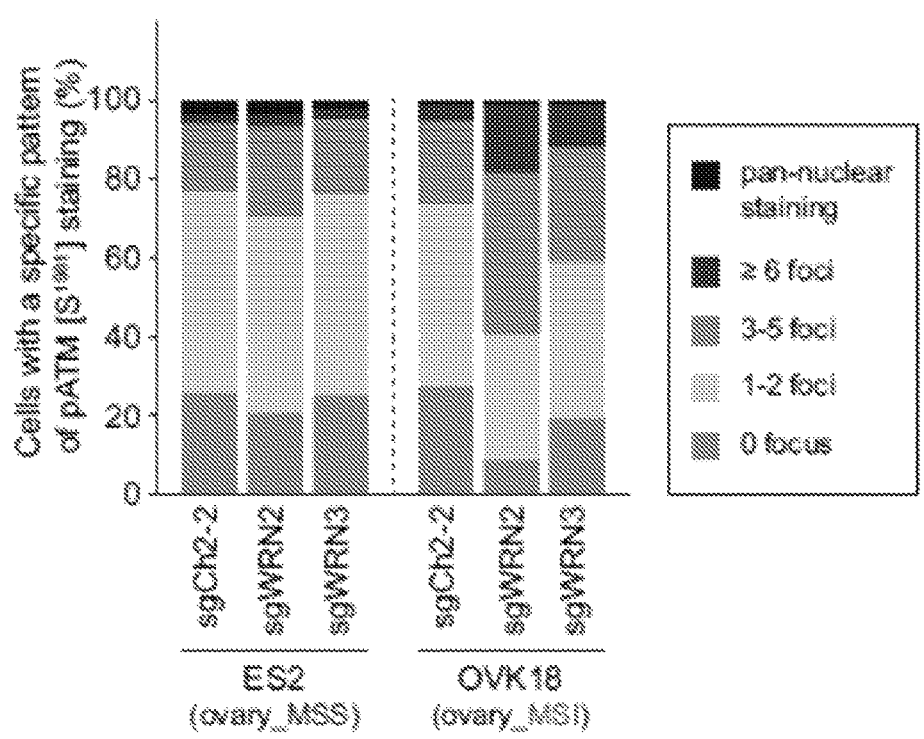
Figure 11E:
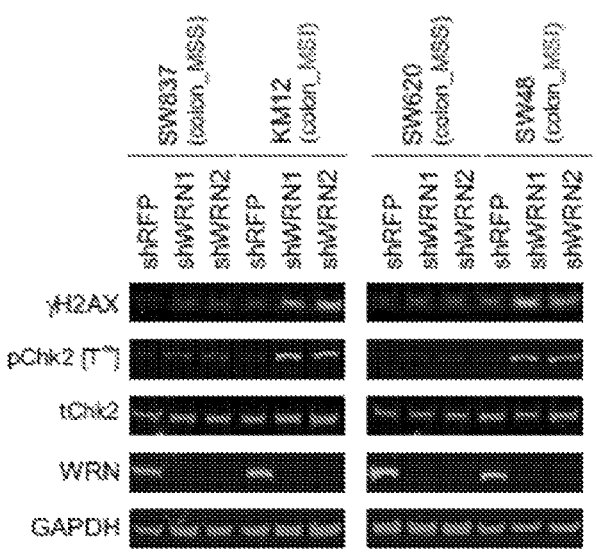

The finding of increased p53 (S15) phosphorylation, a phosphorylation target of DNA-damage response kinases ATR and ATM (17), indicated that WRN loss concomitant with MSI leads to DNA damage. This conclusion is consistent with the roles of p53 and WRN in responding to DNA damage and preserving DNA integrity, respectively (15, 17). Indeed, biallelic germline inactivation of WRN has been described to cause Werner syndrome, which is characterized by premature ageing and an increased incidence of cancer due to impaired DNA damage repair and telomeric shortening, which leads to chromosomal aberrations (15). WRN silencing in MSI, but not MSS, cells led to substantially increased γH2AX and 53BP1 foci, which are markers of double-stranded DNA breaks (DSBs) (FIGS. 4A-4C and FIGS. 10A-10H). These findings were corroborated by increased formation of phospho-ATM (S1981) foci and CHK2 (T68) phosphorylation, which are indicative of DSB responses that are known to activate p53 and anti-proliferative signaling pathways (18) (FIGS. 11A-11E). γH2AX expression increased in MSI cells treated with a shRNA against WRN in vitro and in vivo, which demonstrated that DSBs are not just a consequence of CRISPR-Cas9 activity (FIG. 2E and FIG. 11E). These observations also explained why p53-impaired MSI cells were sensitive to WRN depletion, as DSBs are toxic to cells, independent of p53 status (19).

Given the role of WRN as protective of telomeres (15) it was informative to assess whether a telomere defect precipitated the synthetic lethal relationship observed with WRN silencing. To evaluate chromosomal integrity with WRN silencing, metaphase spreads of two MSI and two MSS cell lines were evaluated with telomere fluorescence in situ hybridization (FISH), 96 h after induction of WRN shRNA 1. WRN silencing induced DSBs and fragmentation throughout chromosomes in MSI cells, but not in MSS cells. However, specific telomeric defects such as increased chromosomal end-to-end fusions or telomeric signal loss were not observed. Although many MSI cells with chromosomal fragmentation were observed after WRN silencing, many MSI cells were also identified in which there were only a few DSBs (FIGS. 4D and 4E, and FIG. 12A). Because this assay required viable cells to cycle into metaphase, these data indicated that DSBs caused the lethal effects of WRN loss and were not merely a consequence of cell death.

Because the above-described FISH data revealed diffuse DSBs in WRN-depleted MSI cells, it was contemplated that chromosomes required WRN to maintain genomic stability with MSI. Localization of WRN was analyzed using immunofluorescence staining and microscopy. After demonstrating the specificity of WRN immunofluorescence staining (FIG. 12B), predominantly dispersed staining was observed across the nucleoplasm in MSI cells, whereas greater co-localization of WRN with the nucleolar marker fibrillarin (FIGS. 12B-12D) was found. Less nucleoplasmic staining was found in MSS cells. Because WRN has been demonstrated to respond to DNA damage by disseminating from the nucleolus towards the nucleoplasm (20), these data indicated that WRN was recruited to maintain genomic integrity in MSI cells.

The relationship between MMR deficiency and WRN dependency was subsequently evaluated. It was considered important to determine whether MSI leads to recurrent mutations and inactivation of another gene, creating a dependency on WRN. The second most significant dependency with MSI was RPL22L1, a dependency described in MSI that is attributable to an inactivating mutation of its paralogue, RPL22 (11) (FIG. 1C). The screening dataset was analyzed, and no gene was identified for which a loss could account for the preferential dependency on WRN of cells with MSI (FIG. 13A). Neither was there any increased dependency of WRN identified in cell lines with hypermutations that were due to mutations in polymerase epsilon (POLE) (21) (FIG. 13B and Table 2 of priority document U.S. Ser. No. 62/853,412), which indicated that hypermutability alone did not account for WRN dependency.

Whether MMR deficiency contributes to WRN dependence was then examined using a model in which MMR activity of the MSI colorectal cell line HCT11 (in which MLH1 and MSH3 are mutated) was restored by introducing chromosomes 3 and 5 (Chr.3+5), which included MLH1 and MSH3, respectively (22) (FIG. 14A). WRN knockdown led to γH2AX accumulation and impaired viability of parental HCT116 and control cells in which an additional chromosome 2 was introduced. By contrast, Chr.3+5 transfer suppressed DSB accumulation and partially rescued viability from WRN shRNA treatment in a seven-day viability assay (FIG. 4F and FIG. 14B). The rescue was indeed attributable to MMR restoration as CRISPR-Cas9 knockout of MLH1 sensitized HCT116 cells that possess additional Chr.3+5 to WRN silencing and induced DSBs after WRN silencing (FIGS. 14C and 14D). Longer-term clonogenic assays with HCT116 cells established that rescue of WRN dependency is modest with MMR restoration, but abolished with MLH1 knockout (FIGS. 14E and 14F).

The above-described results indicated that MMR deficiency alone contributed to, but did not fully explain, the synthetic lethal interaction identified herein. The instant findings also indicated that genomic lesions that accumulate with MSI promote WRN dependence. In particular, the potential relevance of accumulation of genomic lesions is consistent with the observation that MSI cells possessing fewer microsatellite deletions were less dependent on WRN. Without wishing to be bound by theory, it is believed that accumulating MSI defects could cooperate with MMR deficiency to form genomic structures that require WRN to resolve. Such structures could include insertion-deletion loops (23) and/or displacement loops (D-loops) between homologous DNA sequences (24, 25) which are known substrates for MMR machinery. Indeed, MMR deficiency in yeast has been described to create a dependency on Sgs1, which is a homolog of WRN and BLM, to resolve homologous D-loops that are normally rejected by MMR (26). Beyond the potential role of WRN in preventing DNA damage, loss of WRN in non-homologous end joining and/or homologous recombination could further contribute to the accumulation of DSBs (15). The instant disclosure has therefore revealed that WRN inactivation induced DSBs and activated DSB responses to promote cell death and cell cycle arrest preferentially in MSI cells. Although WRN and other DNA helicases were previously nominated as therapeutic targets (27), the instant disclosure has demonstrated WRN as a synthetic lethal target in cancer cells with MSI, clearly defining a population in which a WRN-based therapeutic can be used. Results presented herein, as well as those of Behan et al. (29), have supported efforts aimed at designing WRN helicase inhibitors to exploit WRN dependency in MSI cancers. More broadly, the instant results highlight the power of large-scale cancer profiling efforts (10-12, 29, 30) to identify cancer vulnerabilities and therapeutic biomarkers, while also illustrating how a cancer dependency map (11, 30) can accelerate the development of precision therapy for patients with cancer.

REFERENCES

1. Chan, D. A. & Giaccia, A. J. Harnessing synthetic lethal interactions in anticancer drug discovery. *Nat. Rev. Drug Discov.* 10, 351-364 (2011).
2. Ivy, S. P., de Bono, J. & Kohn, E. C. The 'Pushmi-Pullyu' of DNA repair: clinical synthetic lethality. *Trends Cancer* 2, 646-656 (2016).
3. Brown, J. S., Kaye, S. B. & Yap, T. A. PARP inhibitors: the race is on. *Br. J. Cancer* 114, 713-715 (2016).
4. Kim, T. M., Laird, P. W. & Park, P. J. The landscape of microsatellite instability in colorectal and endometrial cancer genomes. *Cell* 155, 858-868 (2013).
5. Cancer Genome Atlas Research Network. Comprehensive molecular characterization of gastric adenocarcinoma. *Nature* 513, 202-209 (2014).
6. Kunitomi, H. et al. New use of microsatellite instability analysis in endometrial cancer. *Oncol. Lett.* 14, 3297-3301 (2017).
7. Pal, T., Permuth-Wey, J., Kumar, A. & Sellers, T. A. Systematic review and meta-analysis of ovarian cancers: estimation of microsatellite-high frequency and characterization of mismatch repair deficient tumor histology. *Clin. Cancer Res.* 14, 6847-6854 (2008).
8. Le, D. T. et al. Mismatch repair deficiency predicts response of solid tumors to PD-1 blockade. *Science* 357, 409-413 (2017).
9. Overman, M. J. et al. Durable clinical benefit with nivolumab plus ipilimumab in DNA mismatch repair-deficient/microsatellite instability-high metastatic colorectal cancer. *J. Clin. Oncol.* 36, 773-779 (2018).
10. Meyers, R. M. et al. Computational correction of copy number effect improves specificity of CRISPR-Cas9 essentiality screens in cancer cells. *Nat. Genet.* 49, 1779-1784 (2017).
11. McDonald, E. R. III et al. Project DRIVE: a compendium of cancer dependencies and synthetic lethal relationships uncovered by large-scale, deep RNAi screening. *Cell* 170, 577-592 (2017).
12. Barretina, J. et al. The Cancer Cell Line Encyclopedia enables predictive modelling of anticancer drug sensitivity. *Nature* 483, 603-607 (2012).
13. Iorio, F. et al. A landscape of pharmacogenomic interactions in cancer. *Cell* 166, 740-754 (2016).
14. Swanson, C., Saintigny, Y., Emond, M. J. & Monnat, R. J. Jr. The Werner syndrome protein has separable recombination and survival functions. *DNA Repair* 3, 475-482 (2004).
15. Rossi, M. L., Ghosh, A. K. & Bohr, V. A. Roles of Werner syndrome protein in protection of genome integrity. *DNA Repair* 9, 331-344 (2010).
16. Buehler, E., Chen, Y. C. & Martin, S. C911: a bench-level control for sequence specific siRNA off-target effects. *PLoS ONE* 7, e51942 (2012).
17. Loughery, J., Cox, M., Smith, L. M. & Meek, D. W. Critical role for p53-serine 15 phosphorylation in stimulating transactivation at p53-responsive promoters. *Nucleic Acids Res.* 42, 7666-7680 (2014).
18. Shiloh, Y. & Ziv, Y. The ATM protein kinase: regulating the cellular response to genotoxic stress, and more. *Nat. Rev. Mol. Cell Biol.* 14, 197-210 (2013).
19. Nowsheen, S. & Yang, E. S. The intersection between DNA damage response and cell death pathways. *Exp. Oncol.* 34, 243-254 (2012).
20. Bendtsen, K. M. et al. Dynamics of the DNA repair proteins WRN and BLM in the nucleoplasm and nucleoli. *Eur. Biophys. J.* 43, 509-516 (2014).
21. Billingsley, C. C. et al. Polymerase ε (POLE) mutations in endometrial cancer: clinical outcomes and implications for Lynch syndrome testing. *Cancer* 121, 386-394 (2015).
22. Haugen, A. C. et al. Genetic instability caused by loss of MutS homologue 3 in human colorectal cancer. *Cancer Res.* 68, 8465-8472 (2008).
23. Sidorova, J. M. Roles of the Werner syndrome RecQ helicase in DNA replication. *DNA Repair* 7, 1776-1786 (2008).
24. Spies, M. & Fishel, R. Mismatch repair during homologous and homeologous recombination. *Cold Spring Harb. Perspect. Biol.* 7, a022657 (2015).
25. Opresko, P. L., Sowd, G. & Wang, H. The Werner syndrome helicase/exonuclease processes mobile D-loops through branch migration and degradation. *PLoS ONE* 4, e4825 (2009).
26. Myung, K., Datta, A., Chen, C. & Kolodner, R. D. SGS1, the *Saccharomyces cerevisiae* homologue of BLM and WRN, suppresses genome instability and homeologous recombination. *Nat. Genet.* 27, 113-116 (2001).
27. Aggarwal, M., Banerjee, T., Sommers, J. A. & Brosh, R. M. Jr. Targeting an Achilles' heel of cancer with a WRN helicase inhibitor. *Cell Cycle* 12, 3329-3335 (2013).
28. Lebel, M. & Monnat, R. J. Jr. Werner syndrome (WRN) gene variants and their association with altered function and age-associated diseases. *Ageing Res. Rev.* 41, 82-97 (2018).
29. Behan, F. M. et al. Prioritization of cancer therapeutic targets using CRISPR-Cas9 screens. *Nature* (2019).
30. Tsherniak, A. et al. Defining a cancer dependency map. *Cell* 170, 564-576 (2017).
31. Broad DepMap. DepMap Achilles 18Q4 public. FigShare version 2. figshare.com/articles/DepMap_Achilles_18Q4_public/7270880 (2018).
32. McFarland, J. M. et al. Improved estimation of cancer dependencies from large-scale RNAi screens using model-based normalization and data integration. *Nat. Commun.* 9, 4610 (2018).
33. Cancer Data Science. DEMETER2 data. FigShare version 5/figshare.com/articles/DEMETER2_data/6025238/5 (2018).
34. Cancer Cell Line Encyclopedia Consortium. Pharmacogenomic agreement between two cancer cell line data sets. *Nature* 528, 84-87 (2015).
35. Giacomelli, A. O. et al. Mutational processes shape the landscape of TP53 mutations in human cancer. *Nat. Genet.* 50, 1381-1387 (2018).
36. Ritchie, M. E. et al. limma powers differential expression analyses for RNA-sequencing and microarray studies. *Nucleic Acids Res.* 43, e47 (2015).
37. Benjamini, Y. & Hochberg, Y. Controlling the false discovery rate: a practical and powerful approach to multiple testing. *J. R. Stat. Soc.* B 57, 289-300 (1995).
38. Robinson, M. D. & Oshlack, A. A scaling normalization method for differential expression analysis of RNA-seq data. *Genome Biol.* 11, R25 (2010).
39. Robinson, M. D., McCarthy, D. J. & Smyth, G. K. edgeR: a Bioconductor package for differential expression analysis of digital gene expression data. *Bioinformatics* 26, 139-140 (2010).
40. Law, C. W., Chen, Y., Shi, W. & Smyth, G. K. voom: precision weights unlock linear model analysis tools for RNA-seq read counts. *Genome Biol.* 15, R29 (2014).
41. Subramanian, A. et al. Gene set enrichment analysis: a knowledge-based approach for interpreting genome-wide expression profiles. *Proc. Natl Acad. Sci. USA* 102, 15545-15550 (2005).
42. Sergushichev, A. A. An algorithm for fast preranked gene set enrichment analysis using cumulative statistic calculation. Preprint at www.biorxiv.org/content/10.1101/060012v1 (2016).
43. Liberzon, A., et al. The molecular signatures database hallmark gene set collection. *Cell Syst.* 1, 417-425 (2015).
44. Boj, S. F. et al. Organoid models of human and mouse ductal pancreatic cancer. *Cell* 160, 324-338 (2015).
45. Shibue, T., Brooks, M. W., Inan, M. F., Reinhardt, F. & Weinberg, R. A. The outgrowth of micrometastases is enabled by the formation of filopodium-like protrusions. *Cancer Discov.* 2, 706-721 (2012).
46. Lenth, R. V. Least-squares means: the R package Ismeans. *J. Stat. Softw.* 69, 1-33 (2016).
47. Dejmek, J., Iglehart, J. D. & Lazaro, J. B. DNA-dependent protein kinase (DNA-PK)-dependent cisplatin-induced loss of nucleolar facilitator of chromatin transcription (FACT) and regulation of cisplatin sensitivity by DNA-PK and FACT. *Mol. Cancer Res.* 7, 581-591 (2009).
48. Bates, D. et al. Fitting linear mixed-effects models using lme4. *J. Stat. Softw.* 67, 1-48 (2015).
49. Nagel, Z. D. et al. Multiplexed DNA repair assays for multiple lesions and multiple doses via transcription inhibition and transcriptional mutagenesis. *Proc. Natl Acad. Sci. USA* 111, E1823-E1832 (2014).
50. Cancer Data Science. DepMap Datasets for WRN manuscript. FigShare figshare.com/articles/DepMap_Datasets_for_WRN_manuscript/7712756 (2019).

All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

One skilled in the art would readily appreciate that the present disclosure is well adapted to carry out the objects and obtain the ends and advantages mentioned, as well as those inherent therein. The methods and compositions described herein as presently representative of preferred embodiments are exemplary and are not intended as limitations on the scope of the disclosure. Changes therein and other uses will occur to those skilled in the art, which are encompassed within the spirit of the disclosure, are defined by the scope of the claims.

In addition, where features or aspects of the disclosure are described in terms of Markush groups or other grouping of alternatives, those skilled in the art will recognize that the disclosure is also thereby described in terms of any individual member or subgroup of members of the Markush group or other group.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Embodiments of this disclosure are described herein, including the best mode known to the inventors for carrying out the disclosed invention. Variations of those embodiments may become apparent to those of ordinary skill in the art upon reading the foregoing description.

The disclosure illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present disclosure provides preferred embodiments, optional features, modification and variation of the concepts herein disclosed may be resorted to by those skilled in the art, and that such modifications and variations are considered to be within the scope of this disclosure as defined by the description and the appended claims.

It will be readily apparent to one skilled in the art that varying substitutions and modifications can be made to the invention disclosed herein without departing from the scope and spirit of the invention. Thus, such additional embodiments are within the scope of the present disclosure and the following claims. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context. Those skilled in the art will recognize, or be able to ascertain using no more than routine experimentation, many equivalents to the specific embodiments of the disclosure described herein. Such equivalents are intended to be encompassed by the following claims.

We claim:

1. A method for treating a subject having or at risk of developing a cancer that exhibits microsatellite instability (MSI) and/or impaired mismatch repair (MMR), the method comprising:

(a) obtaining a sample from a subject having or at risk of developing a cancer that exhibits MSI and/or impaired MMR, wherein the subject has not responded to a previously administered programmed cell death 1 (PD-1) inhibitor immunotherapy;

(b) identifying the presence or absence in the sample of MSI and/or impaired MMR; (c)

(c) selecting a WRN inhibitor as a treatment for the subject if MSI and/or impaired MMR is identified in the sample, thereby selecting a treatment for the subject having or at risk of developing a cancer that exhibits MSI and/or impaired MMR; and (d) administering the selected WRN inhibitor to the subject.

2. The method of claim 1, wherein the cancer is selected from the group consisting of an endometrial cancer, a gastric cancer, a colorectal cancer and an ovarian cancer.

3. The method of claim 1, wherein step (b) comprises performing a single multiplex PCR reaction that is analyzed by capillary electrophoresis.

4. The method of claim 1, wherein step (b) comprises classifying the sample on the basis of the density of deletions in microsatellite regions and total deletions from whole genome or whole exome data, optionally as compared to available whole genome or whole exome cancer cell line encyclopedia (CCLE) data.

5. The method of claim 1, wherein the WRN inhibitor is selected from the group consisting of:

distamycin A; netropsin; 3,6,9-trisubstituted acridine; NSC 617145; and NSC 19630; and an oligonucleotide inhibitor of WRN, optionally wherein the oligonucleotide inhibitor of WRN is selected from the group consisting of an antisense oligonucleotide, an siRNA and a sgRNA, optionally wherein the sgRNA is selected from the group consisting of sgWRN1 (GTAAATTGGAAAACCCACGG; SEQ ID NO: 1), sgWRN2 (ATCCTGTGGAACATACCATG; SEQ ID NO: 2), sgWRN3 (GTAGCAGTAAGTGCAACGAT; SEQ ID NO: 3), sgWRN-EIJ (AGCACGTACATAAGCATCAG; SEQ ID NO: 4), shWRN1-1 (CAGCACTGCCAATGGTTCCAA; SEQ ID NO: 5) and shWRN2-1 (GCCTTAACAGTCTGGTTAAAC; SEQ ID NO: 6).

6. The method of claim 1, wherein the WRN inhibitor specifically inhibits the helicase activity of WRN.

7. The method of claim 1, wherein the subject has further been previously administered a cytotoxic T-lymphocyte-associated protein 4 (CTLA-4) inhibitor immunotherapy has not responded to said immunotherapy.

8. The method of claim 1, wherein step (d) comprises administering a combination therapy comprising the selected WRN inhibitor and a second agent, optionally wherein:

the second agent is selected from the group consisting of a small molecule that induces DNA damage and/or modulates a DNA repair pathway and a chemotherapeutic agent, optionally wherein the small molecule that induces DNA damage and/or modulates a DNA repair pathway is calactin; and/or the second agent is selected from the group consisting of a PARP inhibitor, a CHK 1/2 inhibitor and a DNA-PKCS inhibitor, optionally wherein the PARP inhibitor is palbociclib, the CHK1/2 inhibitor is prexasertib and/or the DNA-PKCS inhibitor is NU7441.

9. The method of claim 1, wherein identifying step (b) comprises use of a kit of for identifying MSI and/or impaired MMR in a sample and selecting a subject for a WRN inhibitor therapy.

10. The method of claim 1, wherein the subject is human.

\* \* \* \* \*

UNITED STATES PATENT AND TRADEMARK OFFICE
CERTIFICATE OF CORRECTION

Page 1 of 1

PATENT NO. : 12,246,004 B2
APPLICATION NO. : 15/734131
DATED : March 11, 2025
INVENTOR(S) : Francisca Vazquez et al.

It is certified that error appears in the above-identified patent and that said Letters Patent is hereby corrected as shown below:

In the Specification

The following paragraph should be inserted immediately after the "CROSS-REFERENCE TO RELATED APPLICATIONS" paragraph:
--STATEMENT REGARDING FEDERALLY SPONSORED RESEARCH
This invention was made with government support under Grant No. CA009172 awarded by the National Institutes of Health. The government has certain rights in the invention.--

Signed and Sealed this
Twenty-sixth Day of August, 2025

Coke Morgan Stewart
*Acting Director of the United States Patent and Trademark Office*